(12) United States Patent
Ahn et al.

(10) Patent No.: US 9,464,044 B2
(45) Date of Patent: Oct. 11, 2016

(54) COMPOUND HAVING ABILITY TO INHIBIT 11BETA-HSD1 ENZYME OR PHARMACEUTICALLY ACCEPTABLE SALT THEREOF, METHOD FOR PRODUCING SAME, AND PHARMACEUTICAL COMPOSITION CONTAINING SAME AS ACTIVE INGREDIENT

(71) Applicants: AHN-GOOK PHARMACEUTICAL CO., LTD., Seoul (KR); BAMICHEM Co., Ltd., Incheon (KR); INCHEON UNIVERSITY INDUSTRY ACADEMIC COOPERATION FOUNDATION, Incheon (KR)

(72) Inventors: Soon Kil Ahn, Seoul (KR); Jin Auh, Seoul (KR); Nam Song Choi, Cheonan-si (KR); Chang Kyun Han, Seoul (KR); Tae-Jeong Kim, Suwon-si (KR); Kamsa Pae, Seoul (KR); Young June Shin, Gimhae-si (KR); Dong-Oh Han, Anyang-si (KR); Cheol Kyu Han, Seoul (KR)

(73) Assignees: AHN-GOOK PHARMACEUTICAL CO., LTD., Seoul (KR); BAMICHEM CO., LTD, Incheon (KR); INCHEON UNIVERSITY INDUSTRY ACADEMIC COOPERATION FOUNDATION, Incheon (KR)

( * ) Notice: Subject to any disclaimer, the term of this patent is extended or adjusted under 35 U.S.C. 154(b) by 0 days.

(21) Appl. No.: 14/409,414

(22) PCT Filed: Jun. 4, 2013

(86) PCT No.: PCT/KR2013/004913
§ 371 (c)(1),
(2) Date: Dec. 18, 2014

(87) PCT Pub. No.: WO2013/191396
PCT Pub. Date: Dec. 27, 2013

(65) Prior Publication Data
US 2015/0210635 A1    Jul. 30, 2015

(30) Foreign Application Priority Data
Jun. 20, 2012 (KR) .................. 10-2012-0066333

(51) Int. Cl.
| | |
|---|---|
| C07C 311/19 | (2006.01) |
| C07C 311/21 | (2006.01) |
| C07C 275/28 | (2006.01) |
| C07C 311/08 | (2006.01) |
| C07C 311/29 | (2006.01) |
| C07C 237/24 | (2006.01) |
| C07D 213/82 | (2006.01) |
| C07D 215/08 | (2006.01) |
| C07D 217/06 | (2006.01) |
| C07D 231/18 | (2006.01) |
| C07D 333/34 | (2006.01) |
| C07C 311/14 | (2006.01) |
| C07D 239/42 | (2006.01) |
| C07D 241/42 | (2006.01) |
| C07D 417/12 | (2006.01) |
| C07D 275/06 | (2006.01) |
| C07D 277/36 | (2006.01) |

(Continued)

(52) U.S. Cl.
CPC .......... *C07C 311/21* (2013.01); *C07C 237/24* (2013.01); *C07C 275/28* (2013.01); *C07C 311/08* (2013.01); *C07C 311/14* (2013.01); *C07C 311/19* (2013.01); *C07C 311/29* (2013.01); *C07D 209/08* (2013.01); *C07D 213/70* (2013.01); *C07D 213/82* (2013.01); *C07D 215/08* (2013.01); *C07D 217/06* (2013.01); *C07D 231/18* (2013.01); *C07D 239/42* (2013.01); *C07D 241/42* (2013.01); *C07D 275/06* (2013.01); *C07D 277/36* (2013.01); *C07D 277/56* (2013.01); *C07D 295/215* (2013.01); *C07D 307/64* (2013.01); *C07D 333/34* (2013.01); *C07D 417/12* (2013.01); *C07C 2101/02* (2013.01); *C07C 2101/18* (2013.01); *C07C 2102/42* (2013.01); *C07C 2103/74* (2013.01)

(58) Field of Classification Search
CPC C07C 311/21; C07C 311/19; C07C 2103/74
See application file for complete search history.

(56) References Cited

FOREIGN PATENT DOCUMENTS

| KR | 1020050088170 A | 9/2005 |
|---|---|---|
| KR | 1020110062797 A | 6/2011 |

(Continued)

OTHER PUBLICATIONS

Applied physiology, nutrition, and metabolism, 32 (1): 76-88.*

(Continued)

*Primary Examiner* — Yong Chu
(74) *Attorney, Agent, or Firm* — Lucas & Mercanti, LLP

(57) ABSTRACT

The present invention relates to a novel compound or a pharmaceutically acceptable salt thereof inhibiting 11β-HSD1 enzyme activity, a preparation method of the same, and a pharmaceutical composition comprising the same as an active ingredient. Since the compound of the present invention selectively inhibits the activity of 11β-HSD1 (11β-Hydroxysteroid dehydrogenase type 1), the compound of the invention can be effectively used as a therapeutic agent for the treatment of diseases caused by the over-activation of 11β-HSD1 such as non-insulin dependent type II diabetes, insulin resistance, obesity, lipid disorder, metabolic syndrome, and other diseases or condition mediated by the excessive activity of glucocorticoid.

3 Claims, No Drawings

(51) Int. Cl.
*C07D 209/08* (2006.01)
*C07D 277/56* (2006.01)
*C07D 295/215* (2006.01)
*C07D 213/70* (2006.01)
*C07D 307/64* (2006.01)

(56) References Cited

FOREIGN PATENT DOCUMENTS

| KR | 1020130016734 A | | 2/2013 |
|---|---|---|---|
| WO | 2011/149213 A2 | | 12/2011 |
| WO | WO 2011149213 A3 | * | 3/2012 |
| WO | WO 2013019019 A2 | * | 2/2013 |

OTHER PUBLICATIONS

Feldeisen SE, Tucker KL (2007), Appl Physiol Nutr Metab 32 (1): 46-60.*
C.T. Montague, et al; Perspectives in diabetes The perils of portliness; Diabetes, 2000; vol. 49, Jun. 2000; pp. 883-888.
M.F. Dallman, et al; Feast and famine: critical role of glucocorticoids with insulin in daily . . . ; Frontiers in Neuroendocrinology; 1993; vol. 14, No. 4; pp. 303-347.
I.J. Bujalska, et al; Differentiation of adipose stromal cells: the roles of glucocorticoids . . . ; Endocrinology; 1999; vol. 140; No. 7; pp. 3188-3196.
P. Bjorntorp, et al; Neuroendocrine abnormalities in visceral obesity; Int. Journ. of Obesity; 2000; vol. 24; pp. S80-S85.
T.C. Sandeep, et al; Pathophysiology of modulation of local glucocorticoid levels by . . . ; Trends in Endocrinology & Metabolism; 2001; vol. 12; No. 10; pp. 446-453.
H. Masuzaki, et al; A transgenic model of visceral obesity and the metabolic syndrome; Science; 2001; vol. 294; pp. 2166-2170.
Y. Kotelevtsev, et al; 11(beta)-hydroxysteroid dehydrogenase type 1 knockout mice show . . . ; Proc. Natl. Acad. Sci; 1997; vol. 94; pp. 14924-14929.
M.S. Cooper, et al; Expression and functional consequences of 11(beta)-hydroxysteroid . . . ; Bone; 2000; vol. 27; No. 3; pp. 375-381.
S. Rauz, et al; Expression and putative role of 11(beta)-hydroxysteroid dehydrogenase . . . ; Investigative Ophthalmology & Visual Science; 2001; vol. 42; No. 9; pp. 2037-2042.
International Search Report dated Sep. 5, 2013 for PCT/KR2013/004913.
Medicinal Chemistry; Shinil Books Company; 2011.
Korean Office Action dated Aug. 5, 2014 for corresponding Application No. 10-2014-0044028 and English translation thereof.

* cited by examiner

COMPOUND HAVING ABILITY TO INHIBIT 11BETA-HSD1 ENZYME OR PHARMACEUTICALLY ACCEPTABLE SALT THEREOF, METHOD FOR PRODUCING SAME, AND PHARMACEUTICAL COMPOSITION CONTAINING SAME AS ACTIVE INGREDIENT

CROSS-REFERENCE TO RELATED APPLICATIONS

This application is a 371 of PCT/KR2013/004913, filed Jun. 4, 2013, which in turn claims the benefit of Korean Patent Application No. 10-2012-0066333, filed Jun. 20, 2012, the entire disclosure of each of which is incorporated herein by reference.

BACKGROUND OF THE INVENTION

1. Field of the Invention

The present invention relates to a novel compound or a pharmaceutically acceptable salt thereof inhibiting 11β-HSD1 enzyme activity, a preparation method of the same, and a pharmaceutical composition comprising the same as an active ingredient.

2. Description of the Related Art

Metabolic syndrome is the disease in increase particularly in advanced countries, in Asia, and in developing countries. This disease is characterized by obesity, type II diabetes, hyperlipidemia, hypertension, arteriosclerosis, coronary heart disease, and chronic renal failure (C. T. Montague et al. (2000), Diabetes, 49, 883-888).

Glucocorticoid (cortisol in human, and corticosterone in rat and mouse) binding to glucocorticoid receptor is a steroid hormone found in almost every vertebrate (Dallman M F, Strack A M, Akana S F et al. 1993; Front Neuroendocrinol 14, 303-347).

This hormone regulates the expressions of liver enzymes involved in gluconeogenesis so as to release glycerol from adipocytes and amino acid from muscle, resulting in the increase of substrate supplement. It has also been reported that glucocorticoid plays an important role in the differentiation of adipocyte precursors into mature adipocytes that can store triglyceride (Bujalska I J et al. 1999; Endocrinology 140, 3188-3196). This implies that the glucocorticoid induced by "stress" is deeply involved in the disease caused by abdominal obesity which is a major risk factor causing type II diabetes, hypertension, and coronary artery disease (Bjorntorp P & Rosmond R 2000; Int. J. Obesity 24, S80-S85).

It was experimentally confirmed that the activity of glucocorticoid could be controlled in tissue level not only by the secretion of cortisol but also by the intracellular interconversion between active cortisol and inactive cortisol mediated by 11β-HSD1 (11β-Hydroxysteroid dehydrogenase type 1) and 11β-HSD2 (11β-Hydroxysteroid dehydrogenase type 2) (Sandeep T C & Walker B R 2001 Trends in Endocrinol & Metab. 12, 446-453).

Glucocorticoid and 11β-HSD1 are known as important factors for the differentiation of adipocytes. The 11β-HSD1 mRNA level is increased in the visceral fat tissue of an obesity patient, compared with that in the subcutaneous tissue. The over-expression of 11β-HSD1 in the fat tissue of a transgenic mouse is related to the up-regulation of corticosterone in the fat tissue, visceral obesity, insulin sensitivity, type II diabetes, hyperlipidemia, and hyperphagia (H. Masuzaki et al (2001), Science, 294, 2166-2170). Thus, it can be said that 11β-HSD1 is mainly involved in visceral obesity and metabolic syndrome.

At this time, 11β-HSD1 converts the inactive glucocorticoid to the active form, suggesting that it plays an important role in activating glucocorticoid receptor in target tissues and in regulating the concentrations of glucocorticoid in there.

It has been confirmed that the above mechanism can be favorably used for the treatment of diabetes and obesity. Particularly, the treatment effect was confirmed when the antiulcerative agent carbenoxolone that can inhibit both 11β-HSD1 and 11β-HSD2 was used for the treatment. This treatment increased insulin sensitivity, and the suppressed 11β-HSD1 reduced intracellular cortisol level, suggesting that the insulin effect could be controlled (Walker B R et al. 1995; J. Clin. Endocrinol. Metab. 80, 3155-3159). The inhibition of 11β-HSD1 in the 11β-HSD1 knock-out mouse weakened the activity of gluconeogenesis enzyme to induce glucocorticoid and reduced the level of plasma glucose responding stress or obesity (Kotelevtsev Y. et al., Proc Natl Acad Sci USA. 1997 Dec. 23; 94 (26):14924-14929), indicating that the inhibition of 11β-HSD1 was effective in lowering plasma glucose and hepatic glucose in type II diabetes. The inhibition of 11β-HSD1 not only reduces the typical diabetes related symptoms but also does not carry any significant side effect.

In the course of study using the non-specific inhibitor carbenoxolone however, a side effect such as blood pressure increase was observed when 11β-HSD2 was inhibited. So, it is necessary to develop an inhibitor that has selectivity to 11β-HSD1.

Osteological development and bone function are also regulated by glucocorticoid. 11β-HSD1 exists in human osteoclasts and osteoblasts. When a healthy volunteer was treated with carbenoxolone, the bone formation marker showed no changes but the bone resorption marker was reduced (Cooper M S et al 2000; Bone 27, 375-381). The inhibition of 11β-HSD1 activity in bone can be used as a protective mechanism in the treatment of osteoporosis.

Further, glucocorticoid is also involved in eye disease like glaucoma. 11β-HSD1 has been known to affect the intraocular pressure in human, and thus the inhibition of 11β-HSD1 is expected to alleviate the increased intraocular pressure in relation to glaucoma (Rauz S et al. 2001; Investigative Ophthalmology & Visual Science 42, 2037-2042).

In the course of study to prepare compounds that can selectively inhibit 11β-HSD1, the present inventors succeeded in synthesizing novel compounds which showed excellent activity to inhibit 11β-HSD1 and to have plasma glucose lowering effect dose-dependently, which were confirmed by in vivo animal study. The present inventors completed this invention by confirming that the novel compounds synthesized by the inventors could be effectively used in the treatment of the following diseases or conditions; non-insulin dependent type II diabetes, insulin resistance, obesity, lipid disorder, metabolic syndrome, and other diseases mediated by the excessive activity of glucocorticoid.

SUMMARY OF THE INVENTION

It is an object of the present invention to provide a compound or a pharmaceutically acceptable salt thereof having the activity of inhibiting 11β-HSD1 enzyme.

It is another object of the present invention to provide a preparation method of the said compound.

It is also an object of the present invention to provide a pharmaceutical composition comprising the said compound or the pharmaceutically acceptable salt thereof as an active ingredient.

To achieve the above objects, the present invention provides a compound represented by formula 1 having the activity of inhibiting 11β-HSD1 enzyme or a pharmaceutically acceptable salt thereof:

[Formula 1]

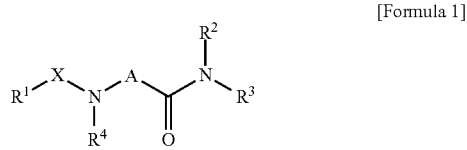

In formula 1,

X is carbonyl or sulfonyl;

$R^1$ is $C_{1-4}$ straight or branched alkyl, $C_{3-7}$ cycloalkyl, $C_{5-12}$ aryl, $C_{5-12}$ arylamine, 5-8 membered monocyclic or 8-12 membered bicyclic heterocycloalkyl, or 5-8 membered monocyclic or 8-12 membered bicyclic heteroaryl;

$R^2$ and $R^3$ are independently hydrogen, $C_{1-4}$ straight or branched alkyl, $C_{5-8}$ cycloalkyl, $C_{5-8}$ bicycloalkyl, $C_{5-8}$ aryl, 1-adamantyl, or 2-adamantyl, wherein the 1-adamantyl or 2-adamantyl is unsubstituted or substituted with one or more substituents selected from the group consisting of hydroxy, amino, aldehyde, hydroxy $C_{1-4}$ straight or branched alkyl, hydroxycarbonyl, aminocarbonyl, N-hydroxyaminocarbonyl, nitrile, hydroxycarbonyl $C_{1-4}$ straight or branched alkyl, aminocarbonyl $C_{1-4}$ straight or branched alkyl,

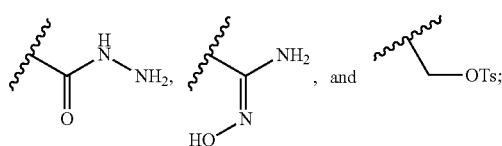 [SMILES: *C(=O)NN ; */C(N)=N\O ; *COS(=O)(=O)c1ccc(C)cc1]

$R^4$ is hydrogen, $C_{1-4}$ straight or branched alkyl, hydroxy $C_{1-4}$ straight or branched alkyl, or sodium;

A is

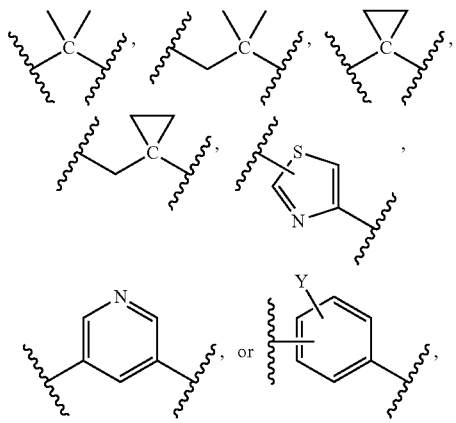

wherein Y is unsubstituted or halogen;

wherein the said $R^1$-$R^3$, the aryl is unsubstituted or substituted with one or more substituents selected from the group consisting of hydroxy, halogen, amino, $C_{1-4}$ straight or branched alkyl, $C_{1-4}$ straight or branched haloalkyl, $C_{1-4}$ straight or branched haloalkyloxy, $C_{1-4}$ straight or branched alkyloxy, $—O—Z^1—NZ^2Z^3$, $—O—NZ^2Z^3$, and $—Z^1—NZ^2Z^3$, wherein the $Z_1$ is $C_{1-4}$ straight or branched alkyl, and the $Z^2$ and $Z^3$ are independently hydrogen or $C_{1-4}$ straight or branched alkyl;

wherein the said $R^1$-$R^3$, the heterocycloalkyl or heteroaryl is monocyclic or bicyclic including one or more heteroatoms selected from the group consisting of oxygen, nitrogen and sulfur, wherein the heterocycloalkyl or heteroaryl is unsubstituted or substituted with one or more substituents selected from the group consisting of trifluoro $C_{1-4}$ straight or branched alkyl, pyrimidinyl, $C_{1-4}$ straight or branched alkyl, and $C_{1-4}$ straight or branched alkyloxycarbonyl, and also the heterocycloalkyl can be fused-bicyclic with $C_{5-12}$ aryl or heteroaryl, and also the heteroaryl can be fused-bicyclic with $C_{3-7}$ cycloalkyl or heterocycloalkyl;

wherein the $R^1$ and $R^4$ can form 5-8 membered monocyclic or 8-12 membered bicyclic heterocycloalkyl with X and N which are attached to the $R^1$ and $R^4$;

wherein the $R^4$ can form 5-8 membered monocyclic heterocycloalkyl with N and A which are attached to the $R^4$.

The present invention also provides a preparation method of the compound represented by formula 1 containing the step of reacting the compound represented by formula 2 with the compound represented by formula 3 to prepare the compound of formula 1, as represented in the following reaction formula 1.

[Reaction Formula 1]

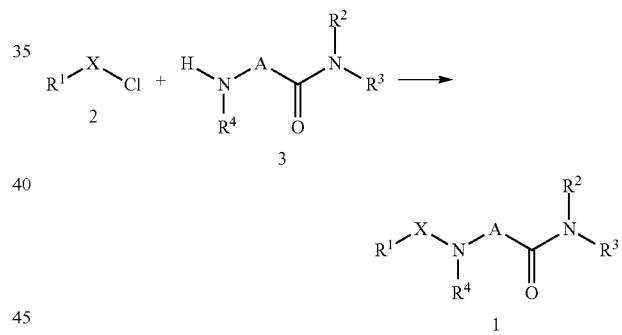

In reaction formula 1, $R^1$-$R^4$, X and A are as defined in formula 1.

In addition, the present invention provides a pharmaceutical composition for the prevention or treatment of diseases caused by the over-activation of 11β-HSD1 enzyme which comprises the compound represented by formula 1 or the pharmaceutically acceptable salt thereof as an active ingredient.

Advantageous Effect

As explained hereinbefore, the compounds of the present invention can be efficiently used as a therapeutic agent for the treatment of the disease or condition mediated by the over-activation of 11β-HSD1, such as non-insulin dependent type II diabetes, insulin resistance, obesity, lipid disorder, metabolic syndrome, and other diseases mediated by the excessive activity of glucocorticoid by selectively inhibiting the activity of 11β-HSD1 (11β-Hydroxysteroid dehydrogenase type 1).

DESCRIPTION OF THE PREFERRED EMBODIMENTS

Hereinafter, the present invention is described in detail.

The present invention provides a compound represented by formula 1 having the activity of inhibiting 11β-HSD1 enzyme or a pharmaceutically acceptable salt thereof.

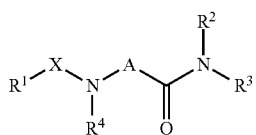

[Formula 1]

In formula 1,

X is carbonyl or sulfonyl;

$R^1$ is $C_{1-4}$ straight or branched alkyl, $C_{3-7}$ cycloalkyl, $C_{5-12}$ aryl, $C_{5-12}$ arylamine, 5-8 membered monocyclic or 8-12 membered bicyclic heterocycloalkyl, or 5-8 membered monocyclic or 8-12 membered bicyclic heteroaryl;

$R^2$ and $R^3$ are independently hydrogen, $C_{1-4}$ straight or branched alkyl, $C_{5-8}$ cycloalkyl, $C_{5-8}$ bicycloalkyl, $C_{5-8}$ aryl, 1-adamantyl, or 2-adamantyl, wherein the 1-adamantyl or 2-adamantyl is unsubstituted or substituted with one or more substituents selected from the group consisting of hydroxy, amino, aldehyde, hydroxy $C_{1-4}$ straight or branched alkyl, hydroxycarbonyl, aminocarbonyl, N-hydroxyaminocarbonyl, nitrile, hydroxycarbonyl $C_{1-4}$ straight or branched alkyl, aminocarbonyl $C_{1-4}$ straight or branched alkyl,

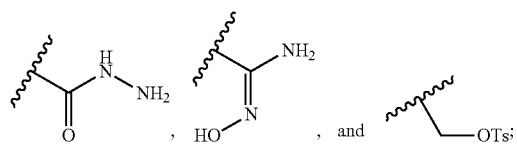 [SMILES: *C(=O)NN ; */C(N)=N\O ; *COS(=O)(=O)c1ccc(C)cc1]

$R^4$ is hydrogen, $C_{1-4}$ straight or branched alkyl, hydroxy $C_{1-4}$ straight or branched alkyl, or sodium;

A is

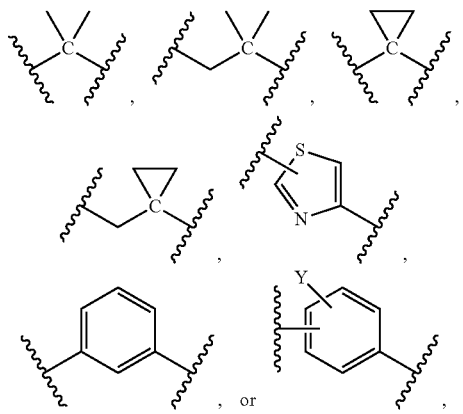

wherein Y is unsubstituted or halogen;

wherein the said $R^1$-$R^3$, the aryl is unsubstituted or substituted with one or more substituents selected from the group consisting of hydroxy, halogen, amino, $C_{1-4}$ straight or branched alkyl, $C_{1-4}$ straight or branched haloalkyl, $C_{1-4}$ straight or branched haloalkyloxy, $C_{1-4}$ straight or branched alkyloxy, —O—$Z^1$—$NZ^2Z^3$, —O—$NZ^2Z^3$, and —$Z^1$—$NZ^2Z^3$, wherein the $Z_1$ is $C_{1-4}$ straight or branched alkyl, and the $Z^2$ and $Z^3$ are independently hydrogen or $C_{1-4}$ straight or branched alkyl;

wherein the said $R^1$-$R^3$, the heterocycloalkyl or heteroaryl is monocyclic or bicyclic including one or more heteroatoms selected from the group consisting of oxygen, nitrogen and sulfur, wherein the heterocycloalkyl or heteroaryl is unsubstituted or substituted with one or more substituents selected from the group consisting of trifluoro $C_{1-4}$ straight or branched alkyl, pyrimidinyl, $C_{1-4}$ straight or branched alkyl, and $C_{1-4}$ straight or branched alkyloxycarbonyl, and also the heterocycloalkyl can be fused-bicyclic with $C_{5-12}$ aryl or heteroaryl, and also the heteroaryl can be fused-bicyclic with $C_{3-7}$ cycloalkyl or heterocycloalkyl;

wherein the $R^1$ and $R^4$ can form 5-8 membered monocyclic or 8-12 membered bicyclic heterocycloalkyl with X and N which are attached to the $R^1$ and $R^4$;

wherein the $R^4$ can form 5-8 membered monocyclic heterocycloalkyl with N and A which are attached to the $R^4$.

Preferably,

X is carbonyl or sulfonyl;

$R^1$ is $C_{1-4}$ straight or branched alkyl, $C_{3-7}$ cycloalkyl, $C_{5-6}$ aryl, $C_{5-6}$ arylamine, 5-6 membered monocyclic or 9-10 membered bicyclic heterocycloalkyl, or 5-6 membered monocyclic or 9-10 membered bicyclic heteroaryl;

$R^2$ and $R^3$ are independently hydrogen, methyl, ethyl, propyl, $C_{6-7}$ cycloalkyl, $C_{6-8}$ bicycloalkyl, $C_{5-6}$ aryl, 1-adamantyl, or 2-adamantyl, wherein the 1-adamantyl or 2-adamantyl is unsubstituted or substituted with one or more substituents selected from the group consisting of hydroxy, amino, aldehyde, hydroxymethyl, hydroxyethyl, hydroxycarbonyl, aminocarbonyl, N-hydroxyaminocarbonyl, nitrile, hydroxycarbonylmethyl, hydroxycarbonylethyl, aminocarbonylmethyl, aminocarbonylethyl,

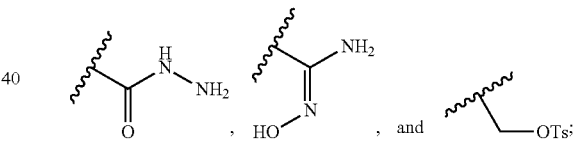

$R^4$ is hydrogen, methyl, ethyl, propyl, hydroxy methyl, hydroxyethyl, or sodium;

A is

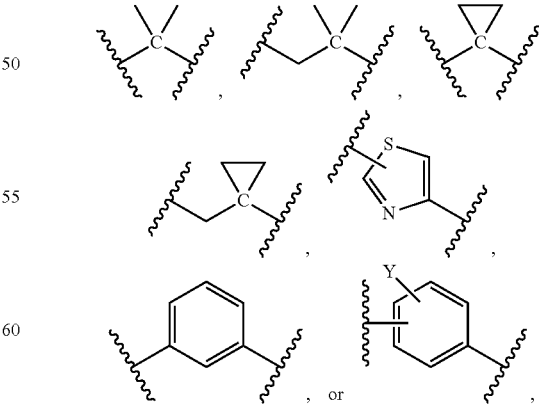

wherein Y is Cl or F;

wherein the said $R^1$-$R^3$, the aryl is unsubstituted or substituted with one or more substituents selected from the group consisting of halogen, trifluoromethyl, trifluoroethyl, trifluoromethyloxy, trifluoroethyloxy, methyloxy, ethyloxy, propyloxy, methyl, ethyl, 1,1,1-trifluoro-2-ol-isopropyl, —O(CH$_2$)$_n$NZ$^2$Z$^3$, and —(CH$_2$)$_n$NZ$^2$Z$^3$, the n is 1 or 2, and the Z$^2$ and Z$^3$ are independently hydrogen, methyl or ethyl;

wherein the said R$^1$-R$^3$, the heterocycloalkyl or heteroaryl contains one or more heteroatoms selected from the group consisting of oxygen, nitrogen and sulfur, wherein the heterocycloalkyl or heteroaryl is unsubstituted or substituted with one or more substituents selected from the group consisting of trifluoromethyl, trifluoroethyl, pyrimidinyl, methyl, ethyl, and isobutyloxycarbonyl, and also the heterocycloalkyl can be fused-bicyclic with C$_{5-12}$ aryl or heteroaryl, and also the heteroaryl can be fused-bicyclic with C$_{3-7}$ cycloalkyl or heterocycloalkyl;

wherein the R$^1$ and R$^4$ can form 5-6 membered monocyclic or 8-9 membered bicyclic heterocycloalkyl with X and N which are attached to the R$^1$ and R$^4$;

R$^4$ can form 5-6 membered monocyclic heterocycloalkyl with N and A which are attached to the R$^4$.

More preferably,
X is carbonyl or sulfonyl,
R$^1$ is

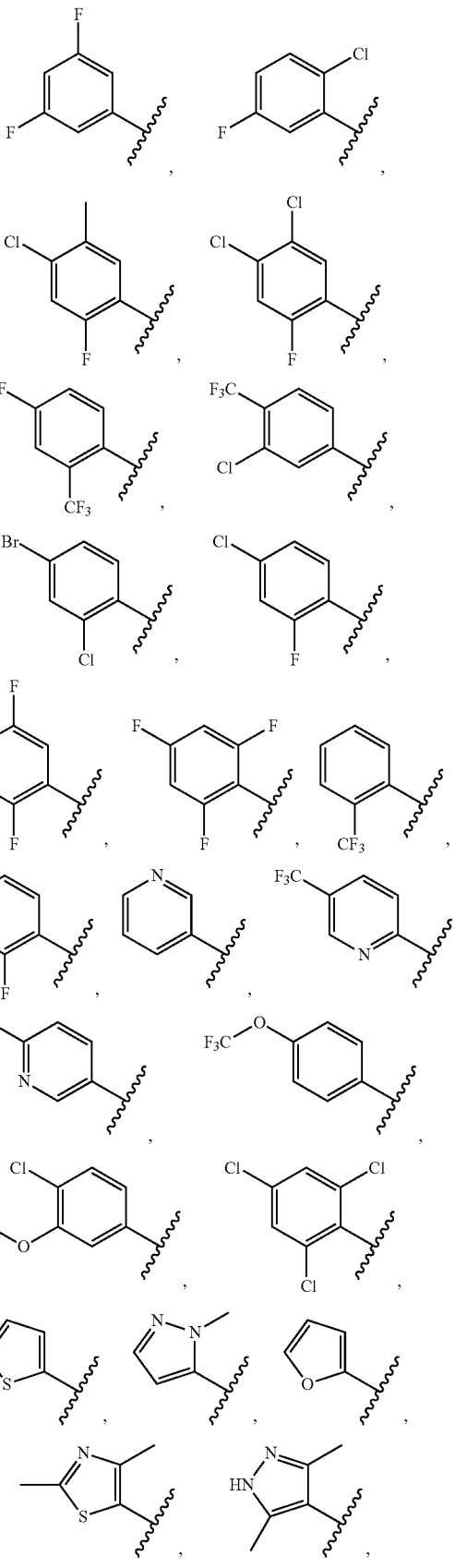

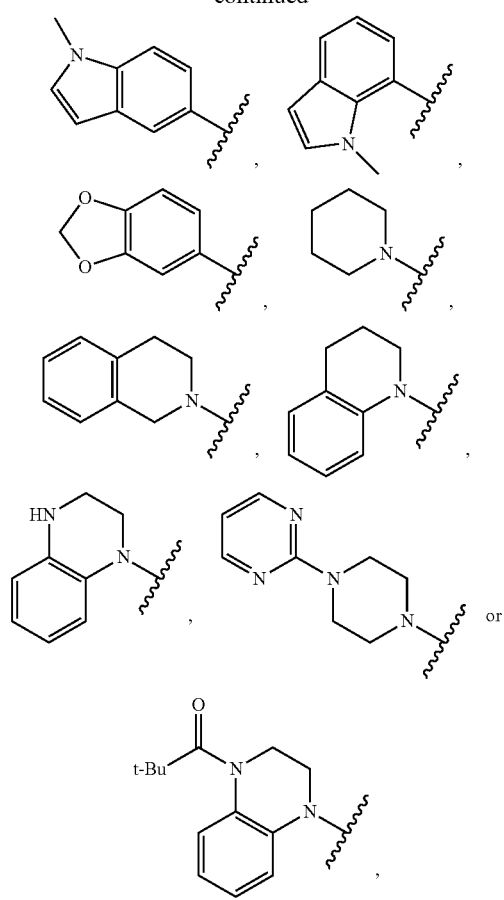
$R^2$ is —H or —$(CH_2)_2CH_3$,
$R^3$ is
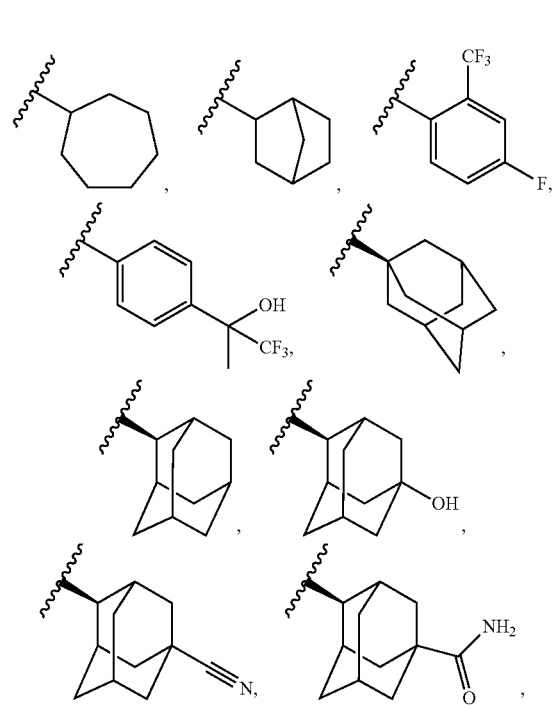
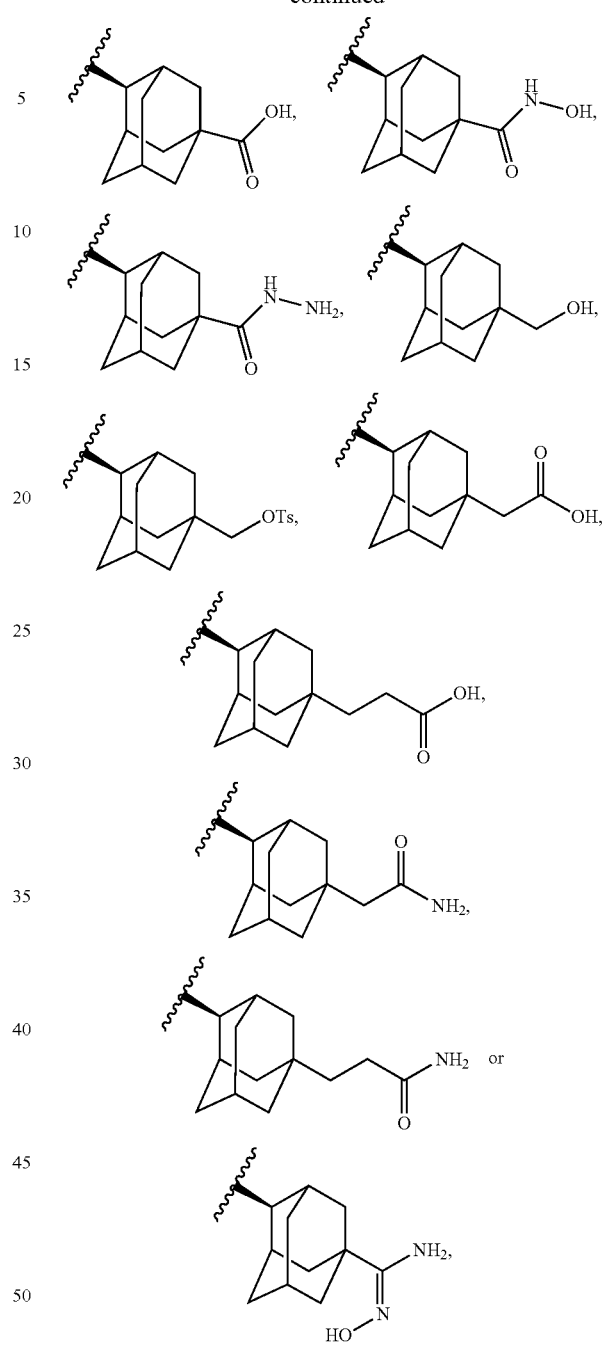
$R^4$ is —H, —$CH_3$, —$CH_2CH_3$, —$CH_2CH_2OH$, or —Na,
A is
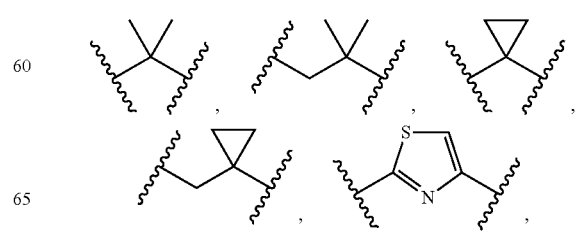

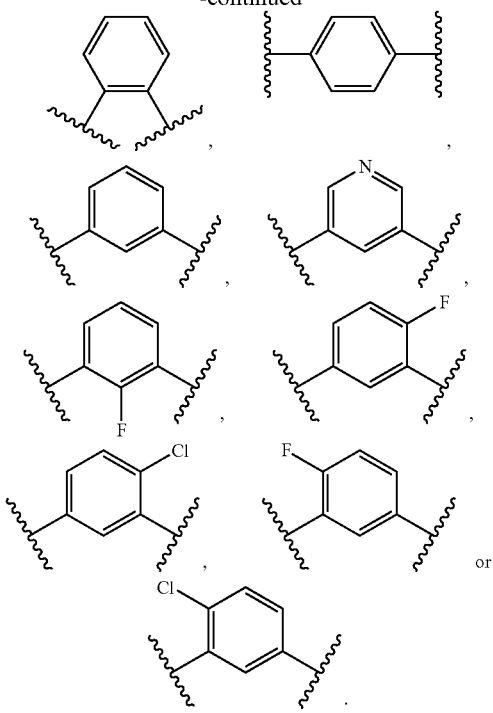

More preferably,
X is sulfonyl;
R¹ is phenyl, wherein the phenyl is unsubstituted or substituted with one or more substituents selected from the group consisting of halogen and trifluoromethyl, and the halogen can be substituted with one or more;
$R^2$ is —H or —CH$_3$;
$R^3$ is

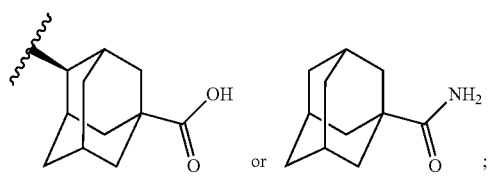

$R^4$ is —H,
A is

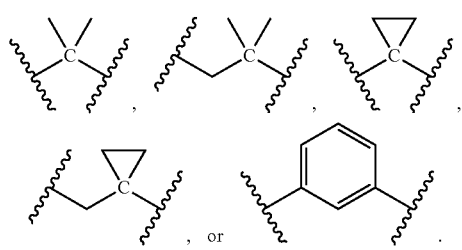

More preferably,
X is sulfonyl;
R¹ is phenyl, wherein the phenyl is unsubstituted or substituted with one or more substituents selected from the group consisting of halogen and trifluoromethyl, and the halogen can be substituted with one or more;
$R^2$ is —H;
$R^3$ is

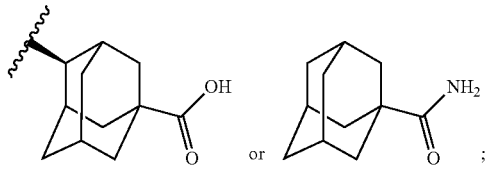

$R^4$ is —H or —Na,
A is

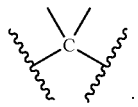 [SMILES: *C(*)(C)C]

More preferably,
X is sulfonyl;
R¹ is phenyl, wherein the phenyl is unsubstituted or substituted with one or more substituents selected from the group consisting of halogen and trifluoromethyl, and the halogen can be substituted with one or more;
$R^2$ is —H;
$R^3$ is

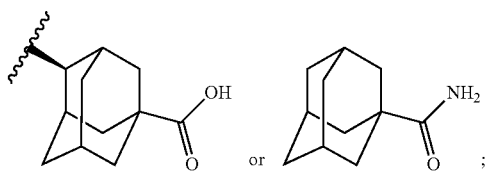

$R^4$ is —H or —Na,
A is

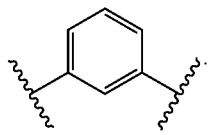

Specific examples of the compound represented by formula 1 of the present invention are as follows:

(1) N-(adamantan-2-yl)-1-[(3-chloro-2-methylbenzenesulfonylamino)methyl]cyclopropanecarboxamide;
(2) (1-[(2-fluoro-benzenesulfonylamino)methyl]-N-(5-hydroxyadamantan-2-yl)cyclopropanecarboxamide;
(3) E-4-[1-((2-fluoro-benzenesulfonylamino)methyl)cyclopropanecarboxamido]-adamantan-1-carboxylic acid amide;
(4) Z-4-[1-((2-fluoro-benzenesulfonylamino)methyl)cyclopropanecarboxamido]-adamantan-1-carboxylic acid amide;
(5) E-4-[1-((3-chloro-2-methyl-benzenesulfonylamino)methyl)cyclopropanecarboxamido]-adamantan-1-carboxylic acid amide;
(6) Z-4-[1-((3-chloro-2-methyl-benzenesulfonylamino)methyl)cyclopropanecarboxamido]-adamantan-1-carboxylic acid amide;

(7) E-4-[1-((3-chloro-benzenesulfonylamino)methyl)cyclopropanecarboxamido]-adamantan-1-carboxylic acid amide;
(8) E-4-[1-((3-chloro-2-fluoro-benzenesulfonylamino)methyl)cyclopropanecarboxamido]-adamantan-1-carboxylic acid amide;
(9) E-4-[1-((3,5-difluoro-benzenesulfonylamino)methyl)cyclopropanecarboxamido]-adamantan-1-carboxylic acid amide;
(10) E-4-[1-((2-fluoro-6-methyl-benzenesulfonylamino)methyl)cyclopropanecarboxamido]-adamantan-1-carboxylic acid amide;
(11) E-4-[1-((2,3-difluoro-benzenesulfonylamino)methyl)cyclopropanecarboxamido]-adamantan-1-carboxylic acid amide;
(12) E-4-[1-((2,4,6-trifluoro-benzenesulfonylamino)methyl)cyclopropanecarboxamido]-adamantan-1-carboxylic acid amide;
(13) E-4-[1-((2-fluoro-N,6-dimethyl-benzenesulfonylamino)methyl)cyclopropanecarboxamido]-adamantan-1-carboxylic acid amide;
(14) E-4-[1-((2,4-dichloro-5-methyl-benzenesulfonylamino)methyl)cyclopropanecarboxamido]-adamantan-1-carboxylic acid amide;
(15) E-4-[1-((4-chloro-2-fluoro-5-methyl-benzenesulfonylamino)methyl)cyclopropanecarboxamido]-adamantan-1-carboxylic acid amide;
(16) E-4-[1-((4,5-dichloro-2-fluoro-benzenesulfonylamino)methyl)cyclopropanecarboxamido]-adamantan-1-carboxylic acid amide;
(17) E-4-[1-((furan-2-sulfonylamino)methyl)cyclopropanecarboxamido]-adamantan-1-carboxylic acid amide;
(18) E-4-[1-(3,5-dichloro-benzenesulfonylamino)methyl)cyclopropanecarboxamido]-adamantan-1-carboxylic acid amide;
(19) E-4-[1-((thiophen-2-sulfonylamino)methyl)cyclopropanecarboxamido]-adamantan-1-carboxylic acid amide;
(20) E-4-[1-((2-(trifluoromethyl)-4-fluoro-benzenesulfonylamino)methyl)cyclopropanecarboxamido]-adamantan-1-carboxylic acid amide;
(21) E-4-[1-((3,4-difluoro-benzenesulfonylamino)methyl)cyclopropanecarboxamido]-adamantan-1-carboxylic acid amide;
(22) E-4-[1-((2-fluoro-N-methyl-benzenesulfonylamino)methyl)cyclopropanecarboxamido]-adamantan-1-carboxylic acid amide;
(23) E-4-[1-((4-trifluoromethoxy-benzenesulfonylamino)methyl)cyclopropanecarboxamido]-adamantan-1-carboxylic acid amide;
(24) E-4-[1-((2,3-difluoro-benzeneamino)methyl)cyclopropanecarboxamido]-adamantan-1-carboxylic acid amide;
(25) E-4-[1-((3,4-difluoro-benzeneamino)methyl)cyclopropanecarboxamido]-adamantan-1-carboxylic acid amide;
(26) E-4-[1-((1-methyl-1H-indole-5-sulfonylamino)methyl)cyclopropanecarboxamido]-adamantan-1-carboxylic acid amide;
(27) E-4-[1-((1-methyl-1H-pyrazole-5-sulfonylamino)methyl)cyclopropanecarboxamido]-adamantan-1-carboxylic acid amide;
(28) E-4-[1-((benzenesulfonylamino)methyl)cyclopropanecarboxamido]-adamantan-1-carboxylic acid amide;
(29) E-4-[1-((2-fluoro-benzenesulfonylamino)methyl)cyclopropanecarboxamido]-adamantan-1-carboxylic acid amide;
(30) N-(bicyclo[2.2.1]heptan-2-yl)-1-((2-fluoro-N-methyl-benzenesulfonylamino)methyl)cyclopropanecarboxamido;
(31) N-(adamantan-1-yl)-1-((2-fluoro-N-methylbenzenesulfonylamino)methyl)cyclopropanecarboxamido;
(32) E-4-[1-((N-ethyl-fluoro-benzenesulfonylamino)methyl)cyclopropanecarboxamido]-adamantan-1-carboxylic acid amide;
(33) E-3-(4-(1((2-fluoro-benzenesulfonylamino)methyl)cyclopropanecarboxamido)adamantan-1-yl)propanoic acid;
(34) E-N-(5-(3-amino-3-oxopropyl)adamantan-2-yl)-1-((2-fluoro-benzenesulfonylamino)methyl)cyclopropanecarboxamide;
(35) E-N-(5-aminoadamantan-2-yl)-1-((2-fluoro-benzenesulfonylamino)methyl)cyclopropanecarboxamide hydrochloride;
(36) E-4-[1-((2,4,5-trifluoro-benzenesulfonylamino)methyl)cyclopropanecarboxamido]-adamantan-1-carboxylic acid amide;
(37) E-4-[1-((4-chloro-benzenesulfonylamino)methyl)cyclopropanecarboxamido]-adamantan-1-carboxylic acid amide;
(38) E-4-[1-(3-chloro-benzenesulfonylamino)cyclopropanecarboxamido]-adamantan-1-carboxylic acid amide;
(39) E-4-[1-(2-fluoro-benzenesulfonylamino)cyclopropanecarboxamido]-adamantan-1-carboxylic acid amide;
(40) E-4-[1-(2-fluoro-6-methyl-benzenesulfonylamino)cyclopropanecarboxamido]-adamantan-1-carboxylic acid amide;
(41) E-4-[1-(3-chloro-2-methyl-benzenesulfonylamino)cyclopropanecarboxamido]-adamantan-1-carboxylic acid amide;
(42) E-4-[1-(4-fluoro-benzenesulfonylamino)cyclopropanecarboxamido]-adamantan-1-carboxylic acid amide;
(43) E-4-[1-(2,4-dichloro-5-methyl-benzenesulfonylamino)cyclopropanecarboxamido]-adamantan-1-carboxylic acid amide;
(44) E-4-[1-(2,4-difluorochloro-benzenesulfonylamino)cyclopropanecarboxamido]-adamantan-1-carboxylic acid amide;
(45) E-4-[1-(2-fluoro-4,5-dichloro-benzenesulfonylamino)cyclopropanecarboxamido]-adamantan-1-carboxylic acid amide;
(46) E-4-[1-(2-fluoro-4-chloro-5-methyl-benzenesulfonylamino)cyclopropanecarboxamido]-adamantan-1-carboxylic acid amide;
(47) E-4-[1-(2,3,4-trifluoro-benzenesulfonylamino)cyclopropanecarboxamido]-adamantan-1-carboxylic acid amide;
(48) E-4-[1-(thiophen-2-sulfonylamino)cyclopropanecarboxamido]-adamantan-1-carboxylic acid amide;
(49) E-4-[3-(6-trifluoromethyl-pyridin-2-sulfonylamino)cyclopropanecarboxamido]-adamantan-1-carboxylic acid amide;
(50) E-4-[1-(1-methyl-1H-indole-7-sulfonylamino)cyclopropanecarboxamido]-adamantan-1-carboxylic acid amide;
(51) 1-(3-chloro-benzenesulfonylamino)-N-(4-fluoro-2-(trifluoromethyl)phenyl)cyclopropanecarboxamide;
(52) E-4-[1-(3-chloro-benzenesulfonylamino)cyclopropanecarboxamido]-N-hydroxyadamantan-1-carboxylic acid amide;
(53) 1-(3-chloro-benzenesulfonylamino)-N-[4-(1,1,1-trifluoro-2-hydroxypropan-2-yl)phenyl]cyclopropanecarboxamide;
(54) E-4-[1-(3-chloro-benzeneamino)cyclopropanecarboxamido]-adamantan-1-carboxylic acid amide;
(55) N-(bicyclo[2.2.1]heptan-2-yl)-1-(3-chloro-benzenesulfonylamino)cyclopropanecarboxamide;

(56) E-4-[1-(1,1-dioxydobenzo[d]isothiazol-2(3H)-yl)cyclopropanecarboxamido]adamantan-1-carboxylic acid amide;
(57) E-4-[1-(3,4-difluoro-benzeneamino)cyclopropanecarboxamido]-adamantan-1-carboxylic acid amide;
(58) E-4-[1-(1-methyl-1H-pyrazole-5-sulfonylamino)cyclopropanecarboxamido]-adamantan-1-carboxylic acid amide;
(59) E-4-[1-(2,3-difluoro-benzeneamino)cyclopropanecarboxamido]-adamantan-1-carboxylic acid amide;
(60) E-4-[1-(benzenesulfonylamino)cyclopropanecarboxamido]-N-hydroxyadamantan-1-carboxylic acid amide;
(61) E-4-[1-(2-fluoro-N-methylbenzenesulfonylamino)cyclopropanecarboxamido]-adamantan-1-carboxylic acid amide;
(62) E-4-[1-(3-chloro-N-methylbenzenesulfonylamino)cyclopropanecarboxamido]-adamantan-1-carboxylic acid amide;
(63) E-4-[1-(2-fluorobenzamido)cyclopropanecarboxamido]-adamantan-1-carboxylic acid amide;
(64) E-N-[1-(5-carbamoyladamantan-2-yl)carbamoyl)cyclopropyl)-5-(trifluoromethyl)pyrrolineamide;
(65) E-4-(1-(benzo[d][1,3]dioxol-5-sulfonylamino)cyclopropanecarboxamino)adamantan-1-carboxylic acid amide;
(66) 1-(3-chloro-benzenesulfonylamino)-N-cycloheptyl-N-propylcyclopropanecarboxamide;
(67) E-4-(3-(3-chloro-benzenesulfonylamino)-2,2-dimethylpropanamido)adamantan-1-carboxylic acid amide;
(68) E-4-[3-(2-fluoro-benzenesulfonylamino)-2,2-dimethylpropanamido]adamantan-1-carboxylic acid amide;
(69) E-4-[3-(benzenesulfonylamino)-2,2-dimethylpropanamido]adamantan-1-carboxylic acid amide;
(70) E-4-[3-(3-chloro-2-methyl-benzenesulfonylamino)-2,2-dimethylpropanamido]adamantan-1-carboxylic acid amide;
(71) E-4-[2-(2-fluoro-benzenesulfonylamino)-2-methylpropanamido]-adamantan-1-carboxylic acid amide;
(72) E-4-[2-(2-fluoro-N-methyl-benzenesulfonylamino)-2-methylpropanamido]adamantan-1-carboxylic acid amide;
(73) E-4-[2-(3-chlorobenzenesulfonylamino)-2-methylpropanamido]adamantan-1-carboxylic acid amide;
(74) E-N-(5-cyanoadamantan-2-yl)-2-(2-fluoro-benzenesulfonylamino)-2-methylpropanamide;
(75) E-2-(2-fluoro-benzenesulfonylamino)-N-[5-(N'-carbamimidoyl)adamantan-2-yl]-2-methylpropanamide;
(76) E-2-(2-fluoro-benzenesulfonylamino)-N-[5-(hydroxymethyl)adamantan-2-yl]-2-methylpropanamide;
(77) E-2-(2-fluoro-benzenesulfonylamino)-N-(5-formyladamantan-2-yl)-2-methylpropanamide;
(78) E-[4-(2-(2-fluoro-benzenesulfonylamino)-2-methylpropanamido)adamantan-1-yl]methyl-4-methylbenzenesulfonate;
(79) E-2-[4-(2-(2-fluorobenzenesulfonylamino)-2-methylpropanamido)adamantan-1-yl]acetic acid;
(80) E-N-[5-(2-amino-2-oxoethyl)adamantan-2-yl]-2-(2-fluorobenzenesulfonylamino)-2-methylpropanamide;
(81) E-4-[2-methyl-2-(benzenesulfonylamino)propanamido]adamantan-1-carboxylic acid amide;
(82) E-4-[2-(2-fluoro-3-chloro-benzenesulfonylamino)-2-methylpropanamido]adamantan-1-carboxylic acid amide;
(83) E-4-[2-(3,5-difluoro-benzenesulfonylamino)-2-methylpropanamido]adamantan-1-carboxylic acid amide;
(84) E-4-[2-(2,6-difluoro-benzenesulfonylamino)-2-methylpropanamido]adamantan-1-carboxylic acid amide;
(85) E-2-(2-fluoro-benzenesulfonylamino)-N-(5-(hydrazinecarbonyl)adamantan-2-yl)-2-methylpropanamide;
(86) E-N-(5-(3-amino-3-oxopropyl)adamantan-2-yl)-2-(2-fluoro-benzenesulfonylamino)-2-methylpropanamide;
(87) E-2-(2-fluoro-benzenesulfonylamino)-N-(5-(hydrazinecarbonyl)adamantan-2-yl)-2-methylpropanamide;
(88) E-4-[2-(4-chloro-benzenesulfonylamino)-2-methylpropanamido]adamantan-1-carboxylic acid amide;
(89) E-4-[2-(2,5-dichloro-benzenesulfonylamino)-2-methylpropanamido]adamantan-1-carboxylic acid amide;
(90) 2-(3-chloro-benzenesulfonylamino)-N-cycloheptyl-2-methyl-N-propylpropanamide;
(91) E-4-[3-(2-fluoro-benzenesulfonylamino)-benzamido]-adamantan-1-carboxylic acid amide;
(92) E-4-[2-(2-fluoro-benzenesulfonylamino)-benzamido]-adamantan-1-carboxylic acid amide;
(93) E-4-[4-(2-fluoro-benzenesulfonylamino)-benzamido]-adamantan-1-carboxylic acid amide;
(94) E-4-[3-(4-fluoro-benzenesulfonylamino)-benzamido]-adamantan-1-carboxylic acid amide;
(95) E-4-[3-(3-chloro-benzenesulfonylamino)-benzamido]-adamantan-1-carboxylic acid amide;
(96) E-4-[3-(3-chloro-2-methyl-benzenesulfonylamino)-benzamido]-adamantan-1-carboxylic acid amide;
(97) E-4-[3-[(3-chloro-benzenesulfonyl)-methylamino]-benzamido]-adamantan-1-carboxylic acid amide;
(98) E-4-[3-N-(2-hydroxyethyl)-2-(trifluoromethyl-benzenesulfonylamino)benzamido]-adamantan-1-carboxylic acid amide;
(99) E-4-(3-[(2-trifluoromethyl-benzenesulfonyl)-methylamino]-benzamido)-adamantan-1-carboxylic acid amide;
(100) E-sodium[3-((5-carbamoyladamantan-2-yl)carbamoyl)phenyl](2-(trifluoromethyl)benzenesulfonylamide;
(101) E-N-(5-carbamoyladamantan-2-yl)-5-[(N-methyl-2-(trifluoromethyl)benzenesulfonylamino]nicotinamide;
(102) E-4-[3-(thiophen-2-sulfonylamino)-benzamido]-adamantan-1-carboxylic acid amide;
(103) E-4-[3-(furan-2-sulfonylamino)-benzamido]-adamantan-1-carboxylic acid amide;
(104) E-4-[3-(pyridin-3-sulfonylamino)-benzamido]-adamantan-1-carboxylic acid amide;
(105) E-4-(3-(benzenesulfonylamino-benzamido)-adamantan-1-carboxylic acid amide;
(106) E-4-[3-[(2-chloro-benzenesulfonylamino]benzamido]-adamantan-1-carboxylic acid amide;
(107) E-4-[3-[(2,4-dimethyl-thiazol-5-sulfonylamino)-benzamido]-adamantan-1-carboxylic acid amide;
(108) E-4-[3-(3,5-dimethyl-1H-pyrazole-4-sulfonylamino)-benzamido]-adamantan-1-carboxylic acid amide;
(109) E-N-(5-hydroxy-adamantan-2-yl)-3-benzenesulfonylamino-benzamide;
(110) E-N-cycloheptyl-3-phenylsulfamoyl-benzamide;
(111) E-N-(5-hydroxyadamantan-2-yl)-3-(2-(trifluoromethyl)benzenesulfonylamino)benzamide;
(112) E-4-(3-(N-phenylsulfamoylbenzamino)-adamantan-1-carboxylic acid amide;
(113) E-sodium[3-((5-carbamoyladamantan-2-yl)carbamoyl)phenyl]-2-fluoro-3-chloro-benzenesulfonylamide;
(114) E-4-[3-(3-chloro-4-(trifluoromethyl)benzene sulfonylamino)benzamido]adamantan-1-carboxylic acid amide;
(115) E-4-[3-[(2-(trifluoromethyl)benzenesulfonylamino]-benzamido]-adamantan-1-carboxylic acid amide;
(116) E-4-[3-(2-chloro-4-bromo-benzenesulfonylamino)-benzamido]-adamantan-1-carboxylic acid amide;
(117) E-4-[3-(2,4,6-trichloro-benzenesulfonylamino)-benzamido]-adamantan-1-carboxylic acid amide;
(118) E-4-[3-(3-chloro-5-fluoro-benzenesulfonylamino)-benzamido]-adamantan-1-carboxylic acid amide;

(119) E-4-[3-(3,5-dichloro-benzenesulfonyamino)-benzamido]-adamantan-1-carboxylic acid amide;
(120) E-4-[3-(3-fluoro-benzenesulfonylamino)-benzamido]-adamantan-1-carboxylic acid amide;
(121) E-4-[3-(2,4-difluoro-benzenesulfonylamino)-benzamido]-adamantan-1-carboxylic acid amide;
(122) E-4-[3-(2,5-difluoro-benzenesulfonylamino)-benzamido]-adamantan-1-carboxylic acid amide;
(123) E-4-[3-(2,6-difluoro-benzenesulfonylamino)-benzamido]-adamantan-1-carboxylic acid amide;
(124) E-N-cycloheptyl-N-propyl-3-(2-(trifluoromethyl)benzenesulfonylamino)benzamide;
(125) E-4-[2-fluoro-3-(2-(trifluoromethyl)benzenesulfonylamino)benzamido]adamantan-1-carboxylic acid amide;
(126) E-4-[2-chloro-5-(3-chloro-benzenesulfonylamino)benzamido]adamantan-1-carboxylic acid amide;
(127) E-4-[3-(3-chlorobenzenesulfonylamino)-4-fluorobenzamido]adamantan-1-carboxylic acid amide;
(128) E-4-[4-chloro-3-(3,5-dichlorobenzenesulfonylamino)benzamido]adamantan-1-carboxylic acid amide;
(129) E-4-[2-chloro-5-(3,5-dichlorobenzenesulfonylamino)benzamido]adamantan-1-carboxylic acid amide;
(130) E-4-[3-(3,5-dichlorobenzenesulfonylamino)-4-fluorobenzamido]adamantan-1-carboxylic acid amide;
(131) E-4-[5-(3,5-dichlorobenzenesulfonylamino)-2-fluorobenzamido]adamantan-1-carboxylic acid amide;
(132) E-4-[2-fluoro-3-(3-chlorobenzenesulfonylamino)benzamido]adamantan-1-carboxylic acid amide;
(133) E-4-[2-chloro-5-(3-chloro-4-methoxybenzenesulfonylamino)benzamido]adamantan-1-carboxylic acid amide;
(134) E-4-[4-chloro-3-(3-chloro-4-methoxybenzenesulfonylamino)benzamido]adamantan-1-carboxylic acid amide;
(135) E-4-[5-(3-chloro-4-methoxybenzenesulfonylamino)-2-fluorobenzamido]adamantan-1-carboxylic acid amide;
(136) E-4-(3-(4-chloro-benzenesulfonylamino-benzamido)-adamantan-1-carboxylic acid amide;
(137) E-4-(3-(4-chloro-benzenesulfonylamino-benzamido)-adamantan-1-carboxylic acid amide;
(138) E-4-(3-(cyclopropanesulfonamido)benzamido)adamantan-1-carboxylic acid amide;
(139) E-4-(3-(1-methylethylsulfonamido)benzamido)adamantan-1-carboxylic acid amide;
(140) E-[3,4-dihydro-1H-isoquinolin-2-carboxylic acid-1-[(5-carbamoyl-adamantan-2-ylcarbamoyl)cyclopropylmethyl]-amide;
(141) E-3,4-dihydro-2H-quinolin-1-carboxylic acid[1-(5-carbamoyl-adamantan-2-ylcarbamoyl)-cyclopropylmethyl]-amide;
(142) E-piperidin-1-carboxylic acid[1-(5-carbamoyl-adamantan-2-ylcarbamoyl)-cyclopropylmethyl]-amide;
(143) E-4-([1-5-carbamoyl-adamantan-2-ylcarbamoyl)-cyclopropylmethyl]-carbamoyl)-3,4-dihydro-2H-quinolin-1carboxylic acid-butylester;
(144) E-4-Pyrimidin-2-yl-piperazin-1-carboxylic acid[1-(5-carbamoyl-adamantan-2-ylcarbamoyl)-cyclopropylmethyl]-amide;
(145) E-4-((1[(3-phenyl-ureido)methyl]-cyclopropanecarbonyl)amino)-adamantan-1carboxylic acid amide;
(146) E-3,4-dihydro-2H-quinoxalin-1-carboxylic acid[1-(5-carbamoyl-adamantan-2-ylcarbamoyl)-cyclopropylmethyl]-amide;
(147) E-3,4-dihydro-1H-isoquinolin-2-carboxylic acid[4-(5-carbamoyl-adamantan-2-ylcarbamoyl)-thiazol-2-yl]-amide;
(148) E-3,4-dihydro-2H-quinolin-1-carboxylic acid[4-(5-carbamoyl-adamantan-2-ylcarbamoyl)-thiazol-2-yl]-amide; and
(149) E-2-(2-fluoro-benzamido)-thiazol-4-carboxylic acid (5-carbamoyl-adamantan-2-yl)amide.

Preferable examples of the compound represented by formula 1 of the present invention are as follows:

(1) N-(adamantan-2-yl)-1-[(3-chloro-2-methylbenzenesulfonylamino)methyl]cyclopropanecarboxamide;
(2) (1-[(2-fluoro-benzenesulfonylamino)methyl]-N-(5-hydroxyadamantan-2-yl)cyclopropanecarboxamide;
(3) E-4-[1-((2-fluoro-benzenesulfonylamino)methyl)cyclopropanecarboxamido]-adamantan-1-carboxylic acid amide;
(4) Z-4-[1-((2-fluoro-benzenesulfonylamino)methyl)cyclopropanecarboxamido]-adamantan-1-carboxylic acid amide;
(5) E-4-[1-((3-chloro-2-methyl-benzenesulfonylamino)methyl)cyclopropanecarboxamido]-adamantan-1-carboxylic acid amide;
(6) Z-4-[1-((3-chloro-2-methyl-benzenesulfonylamino)methyl)cyclopropanecarboxamido]-adamantan-1-carboxylic acid amide;
(7) E-4-[1-((3-chloro-benzenesulfonylamino)methyl)cyclopropanecarboxamido]-adamantan-1-carboxylic acid amide;
(8) E-4-[1-((3-chloro-2-fluoro-benzenesulfonylamino)methyl)cyclopropanecarboxamido]-adamantan-1-carboxylic acid amide;
(9) E-4-[1-((3,5-difluoro-benzenesulfonylamino)methyl)cyclopropanecarboxamido]-adamantan-1-carboxylic acid amide;
(10) E-4-[1-((2-fluoro-6-methyl-benzenesulfonylamino)methyl)cyclopropanecarboxamido]-adamantan-1-carboxylic acid amide;
(11) E-4-[1-((2,3-difluoro-benzenesulfonylamino)methyl)cyclopropanecarboxamido]-adamantan-1-carboxylic acid amide;
(12) E-4-[1-((2,4,6-trifluoro-benzenesulfonylamino)methyl)cyclopropanecarboxamido]-adamantan-1-carboxylic acid amide;
(13) E-4-[1-((2-fluoro-N,6-dimethyl-benzenesulfonylamino)methyl)cyclopropanecarboxamido]-adamantan-1-carboxylic acid amide;
(14) E-4-[1-((2,4-dichloro-5-methyl-benzenesulfonylamino)methyl)cyclopropanecarboxamido]-adamantan-1-carboxylic acid amide;
(15) E-4-[1-((4-chloro-2-fluoro-5-methyl-benzenesulfonylamino)methyl)cyclopropanecarboxamido]-adamantan-1-carboxylic acid amide;
(16) E-4-[1-((4,5-dichloro-2-fluoro-benzenesulfonylamino)methyl)cyclopropanecarboxamido]-adamantan-1-carboxylic acid amide;
(17) E-4-[1-((furan-2-sulfonylamino)methyl)cyclopropanecarboxamido]-adamantan-1-carboxylic acid amide;
(18) E-4-[1-(3,5-dichloro-benzenesulfonylamino)methyl)cyclopropanecarboxamido]-adamantan-1-carboxylic acid amide;
(19) E-4-[1-((thiophen-2-sulfonylamino)methyl)cyclopropanecarboxamido]-adamantan-1-carboxylic acid amide;
(20) E-4-[1-((2-(trifluoromethyl)-4-fluoro-benzenesulfonylamino)methyl)cyclopropanecarboxamido]-adamantan-1-carboxylic acid amide;
(21) E-4-[1-((3,4-difluoro-benzenesulfonylamino)methyl)cyclopropanecarboxamido]-adamantan-1-carboxylic acid amide;

(22) E-4-[1-((2-fluoro-N-methyl-benzenesulfonylamino) methyl)cyclopropanecarboxamido]-adamantan-1-carboxylic acid amide;
(23) E-4-[1-((4-trifluoromethoxy-benzenesulfonylamino) methyl)cyclopropanecarboxamido]-adamantan-1-carboxylic acid amide;
(24) E-4-[1-((2,3-difluoro-benzeneamino)methyl)cyclopropanecarboxamido]-adamantan-1-carboxylic acid amide;
(25) E-4-[1-((3.4-difluoro-benzeneamino)methyl)cyclopropanecarboxamido]-adamantan-1-carboxylic acid amide;
(26) E-4-[1-((1-methyl-1H-indole-5-sulfonylamino)methyl) cyclopropanecarboxamido]-adamantan-1-carboxylic acid amide;
(27) E-4-[1-((1-methyl-1H-pyrazole-5-sulfonylamino) methyl)cyclopropanecarboxamido]-adamantan-1-carboxylic acid amide;
(28) E-4-[1-((benzenesulfonylamino)methyl)cyclopropanecarboxamido]-adamantan-1-carboxylic acid amide;
(29) E-4-[1-((2-fluoro-benzenesulfonylamino)methyl)cyclopropanecarboxamido]-adamantan-1-carboxylic acid;
(30) N-(bicyclo[2.2.1]heptan-2-yl)-1-((2-fluoro-N-methyl-benzenesulfonylamino)methyl)cyclopropanecarboxamido;
(31) N-(adamantan-1-yl)-1-((2-fluoro-N-methylbenzenesulfonylamino)methyl)cyclopropanecarboxamido;
(32) E-4-[1-((N-ethyl-fluoro-benzenesulfonylamino) methyl)cyclopropanecarboxamido]-adamantan-1-carboxylic acid amide;
(33) E-3-(4-(1((2-fluoro-benzenesulfonylamino)methyl)cyclopropanecarboxamido)adamantan-1-yl)propanoic acid;
(34) E-N-(5-(3-amino-3-oxopropyl)adamantan-2-yl)-1-((2-fluoro-benzenesulfonylamino)methyl)cyclopropanecarboxamide;
(35) E-N-(5-aminoadamantan-2-yl)-1-((2-fluoro-benzenesulfonylamino)methyl)cyclopropanecarboxamidehydrochloride; and
(36) E-4-[1-((2,4,5-trifluoro-benzenesulfonylamino)methyl) cyclopropanecarboxamido]-adamantan-1-carboxylic acid amide.

Other preferable examples of the compound represented by formula 1 of the present invention are as follows:
(37) E-4-[1-((4-chloro-benzenesulfonylamino)methyl)cyclopropanecarboxamido]-adamantan-1-carboxylic acid amide;
(38) E-4-[1-(3-chloro-benzenesulfonylamino)cyclopropanecarboxamido]-adamantan-1-carboxylic acid amide;
(39) E-4-[1-(2-fluoro-benzenesulfonylamino)cyclopropanecarboxamido]-adamantan-1-carboxylic acid amide;
(40) E-4-[1-(2-fluoro-6-methyl-benzenesulfonylamino)cyclopropanecarboxamido]-adamantan-1-carboxylic acid amide;
(41) E-4-[1-(3-chloro-2-methyl-benzenesulfonylamino)cyclopropanecarboxamido]-adamantan-1-carboxylic acid amide;
(42) E-4-[1-(4-fluoro-benzenesulfonylamino)cyclopropanecarboxamido]-adamantan-1-carboxylic acid amide;
(43) E-4-[1-(2,4-dichloro-5-methyl-benzenesulfonylamino) cyclopropanecarboxamido]-adamantan-1-carboxylic acid amide;
(44) E-4-[1-(2,4-difluorochloro-benzenesulfonylamino)cyclopropanecarboxamido]-adamantan-1-carboxylic acid amide;
(45) E-4-[1-(2-fluoro-4,5-dichloro-benzenesulfonylamino) cyclopropanecarboxamido]-adamantan-1-carboxylic acid amide;
(46) E-4-[1-(2-fluoro-4-chloro-5-methyl-benzenesulfonylamino)cyclopropanecarboxamido]-adamantan-1-carboxylic acid amide;
(47) E-4-[1-(2,3,4-trifluoro-benzenesulfonylamino)cyclopropanecarboxamido]-adamantan-1-carboxylic acid amide;
(48) E-4-[1-(thiophen-2-sulfonylamino)cyclopropanecarboxamido]-adamantan-1-carboxylic acid amide;
(49) E-4-[3-(6-trifluoromethyl-pyridin-2-sulfonylamino)cyclopropanecarboxamido]-adamantan-1-carboxylic acid amide;
(50) E-4-[1-(1-methyl-1H-indole-7-sulfonylamino)cyclopropanecarboxamido]-adamantan-1-carboxylic acid amide;
(51) 1-(3-chloro-benzenesulfonylamino)-N-(4-fluoro-2-(trifluoromethyl)phenyl)cyclopropanecarboxamide;
(52) E-4-[1-(3-chloro-benzenesulfonylamino)cyclopropanecarboxamido]-N-hydroxyadamantan-1-carboxylic acid amide;
(53) 1-(3-chloro-benzenesulfonylamino)-N-[4-(1,1,1-trifluoro-2-hydroxypropan-2-yl)phenyl]cyclopropanecarboxamide;
(54) E-4-[1-(3-chloro-benzeneamino)cyclopropanecarboxamido]-adamantan-1-carboxylic acid amide;
(55) N-(bicyclo[2.2.1]heptan-2-yl)-1-(3-chloro-benzenesulfonylamino)cyclopropanecarboxamide;
(56) E-4-[1-(1,1-dioxydobenzo[d]isothiazol-2(3H)-yl)cyclopropanecarboxamido]adamantan-1-carboxylic acid amide;
(57) E-4-[1-(3, 4-difluoro-benzeneamino)cyclopropanecarboxamido]-adamantan-1-carboxylic acid amide;
(58) E-4-[1-(1-methyl-1H-pyrazole-5-sulfonylamino)cyclopropanecarboxamido]-adamantan-1-carboxylic acid amide;
(59) E-4-[1-(2,3-difluoro-benzeneamino)cyclopropanecarboxamido]-adamantan-1-carboxylic acid amide;
(60) E-4-[1-(benzenesulfonylamino)cyclopropanecarboxamido]-N-hydroxyadamantan-1-carboxylic acid amide;
(61) E-4-[1-(2-fluoro-N-methylbenzenesulfonylamino)cyclopropanecarboxamido]-adamantan-1-carboxylic acid amide;
(62) E-4-[1-(3-chloro-N-methylbenzenesulfonylamino)cyclopropanecarboxamido]-adamantan-1-carboxylic acid amide;
(63) E-4-[1-(2-fluorobenzamido)cyclopropanecarboxamido]-adamantan-1-carboxylic acid amide;
(64) E-N-[1-(5-carbamoyladamantan-2-yl)carbamoyl)cyclopropyl)-5-(trifluoromethyl)pyrrolineamide;
(65) E-4-(1-(benzo[d][1,3]dioxol-5-sulfonylamino)cyclopropanecarboxamino)adamantan-1-carboxylic acid amide; and
(66) 1-(3-chloro-benzenesulfonylamino)-N-cycloheptyl-N-propylcyclopropanecarboxamide.

Preferable examples of the compound represented by formula 1 of the present invention are as follows:
(67) E-4-(3-(3-chloro-benzenesulfonylamino)-2,2-dimethylpropanamido)adamantan-1-carboxylic acid amide;
(68) E-4-[3-(2-fluoro-benzenesulfonylamino)-2,2-dimethylpropanamido]adamantan-1-carboxylic acid amide;
(69) E-4-[3-(benzenesulfonylamino)-2,2-dimethylpropanamido]adamantan-1-carboxylic acid amide; and
(70) E-4-[3-(3-chloro-2-methyl-benzenesulfonylamino)-2,2-dimethylpropanamido]adamantan-1-carboxylic acid amide.

Preferable examples of the compound represented by formula 1 of the present invention are as follows:

(71) E-4-[2-(2-fluoro-benzenesulfonylamino)-2-methylpropanamido]-adamantan-1-carboxylic acid amide;
(72) E-4-[2-(2-fluoro-N-methyl-benzenesulfonylamino)-2-methylpropanamido]adamantan-1-carboxylic acid amide;
(73) E-4-[2-(3-chloro-benzenesulfonylamino)-2-methylpropanamido]adamantan-1-carboxylic acid amide;
(74) E-N-(5-cyanoadamantan-2-yl)-2-(2-fluoro-benzenesulfonylamino)-2-methylpropanamide;
(75) E-2-(2-fluoro-benzenesulfonylamino)-N-[5-(N'-carbamimidoyl)adamantan-2-yl]-2-methylpropanamide;
(76) E-2-(2-fluoro-benzene sulfonyl amino)-N-[5-(hydroxymethyl)adamantan-2-yl]-2-methylpropanamide;
(77) E-2-(2-fluoro-benzenesulfonylamino)-N-(5-formyladamantan-2-yl)-2-methylpropanamide;
(78) E-[4-(2-(2-fluoro-benzenesulfonylamino)-2-methylpropanamido)adamantan-1-yl]methyl-4-methylbenzenesulfonate;
(79) E-2-[4-(2-(2-fluorobenzenesulfonylamino)-2-methylpropanamido)adamantan-1-yl]acetic acid;
(80) E-N-[5-(2-amino-2-oxoethyl)adamantan-2-yl]-2-(2-fluorobenzenesulfonylamino)-2-methylpropanamide;
(81) E-4-[2-methyl-2-(benzenesulfonylamino)propanamido]adamantan-1-carboxylic acid amide;
(82) E-4-[2-(2-fluoro-3-chloro-benzenesulfonylamino)-2-methylpropanamido]adamantan-1-carboxylic acid amide;
(83) E-4-[2-(3,5-difluoro-benzenesulfonylamino)-2-methylpropanamido]adamantan-1-carboxylic acid amide;
(84) E-4-[2-(2,6-difluoro-benzenesulfonylamino)-2-methylpropanamido]adamantan-1-carboxylic acid amide;
(85) E-2-(2-fluoro-benzenesulfonylamino)-N-(5-(hydrazinecarbonyl)adamantan-2-yl)-2-methylpropanamide;
(86) E-N-(5-(3-amino-3-oxopropyl)adamantan-2-yl)-2-(2-fluoro-benzenesulfonylamino)-2-methylpropanamide;
(87) E-2-(2-fluoro-benzenesulfonylamino)-N-(5-(hydrazinecarbonyl)adamantan-2-yl)-2-methylpropanamide;
(88) E-4-[2-(4-chloro-benzenesulfonylamino)-2-methylpropanamido]adamantan-1-carboxylic acid amide;
(89) E-4-[2-(2,5-dichloro-benzenesulfonylamino)-2-methylpropanamido]adamantan-1-carboxylic acid amide; and
(90) 2-(3-chloro-benzenesulfonylamino)-N-cycloheptyl-2-methyl-N-propylpropanamide.

Preferable examples of the compound represented by formula 1 of the present invention are as follows:

(91) E-4-[3-(2-fluoro-benzenesulfonylamino)-benzamido]-adamantan-1-carboxylic acid amide;
(92) E-4-[2-(2-fluoro-benzenesulfonylamino)-benzamido]-adamantan-1-carboxylic acid amide;
(93) E-4-[4-(2-fluoro-benzenesulfonylamino)-benzamido]-adamantan-1-carboxylic acid amide;
(94) E-4-[3-(4-fluoro-benzenesulfonylamino)-benzamido]-adamantan-1-carboxylic acid amide;
(95) E-4-[3-(3-chloro-benzenesulfonylamino)-benzamido]-adamantan-1-carboxylic acid amide;
(96) E-4-[3-(3-chloro-2-methyl-benzenesulfonylamino)-benzamido]-adamantan-1-carboxylic acid amide;
(97) E-4-(3-[(3-chloro-benzenesulfonyl)-methylamino]-benzamido)-adamantan-1-carboxylic acid amide;
(98) E-4-[3-N-(2-hydroxyethyl)-2-(trifluoromethyl-benzenesulfonylamino)benzamido]-adamantan-1-carboxylic acid amide;
(99) E-4-(3-[(2-trifluoromethyl-benzenesulfonyl)-methylamino]-benzamido)-adamantan-1-carboxylic acid amide;
(100) E-sodium[3-((5-carbamoyladamantan-2-yl)carbamoyl)phenyl](2-(trifluoromethyl)benzenesulfonylamide;
(101) E-N-(5-carbamoyladamantan-2-yl)-5-[(N-methyl-2-(trifluoromethyl)benzenesulfonylamino]nicotinamide;
(102) E-4-[3-(thiophen-2-sulfonylamino)-benzamido]-adamantan-1-carboxylic acid amide;
(103) E-4-[3-(furan-2-sulfonylamino)-benzamido]-adamantan-1-carboxylic acid amide;
(104) E-4-[3-(pyridin-3-sulfonylamino)-benzamido]-adamantan-1-carboxylic acid amide;
(105) E-4-(3-(benzenesulfonylamino-benzamido)-adamantan-1-carboxylic acid amide;
(106) E-4-[3-[(2-chloro-benzenesulfonylamino]benzamido]-adamantan-1-carboxylic acid amide;
(107) E-4-[3-[(2,4-dimethyl-thiazol-5-sulfonylamino)-benzamido]-adamantan-1-carboxylic acid amide;
(108) E-4-[3-(3,5-dimethyl-1H-pyrazole-4-sulfonylamino)-benzamido]-adamantan-1-carboxylic acid amide;
(109) E-N-(5-hydroxy-adamantan-2-yl)-3-benzenesulfonylamino-benzamide;
(110) E-N-cycloheptyl-3-phenylsulfamoyl-benzamide;
(111) E-N-(5-hydroxyadamantan-2-yl)-3-(2-(trifluoromethyl)benzenesulfonylamino)benzamide;
(112) E-4-(3-(N-phenylsulfamoylbenzamino)-adamantan-1-carboxylic acid amide;
(113) E-sodium[3-((5-carbamoyladamantan-2-yl)carbamoyl)phenyl]-2-fluoro-3-chloro-benzenesulfonylamide;
(114) E-4-[3-(3-chloro-4-(trifluoromethyl)benzenesulfonylamino)benzamido]adamantan-1-carboxylic acid amide;
(115) E-4-[3-[(2-(trifluoromethyl)benzenesulfonylamino]-benzamido]-adamantan-1-carboxylic acid amide;
(116) E-4-[3-(2-chloro-4-bromo-benzenesulfonylamino)-benzamido]-adamantan-1-carboxylic acid amide;
(117) E-4-[3-(2,4,6-trichloro-benzenesulfonylamino)-benzamido]-adamantan-1-carboxylic acid amide;
(118) E-4-[3-(3-chloro-5-fluoro-benzenesulfonylamino)benzamido]-adamantan-1-carboxylic acid amide;
(119) E-4-[3-(3,5-dichloro-benzenesulfonylamino)benzamido]-adamantan-1-carboxylic acid amide;
(120) E-4-[3-(3-fluoro-benzene sulfonyl amino)benzamido]-adamantan-1-carboxylic acid amide;
(121) E-4-[3-(2,4-difluoro-benzenesulfonylamino)-benzamido]-adamantan-1-carboxylic acid amide;
(122) E-4-[3-(2,5-difluoro-benzenesulfonylamino)-benzamido]-adamantan-1-carboxylic acid amide;
(123) E-4-[3-(2,6-difluoro-benzenesulfonylamino)-benzamido]-adamantan-1-carboxylic acid amide;
(124) E-N-cycloheptyl-N-propyl-3-(2-(trifluoromethyl)benzenesulfonylamino)benzamide;
(125) E-4-[2-fluoro-3-(2-(trifluoromethyl)benzenesulfonylamino)benzamido]adamantan-1-carboxylic acid amide;
(126) E-4-[2-chloro-5-(3-chloro-benzenesulfonylamino)benzamido]adamantan-1-carboxylic acid amide;
(127) E-4-[3-(3-chlorobenzenesulfonylamino)-4-fluorobenzamido]adamantan-1-carboxylic acid amide;
(128) E-4-[4-chloro-3-(3,5-dichlorobenzenesulfonylamino)benzamido]adamantan-1-carboxylic acid amide;
(129) E-4-[2-chloro-5-(3,5-dichlorobenzenesulfonylamino)benzamido]adamantan-1-carboxylic acid amide;
(130) E-4-[3-(3,5-dichlorobenzenesulfonylamino)-4-fluorobenzamido]adamantan-1-carboxylic acid amide;
(131) E-4-[5-(3,5-dichlorobenzenesulfonylamino)-2-fluorobenzamido]adamantan-1-carboxylic acid amide;
(132) E-4-[2-fluoro-3-(3-chloro-benzenesulfonylamino)benzamido]adamantan-1-carboxylic acid amide;
(133) E-4-[2-chloro-5-(3-chloro-4-methoxybenzenesulfonylamino)benzamido]adamantan-1-carboxylic acid amide;

(134) E-4-[4-chloro-3-(3-chloro-4-methoxybenzenesulfonylamino)benzamido]adamantan-1-carboxylic acid amide;
(135) E-4-[5-(3-chloro-4-methoxybenzenesulfonylamino)-2-fluorobenzamido]adamantan-1-carboxylic acid amide;
(136) E-4-(3-(4-chloro-benzenesulfonylamino-benzamido)-adamantan-1-carboxylic acid amide;
(137) E-4-(3-(4-chloro-benzenesulfonylamino-benzamido)-adamantan-1-carboxylic acid amide;
(138) E-4-(3-(cyclopropanesulfonamido)benzamido)adamantan-1-carboxylic acid amide; and
(139) E-4-(3-(1-methylethylsulfonamido)benzamido)adamantan-1-carboxylic acid amide.

Preferable examples of the compound represented by formula 1 of the present invention are as follows:
(140) E-[3,4-dihydro-1H-isoquinolin-2-carboxylic acid-1-[(5-carbamoyl-adamantan-2-ylcarbamoyl)cyclopropylmethyl]-amide;
(141) E-3,4-dihydro-2H-quinolin-1-carboxylic acid[1-(5-carbamoyl-adamantan-2-yl carbamoyl)-cyclopropylmethyl]-amide;
(142) E-piperidin-1-carboxylic acid[1-(5-carbamoyl-adamantan-2-ylcarbamoyl)-cyclopropylmethyl]-amide;
(143) E-4-([1-5-carbamoyl-adamantan-2-yl carbamoyl)-cyclopropylmethyl]-carbamoyl)-3,4-dihydro-2H-quinolin-1carboxylic acid-butylester;
(144) E-4-pyrimidin-2-yl-piperazin-1-carboxylic acid[1-(5-carbamoyl-adamantan-2-ylcarbamoyl)-cyclopropylmethyl]-amide;
(145) E-4-((1[(3-phenyl-ureido)methyl]-cyclopropanecarbonyl)amino)-adamantan-1carboxylic acid amide;
(146) E-3,4-dihydro-2H-quinoxalin-1-carboxylic acid[1-(5-carbamoyl-adamantan-2-ylcarbamoyl)-cyclopropylmethyl]-amide;
(147) E-3,4-dihydro-1H-isoquinolin-2-carboxylic acid[4-(5-carbamoyl-adamantan-2-ylcarbamoyl)-thiazol-2-yl]-amide;
(148) E-3,4-dihydro-2H-quinolin-1-carboxylic acid [4-(5-carbamoyl-adamantan-2-ylcarbamoyl)-thiazol-2-yl]-amide; and
(149) E-2-(2-fluoro-benzamido)-thiazol-4-carboxylic acid (5-carbamoyl-adamantan-2-yl)amide.

The compound represented by formula 1 of the present invention can be used as a form of a pharmaceutically acceptable salt, in which the salt is preferably acid addition salt formed by pharmaceutically acceptable free acids. Herein, the pharmaceutically acceptable salt indicates any organic or inorganic addition salt of the base compound represented by formula 1 that is relatively nontoxic to a patient and has non-harmful activity whose side effect cannot reduce any positive effect of the said base compound represented by formula 1. The acid addition salt herein can be obtained from inorganic acids such as hydrochloric acid, bromic acid, nitric acid, sulfuric acid, perchloric acid, and phosphoric acid; or organic acids such as citric acid, acetic acid, lactic acid, maleic acid, fumaric acid, gluconic acid, methane sulfonic acid, glyconic acid, succinic acid, tartaric acid, galacturonic acid, embonic acid, glutamic acid, aspartic acid, oxalic acid, (D) or (L) malic acid, methane sulfonic acid, ethanesulfonic acid, 4-toluenesulfonic acid, salicilic acid, citric acid, benzoic acid, and malonic acid. The salt herein includes alkali metal salt (sodium salt, potassium salt, etc) and alkali earth metal salt (calcium salt, magnesium salt, etc). For example, the acid addition salt is exemplified by acetate, aspartate, benzoate, besylate, bicarbonate/carbonate, bisulfate/sulfate, borate, camcilate, citrate, edisylate, ethylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, methylate, methylsulfate, naphthalate, 2-naphthylate, nicotinate, nitrate, orotate, oxalate, palmitate, pamoate, phosphate/hydrogen phosphate/dihydrogen phosphate, saccharate, stearate, succinate, tartrate, tosylate, trifluoroacetate, aluminum, arginine, benzathine, calcium, choline, diethylamine, diolamine, glycine, lysine, magnesium, meglumine, olamine, potassium, sodium, tromethamine, and zinc salt. Among them, hydrochloride or trifluoroacetate is preferred.

The compound represented by formula 1 of the present invention not only includes the pharmaceutically acceptable salts but also includes every possible salts, isomers, hydrates, and solvates constructed from the same by the conventional method.

The acid addition salt in this invention can be prepared by the conventional method known to those in the art. For example, the compound of formula 1 of the present invention is dissolved in a water-miscible organic solvent such as acetone, methanol, ethanol, or acetonitrile, to which excessive organic acid or acid aqueous solution of inorganic acid is added to induce precipitation or crystallization. Then, the solvent or the excessive acid is evaporated from the mixture, followed by drying the mixture to give addition salt or suction-filtering the precipitated salt to give the same.

Some compounds among those represented by formula 1 contain chiral center or geometrical isomer center (E and Z isomers). It is understood that the present invention includes all the optical isomers, diastereomers, and geometrical isomers having the activity of inhibiting 11β-HSD1.

The present invention also relates to every random/possible favorable or non-favorable changes of the compound of formula 1 having the activity of inhibiting 11β-HSD1. Particularly, it can be understood that the compound of formula 1 can be in the form of solvate or nonsolvate, for example in the form of hydrate. Thus, the present invention includes all those compounds in every kinds of solvates as long as they display 11β-HSD1 inhibiting activity.

The present invention also provides a preparation method of the compound represented by formula 1 containing the step of reacting the compound represented by formula 2 with the compound represented by formula 3 to prepare the compound of formula 1, as represented in the following reaction formula 1.

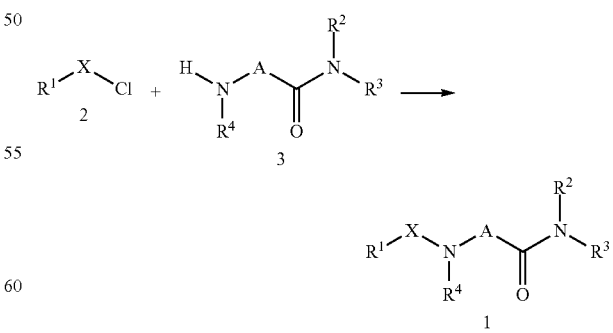

[Reaction Formula 1]

In reaction formula 1,
$R^1$-$R^4$, X and A are as defined in formula 1.
In the preparation method of the present invention, the compound represented by formula 2 can be a sulfonylhalide derivative or an acetylhalide derivative. The compounds of formula 2 and formula 3 can be the commercial compounds on the market or can be synthesized by those of knowledge in the art, considering the substituents therein.

Particularly, the compound of formula 1 of the present invention can be easily prepared by reacting the amine derivative compound represented by formula 3 with the sulfonylhalide derivative or the acetylhalide derivative represented by formula 2 in the presence of a general organic solvent like dichloromethane with the addition of a proper amount of diisopropylethylamine. At this time, the reaction temperature and the reaction time can vary with the chemical reactivity of the sulfonylhalide derivative or the acetylhalide derivative represented by formula 2, but the reaction for 1-24 hours at room temperature is preferred, but not always limited thereto.

After the compound of formula 1 was prepared by the method described above, the molecular structure of the compound was confirmed by infrared spectroscopy (IR), nuclear magnetic resonance spectrum (NMR), mass spectrometry (Mass), liquid chromatography, X-ray crystallography, polarimetry, and the comparison of the estimated data and the analyzed data of the representative compound.

In addition, the present invention provides a pharmaceutical composition for the prevention or treatment of diseases caused by the over-activation of 11β-HSD1 enzyme which comprises the compound represented by formula 1 or the pharmaceutically acceptable salt thereof as an active ingredient.

The compound represented by formula 1 was confirmed to have excellent 11β-HSD1 inhibiting activity. Precisely, $IC_{50}$ of the compound, which was the concentration of the compound to inhibit the 11β-HSD1 activity 50%, was 0.02-672 nM.

Therefore, since the compound of formula 1 of the present invention has excellent 11β-HSD1 inhibiting activity, it can be effectively used for the prevention or treatment of diseases mediated by abnormally activated 11β-HSD1, such as non-insulin dependent type II diabetes, insulin resistance, obesity, lipid disorder, metabolic syndrome, and other diseases mediated by the excessive activity of glucocorticoid.

The pharmaceutical composition of the present invention comprising the compound represented by formula 1 or the pharmaceutically acceptable salt thereof as an active ingredient can be administered orally or parenterally and be used in general forms of pharmaceutical formulation, but not always limited thereto The formulations for oral administration are exemplified by tablets, pills, hard/soft capsules, solutions, suspensions, emulsions, syrups, granules, and elixirs, etc. These formulations can include diluents (for example, lactose, dextrose, sucrose, mannitol, sorbitol, cellulose, and/or glycine) and lubricants (for example, silica, talc, stearate and its magnesium or calcium salt, and/or polyethylene glycol) in addition to the active ingredient. Tablets can include binding agents such as magnesium aluminum silicate, starch paste, gelatin, methylcellulose, sodium carboxymethylcellulose and/or polyvinylpyrolidone, and if necessary disintegrating agents such as starch, agarose, alginic acid or its sodium salt or azeotropic mixtures and/or absorbents, coloring agents, flavors, and sweeteners can be additionally included thereto.

The effective dosage of the compound of the present invention can be determined according to age, weight, gender, administration method, health condition, and severity of disease. For example, the dose for an adult in 70 kg of body weight is 0.1-1,000 mg/day and preferably 1-500 mg/day. This administration can be performed once a day—several times a day according to the decision of a doctor or a pharmacist.

Practical and presently preferred embodiments of the present invention are illustrative as shown in the following Examples.

However, it will be appreciated that those skilled in the art, on consideration of this disclosure, may make modifications and improvements within the spirit and scope of the present invention.

Preparational Example 1

Preparation of 1-(aminomethyl)-cyclopropylacetic acid hydrochloride

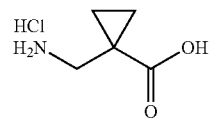

200 mg (1.75 mmol) of 1-cyano-1-cyclopropylacetic acid was dissolved in 10 ml of methanol, to which 40 mg (20 wt %) of platinum oxide was added. 0.3 ml of concentrated hydrochloric acid solution was loaded thereto, and the mixture was stirred at room temperature for 4 hours in hydrogen stream. Upon completion of the reaction, the mixture was filtered to eliminate platinum oxide. The solvent was evaporated under reduced pressure to give 256 mg of 1-(aminomethyl)-cyclopropylacetic acid hydrochloride (yield: 97%).

$^1$H NMR (400 MHz, MeOD) δ 3.13 (s, 2H), 1.36-1.38 (m, 2H), 1.16-1.18 (m, 2H)

Preparational Example 2

Preparation of 1-(aminomethyl)-cyclopropylcarboxylic acid methylester hydrochloride

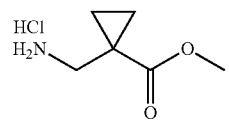

273 mg (1.8 mmol) of the 1-(aminomethyl)-cyclopropylacetic acid hydrochloride prepared in Preparational Example 1 was dissolved in 6 ml of methanol, to which 0.26 ml (3.6 mmol) of thionyl chloride was added, followed by stirring at room temperature for 3 hours. Upon completion of the reaction, the solvent was evaporated under reduced pressure to give 291 mg of 1-(aminomethyl)-cyclopropylcarboxylic acid methylester hydrochloride (yield: 98%).

$^1$H NMR (400 MHz, D$_2$O) δ 3.60 (s, 3H), 3.06 (s, 2H), 1.28-1.31 (m, 2H), 0.97-0.99 (m, 2H)

Preparational Example 3

Preparation of 1-[(2-fluoro-benzenesulfonylamino)methyl]-1-cyclopropylcarboxylic acid methyl ester

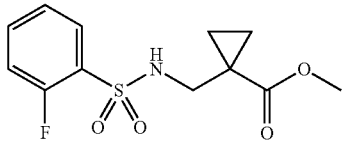 [SMILES: COC(=O)C1(CNS(=O)(=O)c2ccccc2F)CC1]

150 (0.91 mmol) mg of the 1-(aminomethyl)-cyclopropylcarboxylic acid methylester hydrochloride prepared in Preparational Example 2 was dissolved in 3 ml of methylene chloride, to which 0.25 ml of TEA was added, followed by stirring at room temperature for 5 minutes. 194 mg (1.0 mmol) of 2-fluorosulfonylchloride was added to the reactant, followed by stirring at room temperature for 3 hours, followed by evaporation under reduced pressure to eliminate the reaction solvent. The residue was dissolved in 5 ml of water, followed by extraction with 310 ml of ethyl acetate. The extract was dried over anhydrous magnesium sulfate, and evaporated under reduced pressure, followed by column chromatography to give 215 mg of 1-[(2-fluoro-benzenesulfonylamino)methyl]-cyclopropylcarboxylic acid methyl ester (yield: 83%).

$^1$H NMR (400 MHz, CDCl$_3$) δ 7.86-7.92 (m, 1H), 7.56-7.60 (m, 1H), 7.20-7.32 (m, 2H), 5.67 (d, J=5.2 Hz, 1H), 3.64-3.72 (m, 3H), 3.14-3.21 (m, 2H), 1.17-1.21 (m, 2H), 0.84-0.91 (m, 2H)

Preparational Example 4

Preparation of 1-[(2-fluoro-benzenesulfonylamino)methyl]-cyclopropylcarboxylic acid

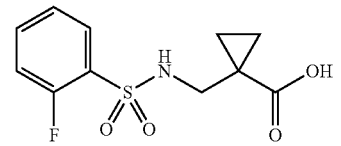 [SMILES: O=C(O)C1(CNS(=O)(=O)c2ccccc2F)CC1]

215 mg (0.75 mmol) of the 1-[(2-fluoro-benzenesulfonylamino)methyl]-cyclopropylcarboxylic acid methyl ester prepared in Preparational Example 3 was dissolved in 7.5 ml of the mixed solvent of distilled water and THF (1:2), to which 94 mg (2.25 mmol) of lithium hydroxide monohydrate was added, followed by stirring at room temperature for 16 hours. Upon completion of the reaction, the reaction solvent was eliminated by evaporation under reduced pressure and the residue was acidized with 1 N HCl to be pH 3, followed by extraction with 320 ml of ethyl acetate. The extract was dried over anhydrous magnesium sulfate, followed by evaporation under reduced pressure to give 200 mg of 1-[(2-fluoro-benzenesulfonylamino)methyl]-cyclopropylcarboxylic acid (yield: 98%).

$^1$H NMR (400 MHz, CDCl$_3$) δ 7.85-7.90 (m, 1H), 7.56-7.61 (m, 1H), 6.98-7.31 (m, 2H), 5.90 (t, J=6.2 Hz, 1H), 3.15-3.17 (m, 2H), 1.29-1.32 (m, 2H), 0.93-0.97 (m, 2H)

Preparational Example 5

Preparation of 1-[(t-butoxycarbonylamino)methyl]cyclopropyl acetic acid

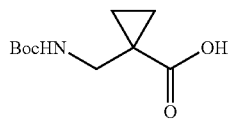

256 mg (1.69 mmol) of the 1-(aminomethyl)-cyclopropylacetic acid hydrochloride prepared in Preparational Example 1 was dissolved in 3 ml of methylene chloride, to which 0.26 ml (1.86 mmol) of TEA was added, followed by stirring for 10 minutes. Methylene chloride was eliminated by evaporation under reduced pressure. The reactant was dissolved in 2 ml of 1.0 N NaOH and 6 ml of 1,4-dioxane, and then 443 mg (2.0 mmol) of Boc$_2$O was added thereto. After stirring the reaction mixture at room temperature for 16 hours, 1,4-dioxane was eliminated by evaporation under reduced pressure. The residue was acidized with 1 N HCl to be pH 3, followed by extraction with 320 ml of ethyl acetate. The extract was dried over anhydrous magnesium sulfate, followed by evaporation under reduced pressure to give 345 mg of 1-[(t-butoxycarbonylamino)methyl]cyclopropylacetic acid (yield: 95%).

$^1$H NMR (400 MHz, MeOD) δ 1.51 (s, 2H), 1.43 (s, 9H), 1.13-1.16 (m, 2H), 0.89-0.91 (m, 2H)

Preparational Example 6

Preparation of 4-oxo-adamantan-1-carboxylic acid methyl ester

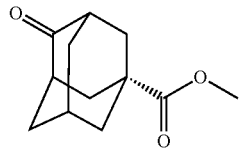

30% fuming sulfuric acid solution was heated at 60° C., to which 1 g (6.02 mmol) of 5-hydroxy-2-adamantanone dissolved in 6 ml of 99% formic acid was slowly added over 1 hour. After adding 6 ml of 99% formic acid slowly for 1 hour, the mixture was stirred at 60° C. for 1 hour. The reaction solution was slowly added to 50 ml of methanol cooled down to 0° C., followed by stirring at room temperature for 2 hours. Then, the reaction solution was evaporated under reduced pressure. 15 g of ice and 50 ml of methylene chloride were added thereto, followed by extraction with methylene chloride twice. After washing with brine, the extract was dried over anhydrous magnesium sulfate, followed by evaporation under reduced pressure to give 1.09 g of 4-oxo-adamantan-1-carboxylic acid methyl ester (yield: 87%).

$^1$H NMR (400 MHz, CDCl$_3$) δ 3.69 (s, 3H), 2.19 (m, 2H), 1.98-2.24 (m, 11H)

Preparational Example 7

Preparation of 4-amino-adamantan-1-carboxylic acid methyl ester

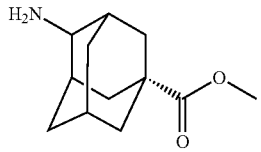

1.09 g (5.234 mmol) of the 4-oxo-adamantan-1-carboxylic acid methyl ester prepared in Preparational Example 6 and 0.5 g of 4 Å molecular sieves were dissolved in 9.3 ml of methanolic ammonia (7N). The mixture was stirred at room temperature overnight, followed by cooling down to 0° C. NaBH$_4$ was slowly added thereto, followed by stirring at room temperature for 2 hours. The floating materials generated therein were eliminated by filtering. The solvent was eliminated by evaporation under reduced pressure. The residue was dissolved in 100 ml of methylene chloride, followed by acidization with 10% citric acid. Then, the reactant was neutralized with NaHCO$_3$ solution, followed by washing with brine. The reactant was extracted twice with methylene chloride. The extract was dried over anhydrous magnesium sulfate, followed by evaporation under reduced pressure to give 800 mg of 4-amino-adamantan-1-carboxylic acid methyl ester (yield: 73%).

$^1$H NMR (400 MHz, CDCl$_3$) δ 3.67 (s, 3H), 3.03 (m, 1H), 1.48-2.02 (m, 13H)

Preparational Example 8

Preparation of t-butyl[(1-(adamantan-2-ylcarbamoyl)cyclopropyl)methyl]carbamate

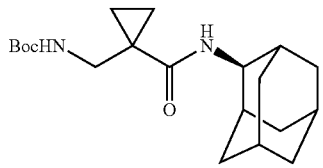

33 mg (0.15 mmol) of the 1-[(t-butoxycarbonylamino)methyl]cyclopropyl acetic acid prepared in Preparational Example 5 and 32 mg (0.17 mmol) of 2-admantaneamine hydrochloride were dissolved in 1.5 ml of methylene chloride, to which 44 mg (0.17 mmol) of BOP—Cl was added. 0.04 ml (0.31 mmol) of TEA was also added thereto. The reaction mixture was stirred at room temperature for 16 hours, followed by evaporation under reduced pressure to eliminate methylene chloride. The residue was dissolved in 5 ml of water, followed by extraction with 310 ml of methylene chloride. The extract was dried over anhydrous magnesium sulfate, and evaporated under reduced pressure, followed by column chromatography to give 34 mg of t-butyl[(1-(adamantan-2-ylcarbamoyl)cyclopropyl)methyl]carbamate (yield: 64%).

$^1$H NMR (400 MHz, CDCl$_3$) δ 7.02 (brs, 1H), 4.89 (s, 1H), 4.03 (d, J=7.2 Hz, 1H), 3.37 (d, J=6.8 Hz, 2H), 1.49-2.05 (m, 14H), 1.44 (s, 9H), 1.23-1.26 (m, 2H). 0.60-0.66 (m, 2H)

Preparational Example 9

Preparation of 4-[1-(t-butoxycarbonylamino)methyl-cyclopropanecarboxamido]-adamantan-1-carboxylic acid methyl ester

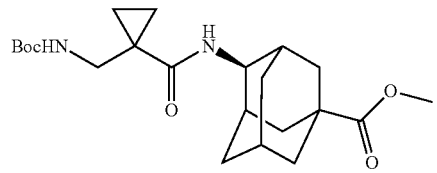

391 mg (1.82 mmol) of the 1-[(t-butoxycarbonylamino)methyl]cyclopropyl acetic acid prepared in Preparational Example 5 and 492 mg (2.00 mmol) of the 4-amino-adamantan-1-carboxylic acid methyl ester prepared in Preparational Example 7 were dissolved in 6.0 ml of methylene chloride, to which 525 mg (2.00 mmol) of BOP—Cl was added. 0.5 ml (3.64 mmol) of TEA was also added thereto. The reaction mixture was stirred at room temperature for 16 hours, followed by evaporation under reduced pressure to eliminate methylene chloride. The residue was dissolved in 10 ml of water, followed by extraction with 320 ml of ethyl acetate. The extract was dried over anhydrous magnesium sulfate, and evaporated under reduced pressure, followed by column chromatography to give 400 mg of 4-[1-(t-butoxycarbonylamino)methyl-cyclopropanecarboxamido]-adamantan-1-carboxylic acid methyl ester (yield: 54%).

$^1$H NMR (400 MHz, CDCl$_3$) δ 7.16 (brs, 1H), 4.87 (t, J=5.8 Hz, 1H), 4.01 (d, J=6.8 Hz, 1H), 3.65 (s, 3H), 3.37 (d, J=6.4 Hz, 2H), 1.94-2.05 (m, 9H), 1.89 (s, (m, 2H), 1.54 (s, J=12.4 Hz, 2H), 1.42 (s, 9H), 1.25-1.28 (m, 2H). 0.63-0.65 (m, 2H)

Preparational Example 10

Preparation of 4-[1-(aminomethyl)cyclopropanylcarboxamido]-adamantan-1-carboxylic acid methyl ester hydrochloride

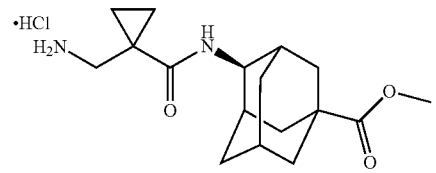

4.0 g (9.8 mmol) of the 4-[1-(t-butoxycarbonylamino)methyl-cyclopropanecarboxamido]-adamantan-1-carboxylic acid methyl ester prepared in Preparational Example 9 was dissolved in 33 ml of ethyl acetate, to which 25 ml of 4 M HCl 1,4-dioxane solution was added. The reaction mixture was stirred at room temperature for 6 hours. Upon completion of the reaction, the reaction solvent was eliminated by evaporation under reduced pressure. The residue was dissolved in 50 ml of ethylene acetate and the precipitated solid compound was filtered. As a result, 3.2 g of 4-[1-(aminomethyl)cyclopropanylcarboxamido]-adamantan-1-carboxylic acid methyl ester hydrochloride was obtained (yield: 92%).

$^1$H NMR (400 MHz, MeOD) δ 3.90 (s, 1H), 3.64 (s, 3H), 3.08 (s, 2H), 1.90-2.05 (m, 11H), 1.55 (s, J=12.4 Hz, 2H), 1.35-1.38 (s, 2H), 1.05-1.11 (m, 2H)

Preparational Example 11

Preparation of 4-[1-((2-fluoro-benzenesulfonylamino)methyl)cyclopropanecarboxamido]-adamantan-1-carboxylic acid methyl ester

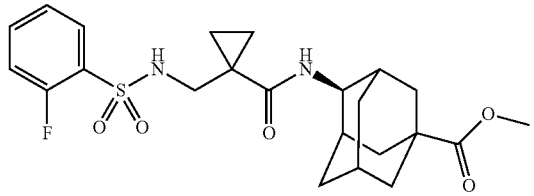

1.0 g (3.2 mmol) of the 4-[1-(aminomethyl)cyclopropanylcarboxamido]-adamantan-1-carboxylic acid methyl ester hydrochloride prepared in Preparational Example 10 was dissolved in 10 ml of methylene chloride, to which 0.8 ml of TEA was added, followed by stirring at room temperature for 5 minutes. 624 mg (3.2 mmol) of 2-fluorosulfonylchloride was added to the reaction mixture, followed by stirring at room temperature for 6 hours. The reaction solvent was eliminated by evaporation under reduced pressure. The residue was dissolved in 20 ml of water, followed by extraction with 350 ml of ethyl acetate. The extract was dried over anhydrous magnesium sulfate, and evaporated under reduced pressure, followed by column chromatography to give 1.5 g of 4-[1-((2-fluoro-benzenesulfonylamino)methyl)cyclopropanecarboxamido]-adamantan-1-carboxylic acid methyl ester (yield: 99%).

$^1$H NMR (400 MHz, CDCl$_3$) δ 7.90 (dt, J=7.6, 1.7 Hz, 1H), 7.59-7.64 (m, 1H), 7.32 (dt, J=7.6, 1.0 Hz, 1H), 7.21-7.24 (m, 1H), 6.53 (d, J=7.6 Hz, 1H), 5.28 (t, J=6.6 Hz, 1H), 4.05 (d, J=7.2 Hz, 1H), 3.66 (s, 3H), 3.12 (d, J=6.4 Hz, 2H), 1.91-2.05 (m, 11H), 1.47 (d, J=12.0 Hz, 2H), 1.21-1.23 (m, 2H), 0.67-0.70 (m, 2H)

Preparational Example 12

Preparation of 4-[1-((2-fluoro-benzenesulfonylamino)methyl)cyclopropanecarboxamido]-adamantan-1-carboxylic acid

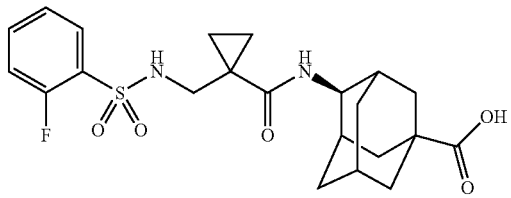

1.5 g (3.23 mmol) of the 4-[1-((2-fluoro-benzenesulfonylamino)methyl)cyclopropanecarboxamido]-adamantan-1-carboxylic acid methyl ester prepared in Preparational Example 11 was dissolved in 20 ml of THF/ethanol mixed solution (1:1), to which 8.0 ml of 2N NaOH solution was added, followed by stirring at room temperature overnight. The residue was acidized with 1 N HCl, followed by extraction with ethyl acetate. The extract was dried over anhydrous magnesium sulfate, followed by evaporation under reduced pressure to give 1.44 g of 4-[1-((2-fluoro-benzenesulfonylamino)methyl)cyclopropanecarboxamido]-adamantan-1-carboxylic acid (yield: 99%).

$^1$H NMR (400 MHz, MeOD) δ 7.89 (dt, J=7.4, 1.6 Hz, 1H), 7.65-7.70 (m, 1H), 7.46 (d, J=7.2 Hz, 1H), 7.31-7.39 (m, 2H), 4.00 (d, J=7.6 Hz, 1H), 3.15 (s, 2H), 2.16 (d, J=13.2 Hz, 2H), 1.98-2.03 (m, 7H), 1.94 (s, 2H), 1.60 (d, J=13.2 Hz, 2H), 1.13-1.16 (m, 2H), 0.69-0.72 (m, 2H)

Example 1

Preparation of N-(adamantan-2-yl)-1-[(3-chloro-2-methylbenzenesulfonylamino)methyl]cyclopropanecarboxamide

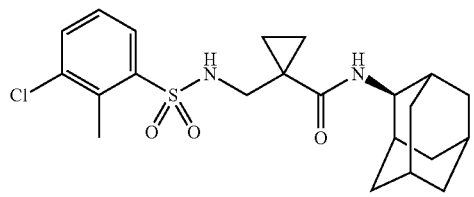

34 mg (0.09 mmol) of the t-butyl[(1-(adamantan-2-ylcarbamoyl)cyclopropyl)methyl]carbamate prepared in Preparational Example 8 was dissolved in 1.0 ml of ethyl acetate, to which 0.12 ml of 4 M HCl 1,4-dioxane solution was added, followed by stirring at room temperature for 3 hours. Upon completion of the reaction, the reaction solvent was eliminated by evaporation under reduced pressure. The residue was dissolved in 10 ml of ethylene acetate and the precipitated solid compound was filtered and dried. This solid compound was dissolved in 2 ml of methylene chloride, to which 0.03 ml of TEA was added, followed by stirring at room temperature for 5 minutes. 24 mg (0.10 mmol) of 3-chloro-2-methylbenzenesulfonylchloride was added to the reactant, which was then stirred at room temperature for 4 hours. The reaction solvent was eliminated by evaporation under reduced pressure. The residue was dissolved in 10 ml of water, followed by extraction with 320 ml of ethyl acetate. The extract was dried over anhydrous magnesium sulfate, and evaporated under reduced pressure, followed by column chromatography to give 16 mg of N-(adamantan-2-yl)-1-[(3-chloro-2-methylbenzenesulfonylamino)methyl]cyclopropanecarboxamide (yield: 39%).

$^1$H NMR (400 MHz, CDCl$_3$) δ 7.90 (dd, J=8.0, 1.2 Hz, 1H), 7.58 (dd, J=8.0, 0.8 Hz, 1H), 7.26 (t, J=8.0 Hz, 1H), 5.96 (d, J=7.6 Hz, 1H), 5.62 (t, J=6.2 Hz, 1H), 4.01 (d, J=7.6 Hz, 1H), 3.04 (d, J=6.0 Hz, 2H), 2.72 (s, 3H), 1.66-1.89 (m, 14H), 1.07-1.09 (m, 2H), 0.86-0.88 (m, 2H)

Example 2

Preparation of 1-[(2-fluoro-benzenesulfonylamino)methyl]-N-(5-hydroxyadamantan-2-yl)cyclopropanecarboxamide

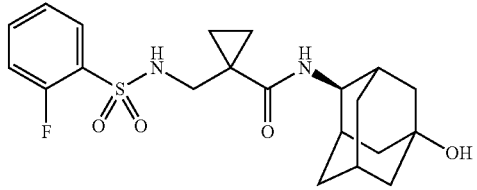

43 mg (0.16 mmol) of the 1-[(2-fluoro-benzenesulfonylamino)methyl]-cyclopropylcarboxylic acid prepared in Preparational Example 4 was dissolved in 1.6 ml of methylene chloride, to which 44 mg (0.32 mmol) of BOP—Cl, 29 mg (0.17 mmol) of 4-amino-adamantane-1-ol and 0.04 ml (0.32 mmol) of TEA were added. The reaction mixture was stirred at room temperature for 4 hours, followed by evaporation under reduced pressure to eliminate methylene chloride. The residue was dissolved in 5 ml of water, followed by extraction with 310 ml of ethyl acetate. The extract was dried over anhydrous magnesium sulfate, and evaporated under reduced pressure, followed by column chromatography to give 9 mg of 1-[(2-fluoro-benzenesulfonylamino)methyl]-N-(5-hydroxyadamantan-2-yl)cyclopropanecarboxamide (yield: 14%).

$^1$H NMR (400 MHz, CDCl$_3$) δ 7.88-7.92 (m, 1H), 7.59-7.64 (m, 1H), 7.21-7.33 (m, 2H), 6.48 (d, J=6.8 Hz, 1H), 5.29 (t, J=6.4 Hz, 1H), 4.04 (t, J=4.0 Hz, 1H), 3.12 (s, J=6.4 Hz, 2H), 2.12-2.19 (m, 3H), 1.71-1.89 (m, 9H), 1.53 (d, J=12.8 Hz, 2H), 1.21-1.23 (m, 2H), 0.67-0.69 (m, 2H)

Example 3

Preparation of E-4-[1-((2-fluoro-benzenesulfonylamino)methyl)cyclopropanecarboxamido]-adamantan-1-carboxylic acid amide

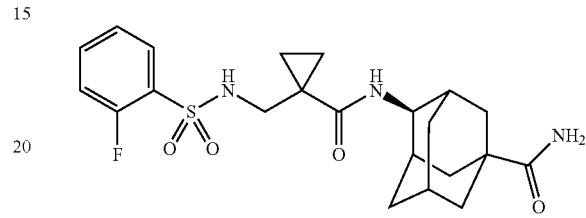

1.44 g (3.20 mmol) of the 4-[1-((2-fluoro-benzenesulfonylamino)methyl)cyclopropanecarboxamido]-adamantan-1-carboxylic acid prepared in Preparational Example 12 was dissolved in 107 ml of methylene chloride, to which 533 mg (3.84 mmol) of HOBt and 736 mg (3.84 mmol) of EDCI were added. The mixture was stirred at room temperature for 10 minutes and then 107 ml of 35% ammonia water was added thereto. The mixture was stirred at room temperature for 20 hours. Upon completion of the reaction, extraction was performed with methylene chloride. After washing with brine, the extract was dried over anhydrous magnesium sulfate, followed by column chromatography to give 1.09 g of E-4-[1-((2-fluoro-benzenesulfonylamino)methyl)cyclopropanecarboxamido]-adamantan-1-carboxylic acid amide (yield: 76%).

$^1$H NMR (400 MHz, CDCl$_3$) δ 7.88-7.92 (m, 1H), 7.59-7.64 (m, 1H), 7.31-7.33 (m, 1H), 7.24 (t, J=8.8 Hz, 1H), 6.61 (d, J=7.2 Hz, 1H), 5.61 (brs, 1H), 5.45 (t, J=6.6 Hz, 1H), 5.33 (brs, 1H), 4.06 (t, J=3.8 Hz, 1H), 3.13 (d, J=6.4 Hz, 2H), 1.91-2.09 (m, 11H), 1.63 (d, J=12.0 Hz, 2H), 1.22-1.24 (m, 2H), 0.67-0.69 (m, 2H)

The compounds of Example 4-Example 37 were prepared by the preparation method described in Example 3.

TABLE 1

| Example | Compound Name | Structure | NMR data |
|---|---|---|---|
| 4 | Z-4-[1-((2-fluoro-benzenesulfonylamino)methyl)cyclopropane carboxamido]-adamantan-1-carboxylic acid amide | 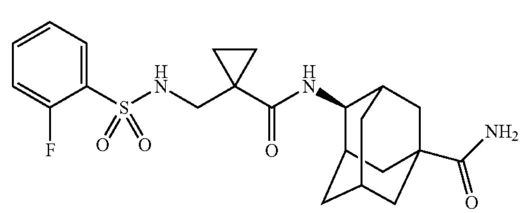 | $^1$H NMR (400 MHz, CDCl$_3$) d 7.87-7.89 (m, 1H), 7.60-7.66 (m, 1H), 7.31-7.35 (m, 1H), 7.22-7.25 (m, 2H), 7.01 (d, J = 7.6 Hz, 1H), 6.57 (t, J = 6.2 Hz, 1H), 6.28 (brs, 1H), 5.56 (brs, 1H), 4.08 (d, J = 7.6 Hz, 1H), 3.17 (d, J = 6.4 Hz, 2H), 2.04-2.12 (m, 4H), 1.92 (s, 2H), 1.74-7.84 (m, 7H), 1.27-1.30 (m, 2H), 0.65-0.67 (m, 2H) |

TABLE 1-continued

| Example | Compound Name | Structure | NMR data |
|---|---|---|---|
| 5 | E-4-[1-((3-chloro-2-methyl-benzenesulfonylamino)methyl)cyclopropane carboxamido]-adamantan-1-carboxylic acid amide | 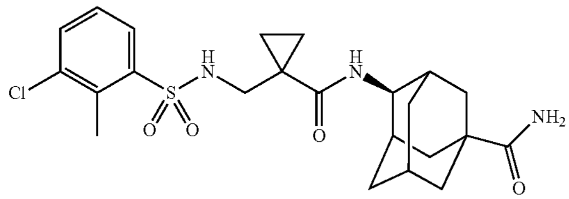 | $^{1}$H NMR (400 MHz, CDCl$_3$) d 7.90 (d, J = 8.0 Hz, 1H), 7.59 (d, J = 8.0 Hz, 1H), 7.27 (t, J = 8.0 Hz, 1H), 6.27 (d, J = 7.6 Hz, 1H), 5.69 (t, J = 6.4 Hz, 1H), 5.62 (brs, 1H), 5.37 (brs, 1H), 4.02 (t, J = 3.4 Hz, 1H), 3.06 (d, J = 6.4 Hz, 2H), 2.70 (s, 3H), 1.98-2.06 (m, 7H), 1.90 (s, 2H), 1.86 (d, J = 13.6 Hz, 2H), 1.61 (d, J = 13.6 Hz, 2H), 1.14-1.16 (m, 2H), 0.71-0.73 (m, 2H) |
| 6 | Z-4-[1-((3-chloro-2-methyl-benzenesulfonylamino)methyl)cyclopropane carboxamido]-adamanta-1-carboxylic acid amide | 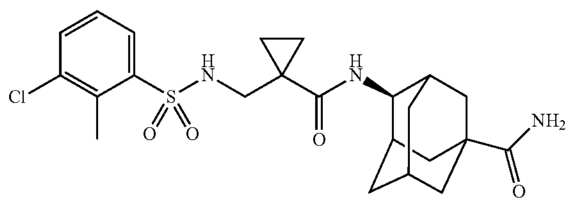 | $^{1}$H NMR (400 MHz, CDCl$_3$) d 7.89 (t, J = 6.2 Hz, 1H), 7.62 (t, J = 6.6 Hz, 1H), 7.26-7.31 (m, 2H), 6.85 (s, 1H), 6.23 (brs, 1H), 5.48 (brs, 1H), 4.08 (s, 1H), 3.07-3.08 (m, 2H), 2.70-2.75 (m, 3H), 1.54-2.17 (m, 13H), 1.26-1.27 (m, 2H), 0.67-0.72 (m, 2H) |
| 7 | E-4-[1-((3-chloro-benzenesulfonylamino)methyl)cyclopropane carboxamido]-adamantan-1-carboxylic acid amide | 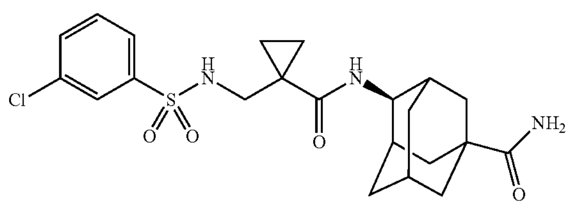 | $^{1}$H NMR (400 MHz, CDCl$_3$) d 7.86 (t, J = 1.8 Hz, 1H), 7.75-7.77 (m, 1H), 7.58-7.60 (m, 1H), 7.50 (t, J = 8.0 Hz, 1H), 6.62 (d, J = 7.6 Hz, 1H), 5.96 (t, J = 6.4 Hz, 1H), 5.72 (brs, 1H), 5.51 (brs, 1H), 4.06 (d, J = 6.8 Hz, 1H), 3.11 (d, J = 6.4 Hz, 2H), 1.92-2.09 (m, 11H), 1.64 (d, J = 12.8 Hz, 2H), 1.22-1.24 (m, 2H), 0.71-0.73 (m, 2H) |
| 8 | E-4-[1-((3-chloro-2-fluoro-benzenesulfonylamino)methyl)cyclopropane carboxamido]-adamantan-1-carboxylic acid amide | 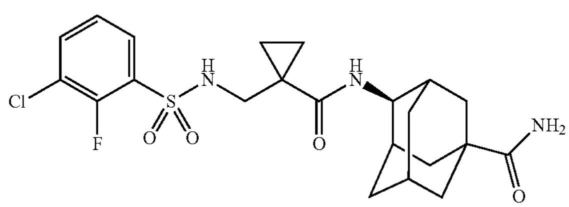 | $^{1}$H NMR (400 MHz, CDCl$_3$) d 7.78-7.82 (m, 1H), 7.63-7.67 (m, 1H), 7.23-7.28 (m, 1H), 6.39 (d, J = 7.2 Hz, 1H), 5.61-5.63 (m, 2H), 5.30 (brs, 1H), 4.05 (d, J = 7.2 Hz, 1H), 3.19 (d, J = 5.2 Hz, 2H), 1.88-2.08 (m, 11H), 1.62 (d, J = 13.6 Hz, 2H), 1.20-1.22 (m, 2H), 0.73-0.75 (m, 2H) |
| 9 | E-4-[1-((3,5-difluoro-benzenesulfonylamino)methyl)cyclopropane carboxamido]-adamantan-1-carboxylic acid amide | 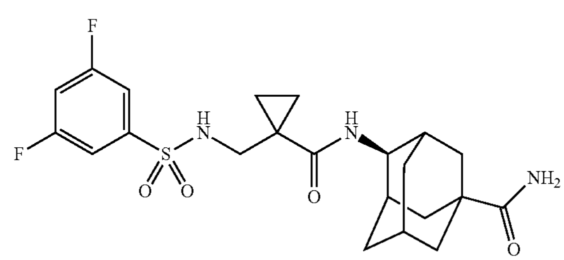 | $^{1}$H NMR (400 MHz, CDCl$_3$) d 7.40-7.42 (m, 2H), 7.02-7.07 (m, 1H), 6.67 (t, J = 6.2 Hz, 1H), 6.61 (d, J = 7.6 Hz, 1H), 5.82 (brs, 1H), 5.73 (brs, 1H), 4.05 (d, J = 7.2 Hz, 1H), 3.09 (d, J = 6.4 Hz, 2H), 1.19-2.07 (m, 11H), 1.62 (d, J = 12.8 Hz, 2H), 1.20-1.23 (m, 2H), 0.72-0.74 (m, 2H) |

TABLE 1-continued

| Example | Compound Name | Structure | NMR data |
|---|---|---|---|
| 10 | E-4-[1-((2-fluoro-6-methyl-benzenesulfonylamino)methyl)cyclopropane carboxamido]-adamanta-1-carboxylic acid amide | 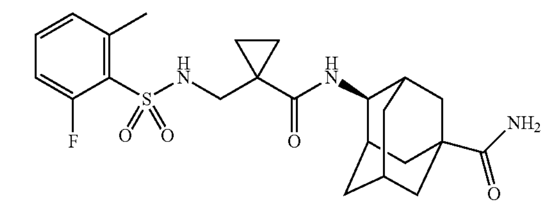 | $^1$H NMR (400 MHz, CDCl$_3$) d 7.40-7.45 (m, 1H), 7.13 (d, J = 8.0 Hz, 1H), 7.06 (dd, J = 10.8, 8.4 Hz, 1H), 6.79 (d, J = 7.6 Hz, 1H), 5.63 (brs, 1H), 5.58 (s, 1H), 5.50 (brs, 1H), 4.07 (d, J = 7.2 Hz, 1H), 3.14 (d, J = 6.8 Hz, 2H), 2.69 (s, 3H), 2.10 (s, 2H), 1.82-2.06 (m, 9H), 1.63 (d, J = 12.8 Hz, 2H), 1.25-1.27 (m, 2H), 0.66-0.68 (m, 2H) |
| 11 | E-4-[1-((2,3-difluoro-benzenesulfonylamino)methyl)cyclopropane carboxamido]-adamantan-1-carboxylic acid amide | 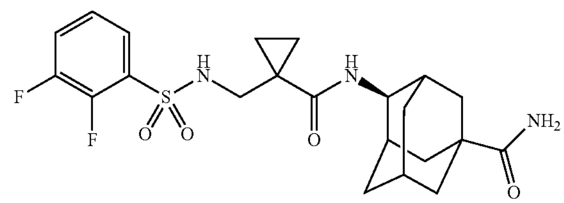 | $^1$H NMR (400 MHz, CDCl$_3$) d 7.64-7.68 (m, 1H), 7.39-7.47 (m, 1H), 7.23-7.28 (m, 1H), 6.51 (d, J = 7.2 Hz, 1H), 6.06 (t, J = 6.2 Hz, 1H), 5.75 (brs, 1H), 5.63 (brs, 1H), 4.05 (d, J = 7.2 Hz, 1H), 3.19 (d, J = 6.4 Hz, 2H), 1.90-2.07 (m, 11H), 1.61 (d, J = 12.8 Hz, 2H), 1.20-1.23 (m, 2H), 0.73-0.76 (m, 2H) |
| 12 | E-4-[1-((2,4,6-trifluoro-benzenesulfonylamino)methyl)cyclopropane carboxamido]-adamantan-1-carboxylic acid amide | 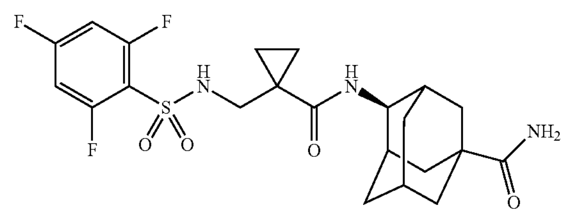 | $^1$H NMR (400 MHz, CDCl$_3$) d 6.80-6.85 (m, 2H), 6.26 (d, J = 7.6 Hz, 1H), 5.81 (t, J = 6.2 Hz, 1H), 5.59 (brs, 1H), 5.30 (brs, 1H), 4.04 (d, J = 7.6 Hz, 1H), 3.23 (d, J = 6.0 Hz, 2H), 1.85-2.07 (m, 11H), 1.62 (d, J = 13.2 Hz, 2H), 1.20-1.23 (m, 2H), 0.78-0.81 (m, 2H) |
| 13 | E-4-[1-((2-fluoro-N,6-dimethyl-benzenesulfonylamino)methyl)cyclopropane carboxamido]-adamantan-1-carboxylic acid amide | 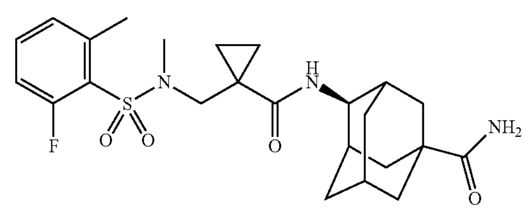 | $^1$H NMR (400 MHz, CDCl$_3$) d 7.30-7.44 (m, 1H), 7.23-7.25 (m, 1H), 7.13 (d, J = 7.6 Hz, 1H), 7.02-7.06 (m, 1H), 5.93 (brs, 1H), 5.64 (brs, 1H), 4.10 (d, J = 7.2 Hz, 1H), 3.40 (s, 2H), 2.94 (d, J = 2.4 Hz, 3H), 2.71 (s, 3H), 2.08-2.13 (m, 4H), 1.98-2.04 (m, 5H), 1.90-1.95 (m, 2H), 1.60 (d, J = 11.2 Hz, 2H), 1.38-1.41 (m, 2H), 0.60-0.63 (m, 2H) |
| 14 | E-4-[1-((2,4-dichloro-5-methyl-benzenesulfonylamino)methyl)cyclopropane carboxamido]-adamantan-1-carboxylic acid amide | 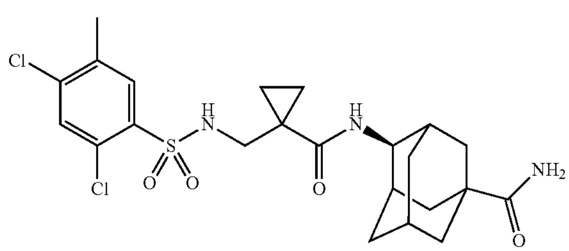 | $^1$H NMR (400 MHz, CDCl$_3$) d 7.94 (s, 1H), 7.54 (s, 1H), 6.58 (d, J = 8 Hz, 1H), 5.59 (t, J = 6.4 Hz, 2H), 5.46 (s, 1H), 4.07-4.06 (m, 1H), 3.00 (d, J = 6.4 Hz, 2H), 2.42 (s, 3H), 2.09-1.92 (m, 11H), 1.64 (d, J = 6.6 Hz, 2H), 1.25-1.22 (m, 2H), 0.68-0.66 (m, 2H) |

TABLE 1-continued

| Example | Compound Name | Structure | NMR data |
|---|---|---|---|
| 15 | E-4-[1-((4-chloro-2-fluoro-5-methyl-benzenesulfonylamino)methyl)cyclopropane carboxamido]-adamantan-1-carboxylic acid amide | 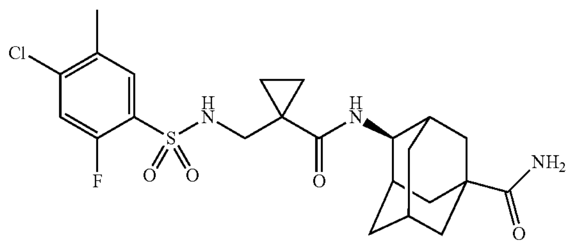 | $^1$H NMR (400 MHz, CDCl$_3$) d 7.74 (d, J = 7.6 Hz, 1H), 7.26 (d, J = 9.6 Hz,, 1H), 6.51 (d, J = 7.6 Hz, 1H), 5.62 (s, 1H), 5.51 (t, J = 6.4 Hz, 1H), 5.34 (s, 1H), 4.06-4.06 (m, 1H), 3.12 (d, J = 6.4 Hz, 2H), 2.40 (s, 3H), 2.08-1.91 (m, 11H), 1.63 (d, J = 12 Hz, 2H), 1.24-1.21 (m, 2H), 0.72-0.69 (m, 2H) |
| 16 | E-4-[1-((4,5-dichloro-2-fluoro-benzenesulfonylamino)methyl)cyclopropane carboxamido]-adamantan-1-carboxylic acid amide | 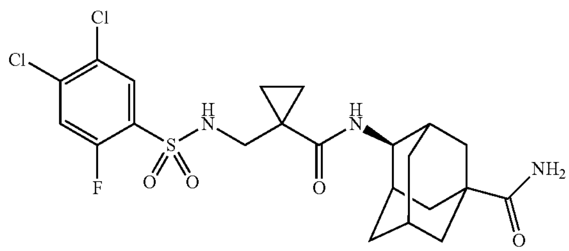 | $^1$H NMR (400 MHz, CDCl$_3$) d 7.98 (d, J = 6.8 Hz, 1H), 7.38 (d, J = 9.2 Hz, 1H), 6.20 (d, J = 7.2 Hz, 1H), 5.68 (t, J = 6.4 Hz, 1H), 5.60 (s, 1H), 5.46 (s, 1H), 4.04-4.03 (m, 1H), 3.16 (d, J = 6.4 Hz, 2H), 2.07-1.83 (m, 11H), 1.64-1.59 (d, J = 18.4 Hz, 2H), 1.21-1.18 (m, 2H), 0.80-0.77 (m, 2H) |
| 17 | E-4-[1-((furan-2-sulfonylamino)methyl)cyclopropane-carboxamido]-adamantan-1-carboxylic acid amide | 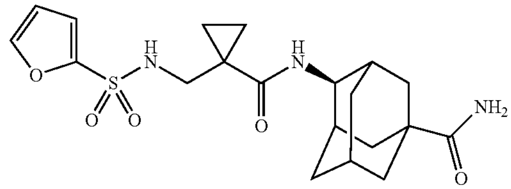 | $^1$H NMR (400 MHz, CDCl$_3$) d 7.58 (dd, J = 1.8, 0.8 Hz, 1H), 7.07 (dd, J = 3.6, 0.8 Hz, 1H), 6.53 (dd, J = 3.2, 1.6 Hz, 1H), 6.47 (d, J = 7.6 Hz, 1H), 5.60 (s, 1H), 5.41 (t, J = 6.4 Hz, 1H), 5.28 (s, 1H), 4.06-4.04 (m, 1H), 3.20 (d, J = 6.8 Hz, 2H), 2.07-1.90 (m, 11H), 1.61 (d, J = 18.8 Hz, 2H), 1.25-1.20 (m, 2H), 0.75-0.72 (m, 2H) |
| 18 | E-4-[1-(3,5-dichloro-benzenesulfonylamino)methyl)cyclopropane carboxamido]-adamantan-1-carboxylic acid amide | 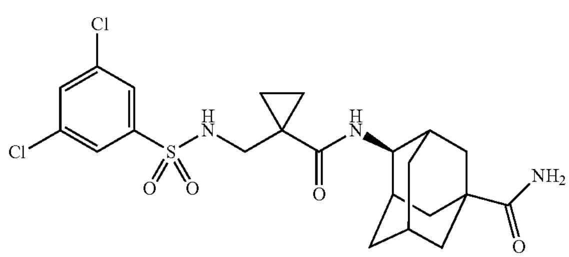 | $^1$H NMR (400 MHz, DMSO) d 8.04 (s, 1H), 7.87 (s, 1H), 7.87 (s, 1H), 7.15-7.06 (m, 2H), 6.81 (s, 1H), 3.88-3.87 (m, 1H), 3.23 (d, J = 4.4 Hz, 1H), 3.16 (s, 2H), 2.06-1.82 (m, 11H), 1.50 (d, J = 12.4 Hz, 2H), 1.04-0.98 (m, 2H), 0.75-0.70 (m, 2H) |
| 19 | E-4-[1-((thiophen-2-sulfonylamino)methyl)cyclopropane-carboxamido]-adamantan-1-carboxylic acid amide | 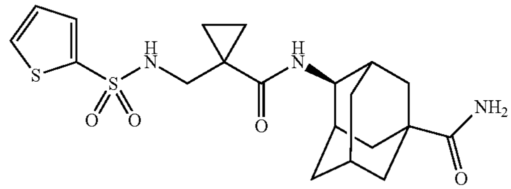 | $^1$H NMR (400 MHz, CDCl$_3$) d 7.64-7.62 (m, 2H), 7.14-7.12 (m, 1H), 6.54 (d, J = 7.6 Hz, 1H), 5.56 (s, 1H), 5.19 (s, 1H), 5.03 (t, J = 6.6 Hz, 1H), 4.06-4.03 (m, 1H), 3.16 (d, J = 6.8 Hz, 2H), 2.08-1.91 (m, 11H), 1.62 (d, J = 13.2 Hz, 2H), 1.25-1.23 (m, 2H), 0.71-0.70 (m, 2H) |

TABLE 1-continued

| Example | Compound Name | Structure | NMR data |
|---|---|---|---|
| 20 | E-4-[1-((2-(trifluoromethyl)-4-fluorobenzenesulfonylamino)methyl)cyclopropane carboxamido]-adamantan-1-carboxylic acid amide | 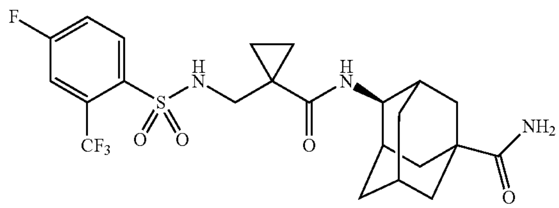 | H NMR (400 MHz, CDCl₃) d 8.25 (dd, J = 8.8, 5.2 Hz, 1H), 7.61 (dd, J = 8.8, 2.4 Hz, 1H), 7.43-7.39 (m, 1H), 6.47 (d, J = 7.6 Hz, 1H), 5.64 (s, 1H), 5.54 (t, J = 6.2 Hz, 1H), 5.49 (s, 1H), 4.06-4.04 (m, 1H), 3.09 (d, J = 6 Hz, 2H), 2.08-1.90 (m, 11H), 1.67-1.61 (m, 2H), 1.24-1.21 (m, 2H), 0.71-0.68 (m, 2H) |
| 21 | E-4-[1-((3,4-difluorobenzenesulfonylamino)methyl)cyclopropane carboxamido]-adamantan-1-carboxylic acid amide | 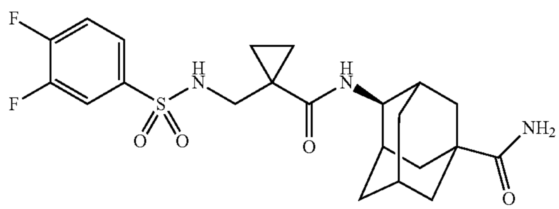 | ¹H NMR (400 MHz, CDCl₃) d 7.73-7.68 (m, 1H), 7.66-7.63 (m, 1H), 7.37-7.30 (m, 1H), 6.42 (d, J = 5.6 Hz, 1H), 5.76 (s, 1H), 5.66 (s, 1H), 5.42 (s, 1H), 4.04 (s, 1H), 3.08 (d, J = 6 Hz, 2H), 2.07-1.91 (m, 11H), 1.72-1.61 (m, 2H), 1.22-1.19 (m, 2H), 0.76-0.72 (m, 2H) |
| 22 | E-4-[1-((2-fluoro-N-methylbenzenesulfonylamino)methyl)cyclopropane carboxamido]-adamantan-1-carboxylic acid amide | 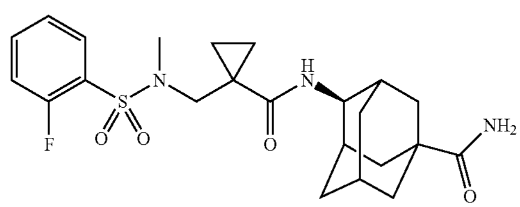 | ¹H NMR (400 MHz, CDCl₃) d 7.86-7.90 (m, 1H), 7.61-7.66 (m, 1H), 7.34 (t, J = 7.6 Hz, 1H), 7.23-7.26 (m, 2H), 6.05 (brs, 1H), 6.83 (brs, 1H), 4.10 (d, J = 7.2 Hz, 1H), 3.31 (s, 2H), 2.90 (d, J = 2.0 Hz, 3H), 1.90-2.12 (m, 11H), 1.61 (d, J = 12.0 Hz, 2H), 1.36-1.38 (m, 2H), 0.57-0.60 (m, 2H) |
| 23 | E-4-[1-((4-trifluoromethoxybenzenesulfonylamino)methyl)cyclopropane carboxamido]-adamantan-1-carboxylic acid amide | 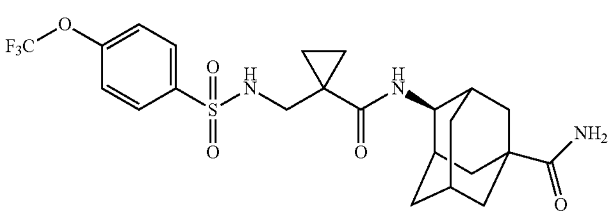 | H NMR (400 MHz, DMSO) d 8.14 (brs, 1H), 7.96 (m, 2H), 7.61 (d, J = 8.4 Hz, 2H), 7.10 (d, J = 6.8 Hz, 1H), 7.01 (brs, 1H), 6.74 (brs, 1H), 3.85 (m, 1H), 3.04 (s, 2H), 2.00 (d, J = 12.4 Hz, 1H), 1.91-1.76 (m, 9H), 1.45 (d, J = 12.4 Hz, 2H), 0.95 (m, 2H), 0.64 (m, 2H) |
| 24 | E-4-[1-((2,3-difluorobenzeneamino)methyl)cyclopropanecarboxamido]-adamantan-1-carboxylic acid amide | 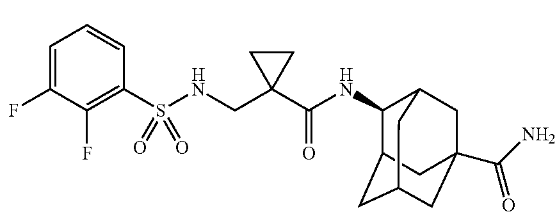 | ¹H NMR (400 MHz, DMSO) d 8.95 (t, J = 6 Hz, 1H), 7.71 (d, J = 6.8 Hz, 1H), 7.62-7.56 (m, 1H), 7.38-7.29 (m, 2H), 7.02 (s, 1H), 6.72 (s, 1H), 4.18 (s, 1H), 3.17 (d, J = 4.4 Hz, 2H), 2.02-1.73 (m, 11H), 1.40 (d, J = 11.6 Hz, 2H), 1.03-1.01 (m, 2H), 0.84-0.82 (m, 2H) |

TABLE 1-continued

| Example | Compound Name | Structure | NMR data |
|---|---|---|---|
| 25 | E-4-[1-((3,4-difluoro-benzeneamino)methyl)cyclopropane-carboxamido]-adamantan-1-carboxylic acid amide | 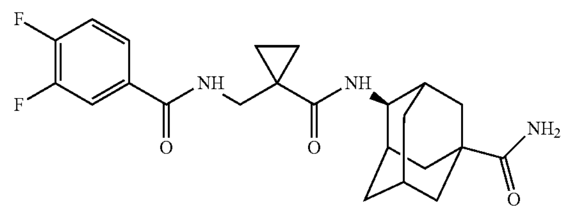 | ¹H NMR (400 MHz, DMSO) d 8.96 (t, J = 6 Hz, 1H), 7.93 (t, J = 9.6 Hz, 1H), 7.85 (d, J = 6.8 Hz, 1H), 7.64-7.58 (m, 1H), 6.97 (s, 1H), 6.70 (s, 1H), 3.81-3.79 (m, 1H), 3.60 (d, J = 6.4 Hz, 2H), 2.01-1.73 (m, 11H), 1.39 (d, J = 12.4 Hz, 2H), 1.04-1.02 (m, 2H), 0.87-0.85 (m, 2H) |
| 26 | E-4-[1-((1-methyl-1H-indole-5-sulfonylamino)methyl)cyclopropane-carboxamido]-adamantan-1-carboxylic acid amide | 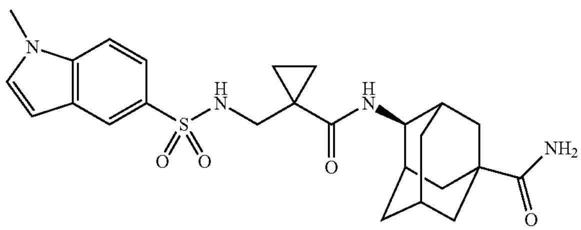 | ¹H NMR (400 MHz, DOS) d 8.08 (d, J = 1.6 Hz, 1H), 7.82 (t, J = 6.2 Hz, 1H), 7.65 (d, J = 8.8 Hz, 1H), 7.59 (dd, J = 8.8, 1.6 Hz, 1H), 7.53 (d, J = 3.2 Hz, 1H), 7.27 (d, J = 7.6 Hz, 1H), 7.01 (s, 1H), 6.73 (s, 1H), 6.64 (d, J = 2.8 Hz, 1H), 3.85 (s, 3H), 2.90 (d, J = 6 Hz, 2H), 2.08-1.78 (m, 11H), 1.48 (d, J = 12.8 Hz, 2H), 0.94 (m, 2H), 0.60-0.57 (m, 2H) |
| 27 | E-4-[1-((1-methyl-1H-pyrazole-5-sulfonylamino)methyl)cyclopropane-carboxamido]-adamantan-1-carboxylic acid amide | 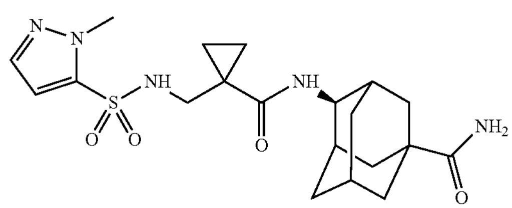 | ¹H NMR (400 MHz, DMSO) d 7.55 (d, J = 2 Hz, 1H), 7.16 (d, J = 8 Hz, 1H), 7.03 (s, 1H), 6.74 (d, J = 2.4 Hz, 2H), 3.95 (s, 3H), 3.72 (d, J = 7.2 Hz, 1H), 1.93 (s, 1H), 1.83-1.81 (m, 8H), 1.76-1.75 (m, 2H), 1.49 (d, J = 12.4 Hz, 2H), 1.20-1.17 (m, 2H), 0.88-0.85 (m, 2H) |
| 28 | E-4-[1-((benzenesulfonylamino)methyl)cyclopropane-carboxamido]-adamantan-1-carboxylic acid amide | 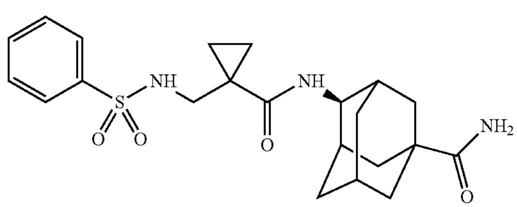 | ¹H NMR (400 MHz, DMSO) d 8.05 (s, 1H), 7.83 (d, J = 8 Hz, 2H), 7.69-7.60 (m, 3H), 7.17 (s, 1H), 7.01 (s, 1H), 6.73 (s, 1H), 3.87-3.86 (m, 1H), 2.99 (s, 2H), 2.03 (d, J = 13.2 Hz, 2H), 1.91 (s, 3H), 1.83 (s, 4H) 1.77 (s, 2H), 1.46 (d, J = 13.6 Hz, 2H), 0.96-0.94 (m, 2H), 0.64-0.62 (m, 2H) |
| 29 | E-4-[1-((2-fluoro-benzenesulfonylamino)methyl)cyclopropane carboxamido]-adamantan-1-carboxylic acid | 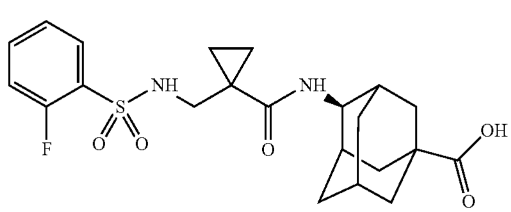 | ¹H NMR (400 MHz, MeOD) d 7.91-7.87 (m, 1H), 7.70-7.66 (m, 1H), 7.48-7.43 (m, 1H), 7.39-7.30 (m, 2H), 4.00 (s, 1H), 3.16 (s, 2H), 2.17-1.85 (m, 11H), 1.61 (d, J = 12.8 Hz, 2H), 1.15-1.13 (m, 2H), 0.72-0.70 (m, 2H) |

TABLE 1-continued

| Example | Compound Name | Structure | NMR data |
|---|---|---|---|
| 30 | N-(bicyclo[2.2.1]heptan-2-yl)-1-((2-fluoro-N-methylbenzenesulfonylamino)methyl)cyclopropanecarboxamido | 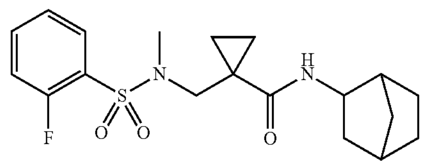 [SMILES: CN(CC1(C(=O)NC2CC3CCC2C3)CC1)S(=O)(=O)c1ccccc1F] | H NMR (400 MHz, CDCl₃) d 7.90 (t, J = 7.0 Hz, 1H), 7.61 (d, J = 5.6 Hz, 1H), 7.32 (t, J = 7.4 Hz, 1H), 7.24 (t, J = 10.0 Hz, 1H), 7.08 (s, 1H), 4.15 (d, J = 4.0 Hz, 1H), 3.44 (d, J = 14.4 Hz, 1H), 3.11 (d, J = 14.4 Hz, 1H), 2.93 (s, 3H), 2.48 (s, 1H), 2.22 (s, 1H), 2.02-2.08 (m, 1H), 1.60-1.74 (m, 3H), 1.26-1.45 (m, 5H), 1.00 (d, J = 12.4 Hz, 1H), 0.56 (s, 2H) |
| 31 | N-(adamantan-1-yl)-1-((2-fluoro-N-methylbenzenesulfonylamino)methyl)cyclopropanecarboxamido | 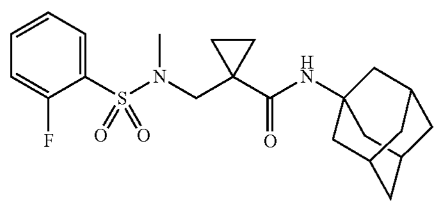 [SMILES: CN(CC1(C(=O)NC23CC4CC(CC(C4)C2)C3)CC1)S(=O)(=O)c1ccccc1F] | $^1$H NMR (400 MHz, CDCl₃) d 7.88 (t, J = 7.4 Hz, 1H), 7.58-7.63 (m, 1H), 7.31 (t, J = 7.7 Hz, 1H), 7.23 (t, J = 9.2 Hz, 1H), 6.62 (s, 1H), 3.24 (s, 2H), 2.90 (d, J = 2.0 Hz, 3H), 2.07 (s, 9H), 1.65-1.73 (m, 6H), 1.28-1.31 (m, 2H), 0.51-0.53 (m, 2H) |
| 32 | E-4-[1-((N-ethyl-fluoro-benzenesulfonylamino)methyl)cyclopropane carboxamido]-adamantan-1-carboxylic acid amide | 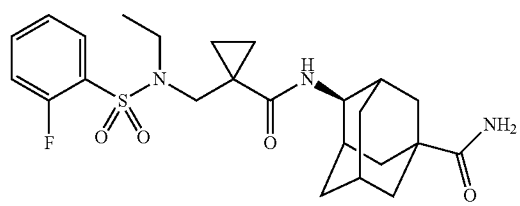 | $^1$H NMR (400 MHz, CDCl₃) d 7.92 (m, 1H), 7.59 (m, 1H), 7.32 (td, J₁ = 1.2 Hz, J₂ = 6.4 Hz, 1H), 7.22 (m, 2H), 5.63 (brs, 1H), 5.43 (brs, 1H), 4.12 (d, J = 5.6 Hz, 1H), 3.52 (s, 2H), 3.32 (m, 2H), 2.18-1.86 (m, 13H), 1.39 (m, 2H), 1.12 (t, J = 6.8 3H), 0.65 (m, 2H) |
| 33 | E-3-(4-(1((2-fluoro-benzenesulfonylamino)methyl)cyclopropane carboxamido)adamantan-1-yl)propanoic acid | 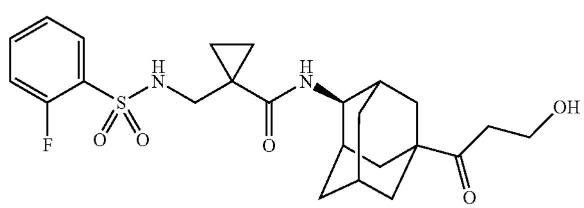 | $^1$H NMR (400 MHz, MeOD) d 7.86-7.94 (m, 1H), 7.65-7.70 (m, 1H), 7.30-7.43 (m, 2H), 3.94 (s, 1H), 3.65 (s, 1H), 2.23-2.32 (m, 2H), 2.13 (d, J = 13.2 Hz, 2H), 1.92-2.01 (m, 2H), 1.53-1.61 (m, 9H), 1.42-1.46 (m, 2H), 1.12-1.15 (m, 2H), 0.68-0.71 (m, 2H) |
| 34 | E-N-(5-(3-amino-3-oxopropyl)adamantan-2-yl)-1-((2-fluoro-benzenesulfonylamino)methyl)cyclopropane carboxamido | 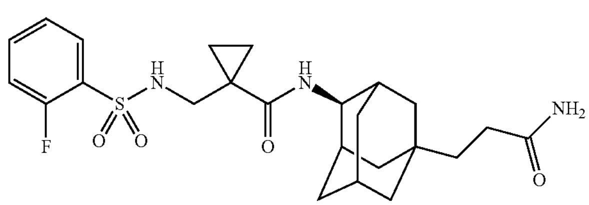 | $^1$H NMR (400 MHz, DMSO) d 7.88-7.92 (m, 1H), 7.58-7.64 (m, 1H), 7.31 (t, J = 7.6 Hz, 1H), 7.21-7.25 (m, 1H), 6.47 (d, J = 7.6 Hz, 1H), 5.62 (brs, 1H), 5.45-5.48 (m, 2H), 3.98 (d, J = 7.2 Hz, 1H), 3.12 (t, J = 6.4 Hz, 2H), 2.16-2.20 (m, 2H), 1.98 (s, 2H), 1.87 (d, J = 13.6 Hz, 2H), 1.46-1.62 (m, 11H), 1.18-1.21 (m, 2H), 0.68-0.71 (m, 2H) |

TABLE 1-continued

| Example | Compound Name | Structure | NMR data |
|---|---|---|---|
| 35 | E-N-(5-aminoadamantan-2-yl)-1-((2-fluorobenzenesulfonylamino)methyl)cyclopropane carboxamide hydrochloride | 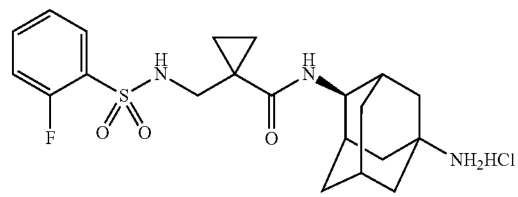 | $^1$H NMR (400 MHz, D$_2$O) d 7.79 (dt, J = 7.6, 1.6 Hz, 1H), 7.64-7.70 (m, 1H), 7.27-7.35 (m, 2H), 3.75 (s, 1H), 3.15 (s, 2H), 1.88-2.10 (m, 11H), 1.48 (d, J = 13.6 Hz, 2H), 0.99-1.02 (m, 2H), 0.66-0.69 (m, 2H) |
| 36 | E-4-[1-((2,4,5-trifluorobenzenesulfonylamino)methyl)cyclopropane carboxamido]-adamantan-1-carboxylic acid amide | 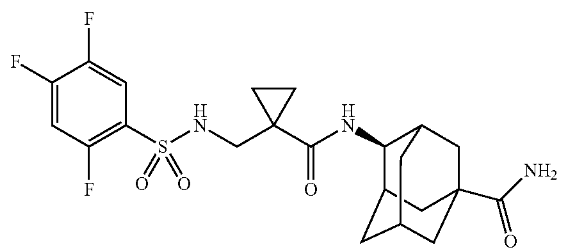 | $^1$H NMR (400 MHz, CDCl$_3$) d 7.73-7.79 (m, 1H), 7.08-7.14 (m, 1H), 6.18 (d, J = 7.6 Hz, 1H), 5.55 (t, J = 6.4 Hz, 1H), 5.21 (brs, 1H), 4.03 (d, J = 7.2 Hz, 1H), 3.15 (d, J = 6.4 Hz, 2H), 1.99-2.07 (m, 7H), 1.91 (s, 2H), 1.85 (d, J = 13.2 Hz, 2H), 1.63 (d, J = 13.2 Hz, 2H), 1.19-1.22 (m, 2H), 0.77-0.80 (m, 2H) |
| 37 | E-4-[1-((4-chlorobenzenesulfonylamino)methyl)cyclopropane carboxamido]-adamantan-1-carboxylic acid amide | 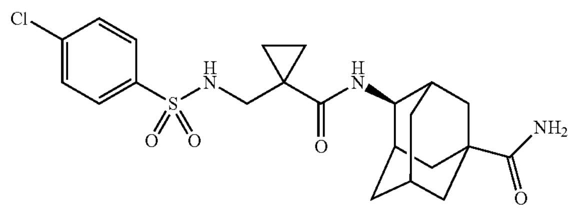 | $^1$H NMR (400 MHz, DMSO) d 8.11 (t, J = 6.4 Hz, 1H), 7.85-7.81 (m, 2H), 7.71-7.68 (m, 2H), 7.08 (d, J = 7.6 Hz, 1H), 7.00 (s, 1H), 6.73 (s, 1H), 3.86-3.84 (m, 1H), 3.01 (d, J = 6.4 Hz, 2H), 2.02-1.76 (m, 11H), 1.46 (d, J = 12.8 Hz, 2H), 0.97-0.94 (m, 2H), 0.65-0.63 (m, 2H) |

Preparational Example 13

Preparation of 1-aminocyclopropyl acetic acid hydrochloride

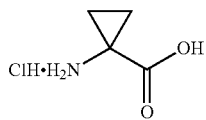

After reducing pressure in the reaction vessel, the vessel was filled with nitrogen gas, to which 6.8 ml of 7 N NH$_3$ in MeOH was loaded. 1.0 g (6.30 mmol) of dimethylcyclopropane-1,1-dicarboxylate was dissolved in 63 ml of MeOH, which was also loaded into the reaction vessel. If the starting material still remained, NH$_3$ gas could be provided for bubbling for 15 minutes. Upon completion of the reaction, the reaction solvent was eliminated by evaporation under reduced pressure and the precipitated solid compound was filtered and washed with 0° C. methanol, followed by vacuum drying. The obtained reaction product was dissolved in 5 ml of 7.4% NaOH/H$_2$O, followed by stirring at 40° C. for 20 minutes. Then, the temperature was lowered to room temperature (Reactant A). 7 ml of 12.3% NaOCl and 2 ml of 30% NaOH/H$_2$O were stirred together at room temperature for 1 hour (Reactant B). These reactants A and B were mixed and stirred at 80° C. for 4 minutes. After lowering the temperature thereof, 4 ml of hydrochloric acid was slowly added thereto carefully not to increase the temperature more than 60° C. The solvent was eliminated by evaporation under reduced pressure and the reactant was dissolved in ethanol. The precipitated solid compound was filtered. The remaining solution was evaporated under reduced pressure and then dissolved in hot acetone. The generated solid compound was filtered and dried to give 0.5 g of 1-aminocyclopropyl acetic acid hydrochloride (yield: 58%).

$^1$H NMR (400 MHz, D$_2$O) δ 1.40-1.43 (m, 2H), 1.22-1.25 (m, 2H)

Preparational Example 14

Preparation of 1-(t-butoxycarbonylamino)cyclopropyl acetic acid

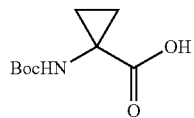

4.18 g (30.37 mmol) of the 1-aminocyclopropyl acetic acid hydrochloride prepared in Preparational Example 13 was dissolved in 61 ml of methylene chloride, to which 4.7 ml (33.40 mmol) of TEA was added. The mixture was stirred for 10 minutes and then methylene chloride was evaporated under reduced pressure. The reactant was dissolved in 36.5 ml of 1N NaOH solution and 101 ml of 1,4-dioxane, to which 8.4 ml (36.44 mmol) of Boc$_2$O was added. The reaction mixture was stirred at room temperature for 16 hours, and then 1,4-dioxane was evaporated under reduced pressure. The residue was acidized with 1N HCl to be pH 3, followed by extraction with 3100 ml of ethyl acetate. The extract was dried over anhydrous magnesium sulfate, followed by evaporation under reduced pressure to give 3.59 g of 1-(t-butoxycarbonylamino)cyclopropylacetic acid (yield: 59%).

$^1$H NMR (400 MHz, MeOD) δ 1.51 (s, 2H), 1.51 (s, 9H), 1.44 (s, 4H)

Preparational Example 15

Preparation of 4-[1-(t-butoxycarbonylamino)-cyclopropanecarboxamido]-adamantan-1-carboxylic acid methyl ester

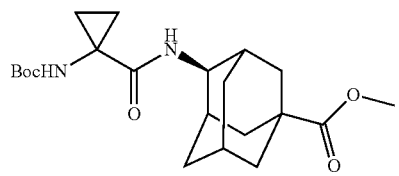

3.59 g (17.85 mmol) of the 1-(t-butoxycarbonylamino) cyclopropyl acetic acid prepared in Preparational Example 14 and 4.83 g (19.64 mmol) of the 4-amino-adamantan-1-carboxylic acid methyl ester prepared in Preparational Example 7 were dissolved in 60 ml of methylene chloride, to which 5.15 g (19.64 mmol) of BOP—Cl was added. 4.98 ml (35.70 mmol) of TEA was also added thereto. The mixture was stirred at room temperature for 16 hours and methylene chloride was evaporated under reduced pressure. The residue was dissolved in 50 ml of water, followed by extraction with 3100 ml of ethylacetate. The extract was dried over anhydrous magnesium sulfate, and evaporated under reduced pressure, followed by column chromatography to give 4.95 g of 4-[1-(t-butoxycarbonylamino)cyclopropanecarboxamido]-adamantan-1-carboxylic acid methyl ester (yield: 71%).

$^1$H NMR (400 MHz, CDCl$_3$) δ 7.27 (brs, 1H), 5.10 (brs, 1H), 4.00 (d, J=6.8 Hz, 1H), 3.66 (s, 3H), 1.90-2.05 (m, 9H), 1.80 (d, J=12.8 Hz, 2H), 1.60 (d, J=13.6 Hz, 2H), 1.53-1.56 (m, 2H), 1.47 (s, 9H). 0.98-1.01 (m, 2H)

Preparational Example 16

Preparation of 4-(1-aminocyclopropanylcarboxamido)-adamantan-1-carboxylic acid methyl ester hydrochloride

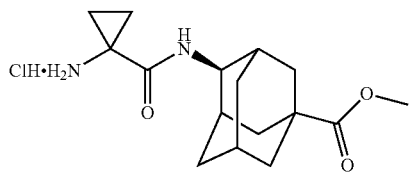

4.95 g (14.42 mmol) of the 4-[1-(t-butoxycarbonylamino)-cyclopropanecarboxamido]-adamantan-1-carboxylic acid methyl ester prepared in Preparational Example 15 was dissolved in 48 ml of ethyl acetate, to which 36 ml of 4M HCl 1,4-dioxane was added, followed by stirring at room temperature for 6 hours. Upon completion of the reaction, the reaction solvent was eliminated by evaporation under reduced pressure. The residue was dissolved in 50 ml of ethylene acetate and the precipitated solid compound was filtered. As a result, 4.1 g of 4-(1-aminocyclopropanylcarboxamido)-adamantan-1-carboxylic acid methyl ester hydrochloride was obtained (yield: 86%).

$^1$H NMR (400 MHz, D$_2$O) δ 3.79 (s, 1H), 3.56 (s, 3H), 3.08 (s, 2H), 1.86-1.95 (m, 7H), 1.71 (d, J=13.6 Hz, 2H), 1.40-1.46 (m, 4H), 1.30-1.33 (m, 2H)

Preparational Example 17

Preparation of 4-[1-(3-chlorobenzenesulfonylamino) cyclopropanecarboxamido]-adamantan-1-carboxylic acid methyl ester

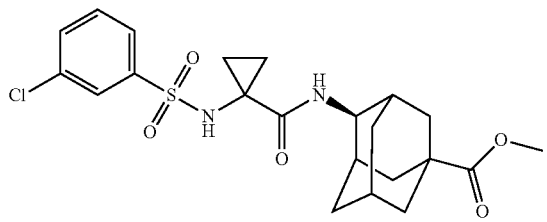

200 mg (0.61 mmol) of the 4-(1-aminocyclopropanylcarboxamido)-adamantan-1-carboxylic acid methyl ester hydrochloride prepared in Preparational Example 16 was dissolved in 2 ml of methylene chloride, to which 0.17 ml of TEA was added, followed by stirring at room temperature for 5 minutes. 142 mg (0.67 mmol) of 2-chlorosulfonylchloride was added to the reactant, which was then stirred at room temperature for 6 hours. The reaction solvent was eliminated by evaporation under reduced pressure. The residue was dissolved in 10 ml of water, followed by extraction with 330 ml of ethylacetate. The extract was dried over anhydrous magnesium sulfate, and evaporated under reduced pressure, followed by column chromatography to give 108 g of 4-[1-(3-chlorobenzenesulfonylamino)cyclopropanecarboxamido]-adamantan-1-carboxylic acid methyl ester (yield: 38%).

¹H NMR (400 MHz, CDCl₃) δ 7.85 (t, J=1.8 Hz, 1H), 7.75 (d, J=7.8 Hz, 1H), 7.60 (d, J=8.0 Hz, 1H), 7.49 (t, J=8.0 Hz, 1H), 7.18 (d, J=7.6 Hz, 1H), 5.44 (d, J=10.4 Hz, 1H), 3.98 (d, J=7.6 Hz, 1H), 3.66 (s, 3H), 1.89-2.05 (m, 10H), 1.64 (s, 1H), 1.59 (d, J=10.4 Hz, 2H), 1.44-1.48 (m, 2H), 0.82-0.85 (m, 2H)

Preparational Example 18

Preparation of 4-[1-(3-chlorobenzenesulfonylamino)cyclopropanecarboxamido]-adamantan-1-carboxylic acid

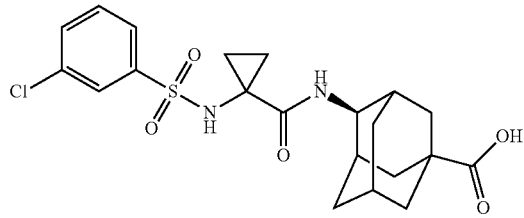

100 mg (0.21 mmol) of the 4-[1-(3-chlorobenzenesulfonylamino)cyclopropanecarboxamido]-adamantan-1-carboxylic acid methyl ester prepared in Preparational Example 17 was dissolved in 1.5 ml of THF/ethanol mixed solution, to which 1.5 ml of 2N NaOH solution was added, followed by stirring at room, temperature overnight. The residue was acidized with 1 N HCl, followed by extraction with ethyl acetate. The extract was dried over anhydrous magnesium sulfate, followed by evaporation under reduced pressure to give 96 mg of 4-[1-(3-chlorobenzenesulfonylamino)cyclopropanecarboxamido]-adamantan-1-carboxylic acid (yield: 98%).

¹H NMR (400 MHz, MeOD) δ 8.98 (s, 1H), 7.72-7.78 (m, 3H), 7.62-7.66 (m, 1H), 7.14 (d, J=7.6 Hz, 1H), 3.61 (d, J=6.8 Hz, 1H), 1.75-2.01 (m, 11H), 1.47 (d, J=12.8 Hz, 2H), 1.16-1.19 (m, 2H), 0.88-0.91 (m, 11H)

Example 38

Preparation of E-4-[1-(3-chlorobenzenesulfonylamino)cyclopropanecarboxamido]-adamantan-1-carboxylic acid amide

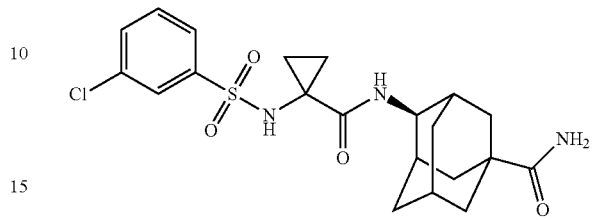

96 mg (0.21 mmol) of the 4-[1-(3-chlorobenzenesulfonylamino)cyclopropanecarboxamido]-adamantan-1-carboxylic acid prepared in Preparational Example 18 was dissolved in 1 ml of acetonitrile, to which 34 mg (0.25 mmol) of HOBt, 48 mg (0.25 mmol) of EDCI, and 60 ml (0.42 mmol) of TEA were added. The mixture was stirred at room temperature for 10 minutes, to which 13 mg (0.25 mmol) of ammonium chloride was added, followed by stirring at room temperature for 20 hours. Upon completion of the reaction, the reaction solvent was eliminated by evaporation under reduced pressure and the reactant was dissolved in 60 ml of methylene chloride. The organic layer was washed with 1 N HCl (2×2 ml) and then washed again with brine. The reaction product was dried over anhydrous magnesium sulfate, followed by column chromatography to give 41 mg of E-4-[1-(3-chlorobenzenesulfonylamino)cyclopropanecarboxamido]-adamantan-1-carboxylic acid amide (yield: 43%).

¹H NMR (400 MHz, CDCl₃) δ 7.84 (t, J=2.0 Hz, 1H), 7.75 (dt, J=7.2, 1.2 Hz, 1H), 7.59 (m, 1H), 7.49 (t, J=8.0 Hz, 1H), 7.22 (d, J=8.0 Hz, 1H), 5.75 (s, 1H), 5.62 (brs, 1H), 5.35 (brs, 1H), 3.99 (t, J=7.6 Hz, 1H), 2.08 (s, 3H), 1.92-1.99 (m, 8H), 1.63 (d, J=12.8 Hz, 2H), 1.45-1.48 (m, 2H), 0.82-0.85 (m, 2H)

The compounds of Example 39-Example 66 were prepared by the preparation method described in Example 38.

TABLE 2

| Example | Compound Name | Structure | NMR data |
|---|---|---|---|
| 39 | E-4-[1-(2-fluoro-benzenesulfonylamino)cyclopropanecarboxamido]-adamantan-1-carboxylic acid amide | 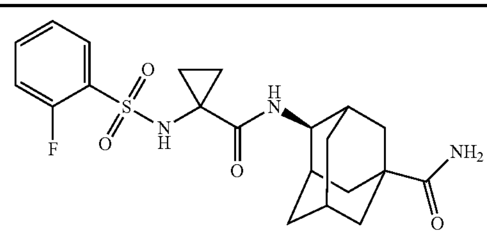 | ¹H NMR (400 MHz, CDCl₃) d 7.92 (dt, J = 1.6, 7.6 Hz, 1H), 7.63-7.65 (m, 1H), 7.34 (t, J = 7.6 Hz, 2H), 7.22-7.26 (m, 1H), 5.58 (brs, 1H), 5.52 (s, 1H), 5.22 (brs, 1H), 4.02 (d, J = 7.6 Hz, 1H), 3.65-3.66 (m, 2H), 1.93-2.11 (m, 11H), 1.65 (d, J = 13.6 Hz, 2H), 1.44-1.47 (m, 2H), 0.77-0.80 (m, 2H) |
| 40 | E-4-[1-(2-fluoro-6-methyl-benzenesulfonylamino)cyclopropanecarboxamido]-adamantan-1-carboxylic acid amide | 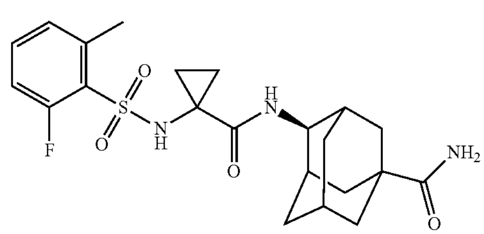 | ¹H NMR (400 MHz, CDCl₃) d 7.90 (d, J = 8.0 Hz, 1H), 7.59 (d, J = 8.0 Hz, 1H), 7.27 (t, J = 8.0 Hz, 1H), 6.27 (d, J = 7.6 Hz, 1H), 5.69 (t, J = 6.4 Hz, 1H), 5.62 (brs, 1H), 5.37 (brs, 1H), 4.02 (t, J = 3.4 Hz, 1H), 3.06 (d, J = 6.4 Hz, 2H), 2.70 (s, 3H), 1.98-2.06 (m, 7H), 1.90 (s, 2H), 1.86 (d, J = 13.6 Hz, 2H), 1.61 (d, J = 13.6 Hz, 2H), 1.14-1.16 (m, 2H), 0.71-0.73 (m, 2H) |

TABLE 2-continued

| Example | Compound Name | Structure | NMR data |
|---|---|---|---|
| 41 | E-4-[1-(3-chloro-2-methyl-benzenesulfonylamino)cyclopropanecarboxamido]-adamantan-1-carboxylic acid amide | 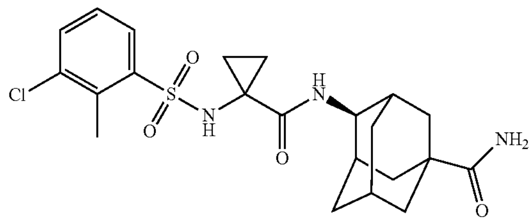 | ¹H NMR (400 MHz, CDCl₃) d 7.93 (d, J = 7.6 Hz, 1H), 7.63 (d, J = 7.6 Hz, 1H), 7.37-7.40 (m, 1H), 7.30 (t, J = 8.0 Hz, 1H), 6.11 (brs, 2H), 5.77 (brs, 1H), 4.00 (d, J = 4.8 Hz, 1H), 2.63 (s, 3H), 1.91-2.09 (m, 11H), 1.63 (d, J = 12.8 Hz, 2H), 1.37-1.40 (m, H), 0.71-0.74 (m, 2H) |
| 42 | E-4-[1-(4-fluoro-benzenesulfonylamino)cyclopropanecarboxamido]-adamantan-1-carboxylic acid amide | 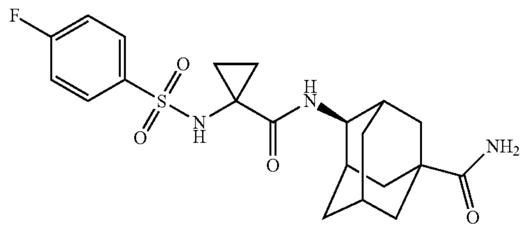 | ¹H NMR (400 MHz, DMSO) d 7.82-7.85 (m, 2H), 7.45 (t, J = 8.8 Hz, 2H), 7.19 (d, J = 7.6 Hz, 1H), 7.02 (brs, 1H), 6.74 (brs, 1H), 3.66 (d, J = 7.2 Hz, 1H), 1.91 (s, 1H), 1.75-1.84 (m, 9H), 1.46 (d, J = 12.0 Hz, 2H), 1.14-1.17 (m, 2H), 0.83-0.86 (m, 2H) |
| 43 | E-4-[1-(2,4-dichloro-5-methyl-benzenesulfonylamino)cyclopropanecarboxamido]-adamantan-1-carboxylic acid amide | 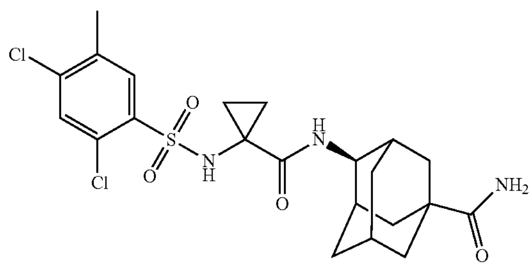 | ¹H NMR (400 MHz, CDCl₃) d 7.96 (s, 1H), 7.54 (s, 1H), 7.34 (d, J = 8.0 Hz, 1H), 6.20 (s, 1H), 5.66 (brs, 1H), 5.54 (brs, 1H), 4.02 (d, J = 7.6 Hz, 1H), 2.43 (s, 3H), 1.92-2.10 (m, 10H), 1.63-1.70 (m, 3H), 1.42-1.45 (m, 2H), 0.75-0.78 (m, 2H) |
| 44 | E-4-[1-(2,4-difluorochloro-benzenesulfonylamino)cyclopropanecarboxamido]-adamantan-1-carboxylic acid amide | 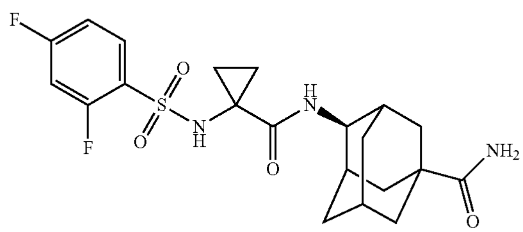 | ¹H NMR (400 MHz, CDCl₃) d 7.91-7.96 (m, 1H), 7.26 (d, J = 6.4 Hz, 1H), 7.03-7.08 (m, 1H), 6.96-7.01 (m, 1H), 5.79 (s, 1H), 5.62 (brs, 1H), 5.48 (brs, 1H), 4.01 (d, J = 8.0 Hz, 1H), 2.10 (s, 2H), 1.92-2.05 (m, 9H), 1.65 (d, J = 13.2 Hz, 2H), 1.45-1.48 (m, 2H), 6.73-0.82 (m, 2H) |
| 45 | E-4-[1-(2-fluoro-4,5-dichloro-benzenesulfonylamino)cyclopropanecarboxamido]-adamantan-1-carboxylic acid amide | 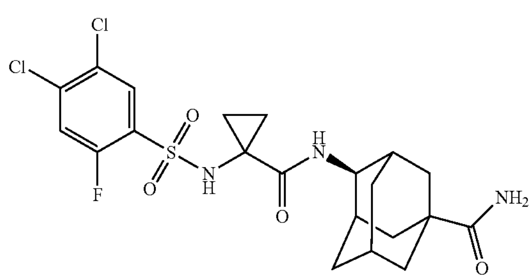 | ¹H NMR (400 MHz, DMSO) d 9.38 (brs, 1H), 8.06 (d, J = 9.6 Hz, 1H), 7.64 (d, J = 7.2 Hz, 1H), 7.09 (d, J = 7.6 Hz, 1H), 7.03 (s, 1H), 6.75 (s, 1H), 3.66 (d, J = 7.2 Hz, 1H), 1.90 (s, 1H), 1.74-1.79 (m, 10H), 1.45 (d, J = 12.4 Hz, 2H), 1.19-1.22 (m, 2H), 0.94-0.97 (m, 2H) |
| 46 | E-4-[1-(2-fluoro-4-chloro-5-methyl-benzenesulfonylamino)cyclopropanecarboxamido]-adamantan-1-carboxylic acid amide | 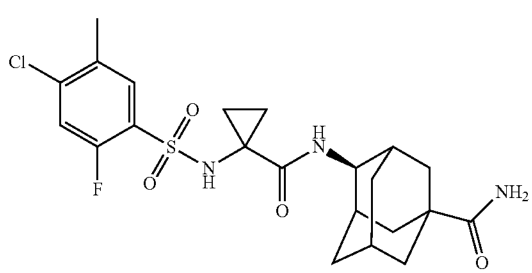 | ¹H NMR (400 MHz, CDCl₃) d 7.76 (d, J = 7.6 Hz, 1H), 7.24-7.30 (m, 2H), 6.32 (s, 1H), 5.69 (brs, 1H), 5.61 (brs, 1H), 4.00 (d, J = 7.6 Hz, 1H), 2.41 (s, 3H), 2.07-2.09 (m, 3H), 1.92-1.00 (m, 8H), 1.63 (d, J = 13.2 Hz, 2H), 1.44-1.47 (m, 2H), 0.82-0.85 (m, 2H) |

TABLE 2-continued

| Example | Compound Name | Structure | NMR data |
|---|---|---|---|
| 47 | E-4-[1-(2,3,4-trifluoro-benzenesulfonylamino)cyclopropanecarboxamido]-adamantan-1-carboxylic acid amide | 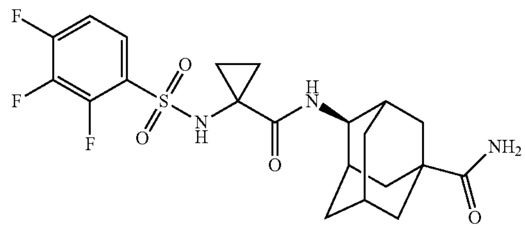 | $^1$H NMR (400 MHz, CDCl$_3$) d 7.67-7.73 (m, 1H), 7.13-7.20 (m, 2H), 6.24 (brs, 1H), 5.64 (brs, 1H), 5.42 (brs, 1H), 4.01 (d, J = 8.0 Hz, 1H), 2.09 (s, 3H), 1.93-2.04 (m, 8H), 1.64 (d, J = 14.0 Hz, 2H), 1.47-1.50 (m, 2H), 0.82-0.86 (m, 2H) |
| 48 | E-4-[1-(thiophen-2-sulfonylamino)cyclopropanecarboxamido]-adamantan-1-carboxylic acid amide | 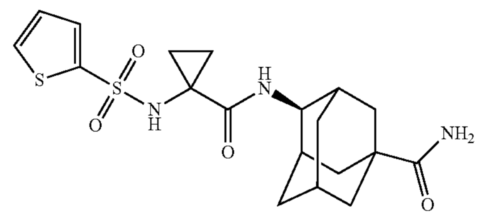 | $^1$H NMR (400 MHz, DMSO) d 9.11 (brs, 1H), 7.97 (dd, J = 4.8, 1.2 Hz, 1H), 7.59 (dd, J = 3.8, 1.4 Hz, 1H), 7.17-7.20 (m, 2H), 7.04 (brs, 1H), 6.75 (brs, 1H), 3.68 (d, J = 7.2 Hz, 1H), 1.74-1.91 (m, 11H), 1.45 (d, J = 11.6 Hz, 2H), 1.14-1.21 (m, 2H), 0.92-0.95 (m, 2H) |
| 49 | E-4-[3-(6-trifluoromethyl-pyridin-2-sulfonylamino)cyclopropanecarboxamido]-adamantan-1-carboxylic acid amide | 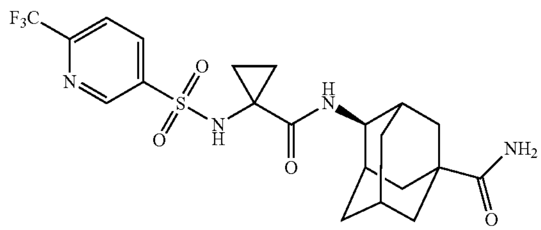 | $^1$H NMR (400 MHz, CDCl$_3$) d 8.36 (d, J = 8.4 Hz, 1H), 7.88 (d, J = 8.0 Hz, 1H), 6.82-6.84 (m, 2H), 5.78 (s, 1H), 5.58 (brs, 1H), 5.25 (brs, 1H), 3.93-3.95 (m, 1H), 2.08 (s, 1H), 1.83-2.04 (m, 12H), 1.48-1.51 (m, 2H), 0.93-0.96 (m, 2H) |
| 50 | E-4-[1-(1-methyl-1H-indole-7-sulfonylamino)cyclopropanecarboxamido]-adamantan-1-carboxylic acid amide | 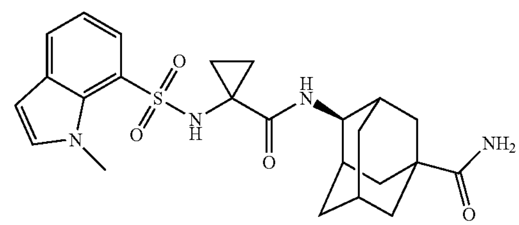 | $^1$H NMR (400 MHz, MeOD) d 7.85 (dd, J = 7.8, 1.0 Hz, 1H), 7.68 (d, J = 4 Hz, 1H), 7.64 (dd, J = 7.7, 0.8 Hz, 1H), 7.27 (d, J = 3.2 Hz, 1H), 713 (t, J = 7.8 Hz, 1H), 6.62 (d, J = 3.2 Hz, 1H), 4.19 (s, 3H), 3.95-3.93 (m, 1H), 2.09-1.92 (m, 22H), 1.65 (d, J = 11.2 Hz, 2H), 1.32-1.29 (m, 2H), 0.94-0.91 (m, 2H) |
| 51 | 1-(3-chloro-benzenesulfonylamino)-N-(4-fluoro-2-(trifluoromethyl)phenyl)cyclopropanecarboxamide | 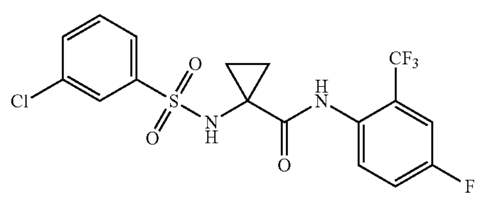 [SMILES: O=C(Nc1ccc(F)cc1C(F)(F)F)C1(NS(=O)(=O)c2cccc(Cl)c2)CC1] | $^1$H NMR (400 MHz, CDCl$_3$) d 8.84 (s, 1H), 7.98-8.01 (m, 1H), 7.84 (s, 1H), 7.75 (d, J = 7.6 Hz, 1H), 7.55 (d, J = 8.0 Hz, 1H), 7.45 (t, J = 8.0 Hz, 1H), 7.32 (dd, J = 8.4, 2.8 Hz, 1H), 7.22-7.26 (m, 1H), 6.57 (s, 1H), 1.50-1.53 (m, 2H), 0.94-0.97 (m, 2H) |
| 52 | E-4-[1-(3-chloro-benzenesulfonylamino)cyclopropanecarboxamido]-N-hydroxyadamantan-1-carboxylic acid amide | 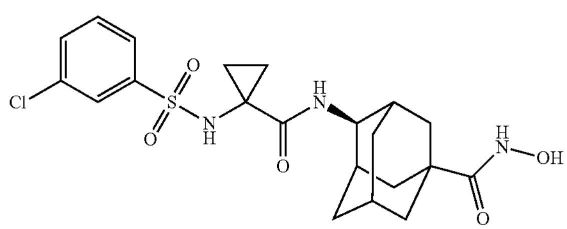 | $^1$H NMR (400 MHz, DMSO) d 10.30 (brs, 1H), 8.58 (brs, 1H), 7.73-7.77 (m, 3H), 7.62-7.66 (m, 1H), 7.15 (d, J = 7.6 Hz, 1H), 3.60 (d, J = 7.2 Hz, 1H), 1.74-1.90 (m, 11H), 1.45 (d, J = 12.0 Hz, 2H), 1.15-1.17 (m, 2H), 0.88-0.91 (m, 2H) |
| 53 | 1-(3-chloro-benzenesufanylamino)-N-[4-(1,1,1-trifluoro-2-hydroxypropan-2-yl)phenyl]cyclopropanecarboxamide | 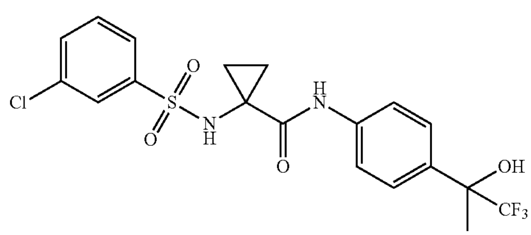 [SMILES: CC(O)(c1ccc(NC(=O)C2(NS(=O)(=O)c3cccc(Cl)c3)CC2)cc1)C(F)(F)F] | $^1$H NMR (400 MHz, DMSO) d 9.44 (s, 1H), 7.77 (s, 1H), 7.72-7.74 (m, 1H), 7.52-7.53 (m, 2H), 7.45-7.47 (m, 2H), 7.39-7.41 (m, 2H), 1.66 (s, 3H), 1.25-1.28 (m, 2H), 0.99-1.02 (m, 2H) |

TABLE 2-continued

| Example | Compound Name | Structure | NMR data |
|---|---|---|---|
| 54 | E-4-[1-(3-chloro-benzeneamino) cyclopropanecarboxamido]-adamantan-1-carboxylic acid amide | 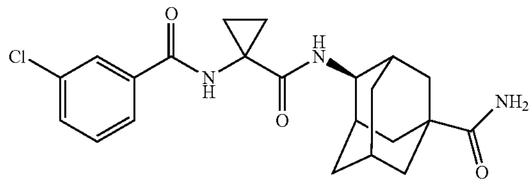 | $^1$H NMR (400 MHz, DMSO) d 9.09 (s, 1H) 7.92 (t, J = 1.6 Hz, 1H), 7.82 (d, J = 8 Hz, 1H), 7.65-7.63 (m, 1H), 7.53 (t, J = 8 Hz, 1H), 7.07 (d, J = 7.2 Hz, 1H), 7.01 (s, 1H), 6.72 (s, 1H), 3.76-3.74 (m, 1H), 1.91-1.65 (m, 11H), 1.40 (d, J = 12.8 Hz, 2H), 1.34-1.31 (m, 2H), 1.04-1.01 (m, 2H) |
| 55 | N-(bicyclo[2.2.1]heptan-2-yl)-1-(3-chloro-benzenesulfonylamino) cyclopropanecarboxamide | 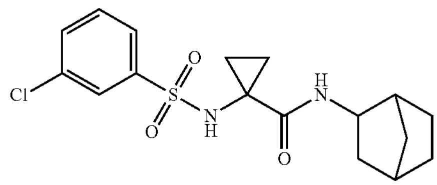 [SMILES: O=C(NC1CC2CCC1C2)C1(NS(=O)(=O)c2cccc(Cl)c2)CC1] | $^1$H NMR (400 MHz, CDCl$_3$) d 7.85 (t, J = 1.8 Hz, 1H), 7.75 (dt, J = 1.2, 7.6 Hz, 1H), 7.56-7.59 (m, 1H), 7.47 (t, J = 8.0 Hz, 1H), 6.90 (d, J = 7.2 Hz, 1H), 6.56 (s, 1H), 3.97-4.03 (m, 1H), 2.37 (s, 1H), 2.22 (s, 1H), 2.00-2.07 (m, 1H), 1.53-1.63 (m, 2H), 1.38-1.47 (m, 4H), 1.31-1.34 (m, 1H), 1.23-1.26 (m, 1H), 0.85-0.94 (m, 2H), 0.73-0.78 (m, 1H) |
| 56 | E-4-[1-(1,1-dioxydobenzo[d]isothiazol-2(3H)-yl)cyclopropanecarboxamido] adamantan-1-carboxylic acid amide | 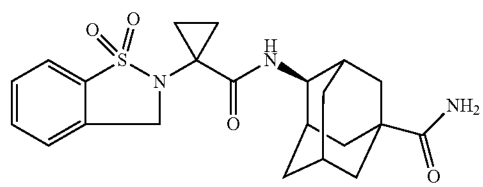 | $^1$H NMR (400 MHz, CDCl$_3$) d 7.83 (d, J = 8.0 Hz, 1H), 7.65-7.72 (m, 2H), 7.59 (t, J = 7.6 Hz, 1H), 7.45 (t, J = 7.6 Hz, 1H), 5.58 (brs, 1H), 5.37 (brs, 1H), 4.53 (s, 2H), 4.02 (d, J = 7.2 Hz, 1H), 1.94-2.03 (m, 10H), 1.84 (s, 2H), 1.66-1.71 (m, 3H), 1.48 (t, J = 12.4 Hz, 2H) |
| 57 | E-4-[1-(3,4-difluoro-benzeneamino) cyclopropanecarboxamido]-adamantan-1-carboxylic acid amide | 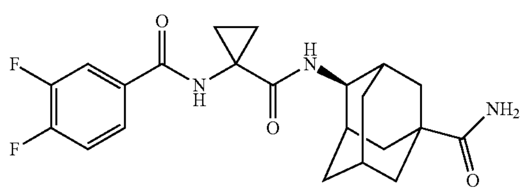 | $^1$H NMR (400 MHz, DMSO) d 9.07 (s, 1H), 7.95 (t, J = 9.6 Hz, 1H), 7.79-7.76 (m, 1H), 7.62-7.55 (m, 1H), 7.06 (d, J = 7.6 Hz, 1H), 6.99 (s, 1H), 6.72 (s, 1H), 3.77-3.75 (m, 1H), 1.89-1.66 (m, 11H), 1.40 (d, J = 12.4 Hz, 2H), 1.34-1.32 (m, 2H), 1.03-1.00 (m, 2H) |
| 58 | E-4-[1-(1-methyl-1H-pyrazole-5-sulfonylamino) cyclopropanecarboxamido]-adamantan-1-carboxylic acid amide | 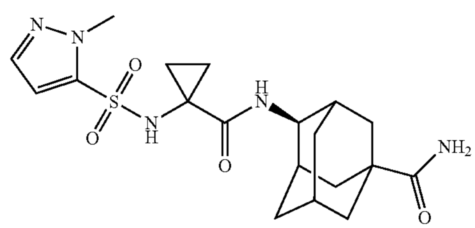 | $^1$H NMR (400 MHz, DMSO) d 7.55 (d, J = 2 Hz, 1H), 7.16 (d, J = 8 Hz, 1H), 7.03 (s, 1H), 6.74 (d, J = 2.4 Hz, 2H), 3.95 (s, 3H), 3.72 (d, J = 7.2 Hz, 1H), 1.93 (s, 1H), 1.83-1.81 (m, 8H), 1.76-1.75 (m, 2H), 1.49 (d, J = 12.4 Hz, 2H), 1.20-1.17 (m, 2H), 0.88-0.85 (m, 2H) |
| 59 | E-4-[1-(2,3-difluoro-benzeneamino) cyclopropanecarboxamido]-adamantan-1-carboxylic acid amide | 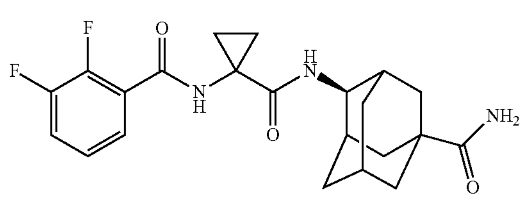 | $^1$H NMR (400 MHz, CDCl$_3$) d 9.15 (s, 1H), 7.64-7.57 (m, 1H), 7.42-7.39 (m, 1H), 7.35-7.30 (m, 1H), 7.03-7.01 (m, 2H), 6.73 (s, 1H), 3.81-3.79 (m, 1H), 1.90-1.74 (m, 11H), 1.47 (d, J = 12.4 Hz, 2H), 1.35-1.33 (m, 2H), 1.04-1.01 (m, 2H) |
| 60 | E-4-[1-(benzenesulfonylamino) cyclopropanecarboxamido]-N-hydroxyadamantan-1-carboxylic acid amide | 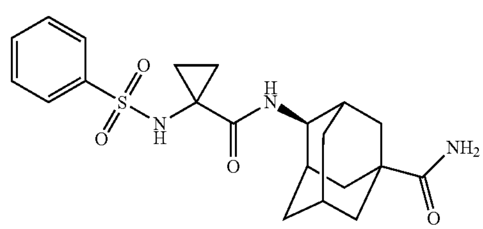 | $^1$H NMR (400 MHz, DMSO) d 8.87 (s, 1H), 7.78 (d, J = 7.6, Hz, 2H), 7.69-7.65 (m, 1H), 7.62-7.59 (m, 2H), 7.21 (d, J = 7.6 Hz, 1H), 7.01 (s, 1H), 6.75 (s, 1H), 3.68-3.66 (m, 1H), 1.92 (s, 1H), 1.82-1.75 (m, 10H), 1.46 (d, J = 12 Hz, 2H), 1.15-1.12 (m, 2H), 0.83-0.80 (m, 2H) |

TABLE 2-continued

| Example | Compound Name | Structure | NMR data |
|---|---|---|---|
| 61 | E-4-[1-(2-fluoro-N-methylbenzenesulfonylamino)cyclopropanecarboxamido]-adamantan-1-carboxylic acid amide | 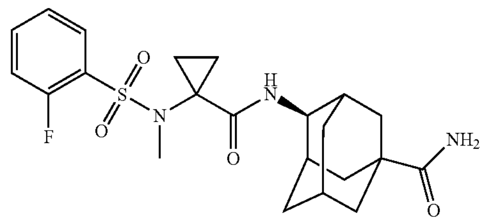 | ¹H.NMR (400 MHz, DMSO) d 7.84 (td, J = 7.6, 1.6 Hz, 1H), 7.82-7.76 (m, 1H), 7.52-7.48 (m, 1H), 7.43 (td, J = 8, 0.8 Hz, 1H), 7.02 (s, 1H), 7.00 (d, J = 7.6 Hz, 1H), 6.75 (s, 1H), 3.82-3.80 (m, 1H), 2.99 (d, J = 1.2 Hz, 3H), 1.93-1.77 (m, 11H), 1.53 (d, J = 12.8 Hz, 2H), 1.39-1.36 (m, 2H), 1.18-1.16 (m, 2H) |
| 62 | E-4-[1-(3-chloro-N-methylbenzenesulfonylamino)cyclopropanecarboxamido]-adamantan-1-carboxylic acid amide | 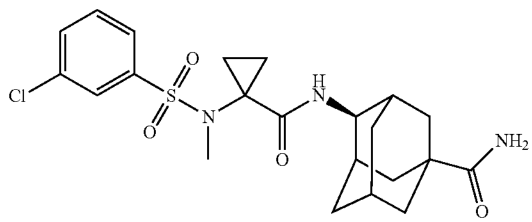 | ¹H NMR (400 MHz, DMSO) d 7.80-7.76 (m, 3H), 7.68-7.64 (m, 1H), 7.02 (s, 1H), 6.96 (d, J = 7.2 Hz, 1H), 6.74 (s, 1H), 3.79-3.77 (m, 1H), 2.95 (s, 3H), 1.93-1.77 (m, 11H), 1.51 (d, J = 12.8 Hz, 2H), 1.41-1.38 (m, 2H), 1.21-1.19 (m, 2H) |
| 63 | E-4-[1-(2-fluorobenzamido)cyclopropanecarboxamido]-adamantan-1-carboxylic acid amide | 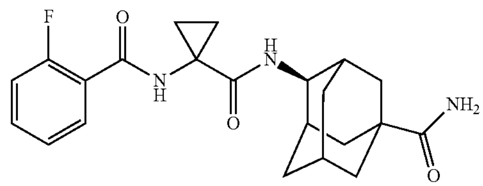 | ¹H NMR (400 MHz, DMSO) d 9.06 (s, 1H), 7.56 (m, 2H), 7.32 (m, 2H), 7.03 (m, 2H), 6.74 (brs, 1H), 3.78 (m, 1H), 1.88-1.74 (m, 10H), 1.45 (d, J = 12.4 Hz, 2H), 1.32 (m, 2H), 1.24 (s, 1H) 1.01 (m, 2H) |
| 64 | E-N-[1-(5-carbamoyladamantan-2-yl)carbamoyl)cyclopropyl)-5-(trifluoromethyl)pyrrolineamide | 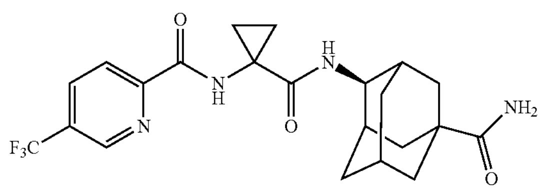 | ¹H NMR (400 MHz, DMSO) d 9.62 (s, 1H), 9.08 (s, 1H), 8.44 (d, J = 7.6 Hz, 1H), 8.21 (d, 8.4 Hz, 1H), 7.07 (d, J = 7.2 Hz, 1H), 6.99 (s, 1H), 6.73 (s, 1H), 3.76 (m, 1H), 1.97-1.64 (m, 11H), 1.34 (m, 4H), 1.02 (m, 2H) |
| 65 | E-4-(1-(benzo[d][1,3]dioxol-5-sulfonylamino)cyclopropanecarboxamino)adamantan-1-carboxylic acid amide | 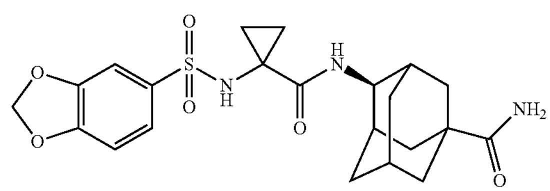 | ¹H NMR (400 MHz, DMSO) d 8.70 (brs, 1H), 7.31 (dd, J = 6.4, 2.0 Hz, 1H), 7.19 (m, 2H), 7.08 (d, J = 8.4 Hz, 1H), 7.01 (brs, 1H), 6.75 (brs, 1H), 6.75 (s, 1H), 3.68 (m, 1H), 1.91-1.75 (m, 11H), 1.45 (d, J = 12.0 Hz, 2H), 1.13 (m, 2H), 0.87 (m, 2H) |
| 66 | 1-(3-chloro-benzenesulfonylamino)-N-cycloheptyl-N-propylcyclopropanecarboxamide | 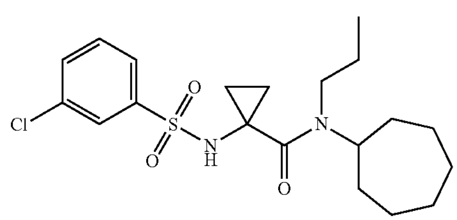 [SMILES: CCCN(C(=O)C1(NS(=O)(=O)c2cccc(Cl)c2)CC1)C1CCCCCC1] | ¹H NMR (400 MHz, CDCl₃) d 7.88 (t, J = 2.0 Hz, 1H), 7.84 (m, 1H), 7.55 (m, 1H), 7.46 (d, J = 7.6 Hz, 1H), 5.07 (brs, 1H), 4.06/2.98 (m, 2H), 1.73-1.23 (m, 21H) |

Preparational Example 19

Preparation of 3-azido-2,2-dimethylpropanoic acid

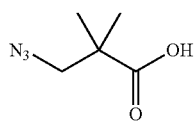

1 g (7.32 mmol) of 3-chloro-2,2-dimethylpropanoic acid was dissolved in 15.0 ml of water, to which 4.8 g (73.22 mmol) of NaN₃ was added, followed by stirring for 18 hours with high temperature reflux. The reaction mixture was acidized with conc. HCl to be pH 3, followed by extraction with 320 ml of ethylacetate. The extract was dried over anhydrous magnesium sulfate, followed by evaporation under reduced pressure to give 1 g of 3-azido-2,2-dimethylpropanoic acid (yield: 95%).

¹H NMR (400 MHz, CDCl₃) δ 3.48 (s, 2H), 1.31 (s, 6H)

Preparational Example 20

Preparation of 3-amino-2,2-dimethylpropanoic acid

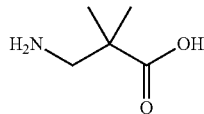

1 g (6.99 mmol) of the 3-azido-2,2-dimethylpropanoic acid prepared in Preparational Example 19 was dissolved in 100 ml of MeOH, to which 695 mg of 10% Pd/C was added, followed by stirring for 3 hours in the presence of hydrogen. 100 ml of water was added to the reaction mixture, followed by stirring for 30 minutes. The mixture was filtered by using celite filter and the resultant solution was evaporated under reduced pressure to give 753 mg of 3-amino-2,2-dimethylpropanoic acid (yield: 92%).

$^1$H NMR (400 MHz, DMSO) δ 2.65 (s, 2H), 1.30 (s, 2H), 1.01 (s, 6H)

Preparational Example 21

Preparation of 3-(t-butoxycarbonylamino)-2,2-dimethylpropanoic acid

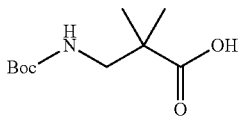

256 mg (2.22 mmol) of the -amino-2,2-dimethylpropanoic acid prepared in Preparational Example 20 was dissolved in 2.0 ml of water and 3.0 ml of t-BuOH, to which 4.0 ml of 1.0 N NaOH solution and 725 mg (3.32 mmol) of Boc$_2$O were added. The mixture was stirred at room temperature for 16 hours, followed by evaporation under reduced pressure to eliminate the solvent. The residue was acidized with 1 N HCl to be pH 3, followed by extraction with 320 ml of ethyl acetate. The extract was dried over anhydrous magnesium sulfate, followed by evaporation under reduced pressure to give 305 mg of 3-(t-butoxycarbonylamino)-2,2-dimethylpropanoic acid (yield: 63%).

$^1$H NMR (400 MHz, CDCl$_3$) δ 3.25 (s, 2H), 1.44 (s, 9H), 1.18 (s, 6H)

Preparational Example 22

Preparation of 4-(3-(t-butoxycarbonyl)amido)-2,2-dimethylpropanamido)adamantan-1-carboxylic acid methyl ester

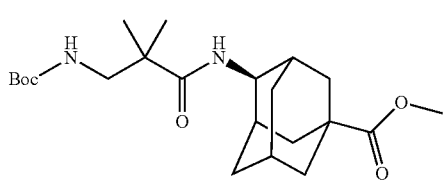

305 mg (1.40 mmol) of the 3-(t-butoxycarbonylamino)-2,2-dimethylpropanoic acid prepared in Preparational Example 21 and 379 mg (1.54 mmol) of the 4-amino-adamantane-1-carboxylic acid methyl ester prepared in Preparational Example 7 were dissolved in 5.0 ml of methylene chloride, to which 323 mg (1.38 mmol) of EDCI and 227 mg (1.68 mmol) of HOBt were added. 0.6 ml (4.21 mmol) of TEA was also added thereto. The reaction mixture was stirred at room temperature for 16 hours, followed by evaporation under reduced pressure to eliminate methylene chloride. The residue was dissolved in 10 ml of water, followed by extraction with 320 ml of ethyl acetate. The extract was dried over anhydrous magnesium sulfate, and evaporated under reduced pressure, followed by column chromatography to give 466 mg of 4-(3-(t-butoxycarbonyl)amido)-2,2-dimethylpropanamido)adamantan-1-carboxylic acid methyl ester (yield: 95%).

$^1$H NMR (400 MHz, CDCl$_3$) δ 6.11 (brs, 1H), 5.12 (brs, 1H), 3.98 (m, 1H), 3.67 (s, 3H), 3.24 (d, J=6.4 Hz, 1H), 2.05-1.74 (m, 10H), 1.63 (s, 3H), 1.43 (s, 9H), 1.21 (s, 6H)

Preparational Example 23

Preparation of 4-(3-amido-2,2-dimethylpropanamido)adamantan-1-carboxylic acid methyl ester hydrochloride

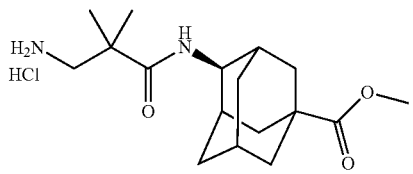

466 mg (1.33 mmol) of the 4-(3-(t-butoxycarbonyl)amido)-2,2-dimethylpropanamido)adamantan-1-carboxylic acid methyl ester prepared in Preparational Example 22 was dissolved in 6 ml of ethyl acetate, to which 3.32 ml of 4 M HCl 1,4-dioxane solution was added, followed by stirring at room temperature for 16 hours. Upon completion of the reaction the reaction solvent was eliminated by evaporation under reduced pressure to give 422 mg of 4-(3-amido-2,2-dimethylpropanamido)adamantan-1-carboxylic acid methyl ester hydrochloride (yield: 92%).

$^1$H NMR (400 MHz, CDCl$_3$) δ 8.73 (brs, 2H), 5.98 (m, 1H), 3.96 (m, 1H), 3.72 (s, 2H), 3.66 (s, 3H), 2.04-1.91 (m, 9H), 1.66 (s, 4H), 1.39 (s, 6H)

Preparational Example 24

Preparation of 4-(3-(3-chlorobenzenesulfonylamino)-2,2-dimethylpropanamido)adamantan-1-carboxylic acid methyl ester

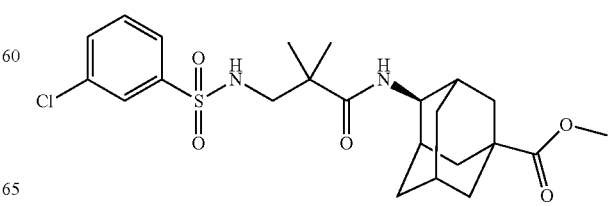

80 mg (0.23 mmol) of the 4-(3-amido-2,2-dimethylpropanamido)adamantan-1-carboxylic acid methyl ester hydrochloride prepared in Preparational Example 23 was dissolved in 1 ml of methylene chloride, to which 0.1 ml of TEA was added, followed by stirring at room temperature for 5 minutes. 59 mg (0.28 mmol) of 3-chlorosulfonylchloride was added to the reactant, followed by stirring at room temperature for 16 hours. The reaction solvent was eliminated by evaporation under reduced pressure. The residue was dissolved in 20 ml of water, followed by extraction with 350 ml of ethyl acetate. The extract was dried over anhydrous magnesium sulfate, and evaporated under reduced pressure, followed by column chromatography to give 101 g of 4-(3-(3-chloro-benzenesulfonylamino)-2,2-dimethylpropanamido)adamantan-1-carboxylic acid methyl ester (yield: 91%).

$^1$H NMR (400 MHz, CDCl$_3$) δ 7.83 (s, 1H), 7.72 (d, J=7.6 Hz, 1H), 7.53 (d, J=8.4 Hz, 1H), 7.45 (t, J=8.0 Hz, 1H), 5.88 (m, 1H), 5.57 (t, J=6.4 Hz, 1H), 3.92 (m, 1H), 3.66 (s, 3H), 2.95 (d, J=6.4 Hz, 2H), 1.99 (s, 8H), 1.85 (s, 2H), 1.65 (m, 3H), 1.26 (s, 6H)

Preparational Example 25

Preparation of 4-(3-(3-chlorobenzenesulfonylamino)-2,2-dimethylpropanamido)adamantan-1-carboxylic acid

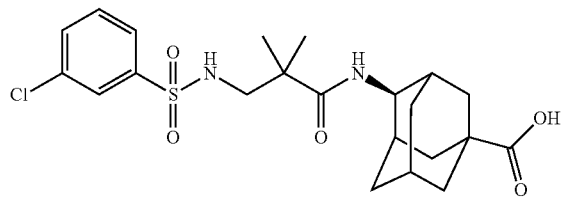

100 mg (0.21 mmol) of the 4-(3-(3-chlorobenzenesulfonylamino)-2,2-dimethylpropanamido)adamantan-1-carboxylic acid methyl ester prepared in Preparational Example 24 was dissolved in 1.0 ml of THF/ethanol mixed solution (1:1), to which 1.0 ml of 2 N NaOH solution was added, followed by stirring at room temperature overnight. The reactant was acidized with 1 N HCl, followed by extraction with ethyl acetate. The extract was dried over anhydrous magnesium sulfate, followed by evaporation under reduced pressure to give 98 mg of 4-(3-(3-chloro-benzenesulfonylamino)-2,2-dimethylpropanamido)adamantan-1-carboxylic acid (yield: 99%).

$^1$H NMR (400 MHz, CDCl$_3$) δ 7.85 (t, J=1.6 Hz, 1H), 7.73 (m, 1H), 7.54 (m, 1H), 7.43 (m, 1H), 6.00 (m, 2H), 3.92 (d, J=6.8 Hz, 1H), 2.95 (d, J=6.0 Hz, 1H), 2.00 (s, 7H), 1.93 (s, 2H), 1.66 (m, 4H), 1.26 (s, 6H)

Example 67

Preparation of E-4-(3-(3-chlorobenzenesulfonylamino)-2,2-dimethylpropanamido)adamantan-1-carboxylic acid amide

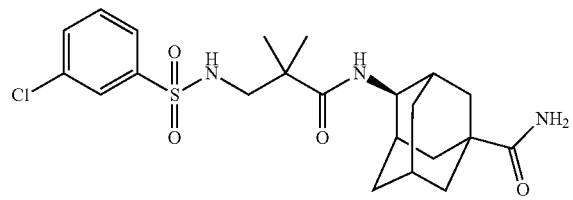

98 mg (0.21 mmol) of the 4-(3-(3-chlorobenzenesulfonylamino)-2,2-dimethylpropanamido)adamantan-1-carboxylic acid prepared in Preparational Example 25 was dissolved in 1.0 ml of methylene chloride, to which 44 mg (0.23 mmol) of HOBt and 31 mg (0.23 mmol) of EDCI were added. The mixture was stirred at room temperature for 10 minutes and then 1.0 ml of 35% ammonia water was added thereto. The mixture was stirred at room temperature for 20 hours. Upon completion of the reaction, extraction was performed with methylene chloride. After washing with brine, the extract was dried over anhydrous magnesium sulfate, followed by column chromatography to give 20.7 mg of 4-(3-(3-chlorobenzenesulfonylamino)-2,2-dimethylpropanamido)adamantan-1-carboxylic acid amide (yield: 21%).

$^1$H NMR (400 MHz, CDCl$_3$) δ 7.84 (s, 1H), 7.73 (d, J=7.6 Hz, 1H), 7.55 (d, J=9.2 Hz, 1H), 7.45 (m, 1H), 5.96 (d, J=7.2 Hz, 1H), 5.80 (m, 1H), 5.68 (s, 1H), 3.95 (s, 1H), 2.95 (d, J=6.4 Hz, 1H), 1.62-2.04 (m, 11H), 1.26 (s, 6H)

The compounds of Example 68-Example 70 were prepared by the preparation method described in Example 67.

TABLE 3

| Example | Compound Name | Structure | NMR data |
|---|---|---|---|
| 68 | E-4-[3-(2-fluoro-benzenesulfonylamino)-2,2-dimethylpropanamido]adamantan-1-carboxylic acid amide | 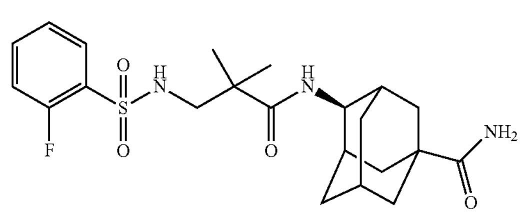 | $^1$H NMR.(400 MHz, DMSO) d 7.79 (m, 1H), 7.68 (m, 2H), 7.41 (m, 2H), 6.99 (s, 1H), 6.82 (s, 1H), 6.72 (s, 1H), 3.71 (m, 1H), 2.98 (s, 1H), 1.91-1.38 (m, 13H), 1.11 (s, 6H) |

TABLE 3-continued

| Example | Compound Name | Structure | NMR data |
|---|---|---|---|
| 69 | E-4-[3-(benzenesulfonylamino)-2,2-dimethylpropanamido]adamantan-1-carboxylic acid amide | 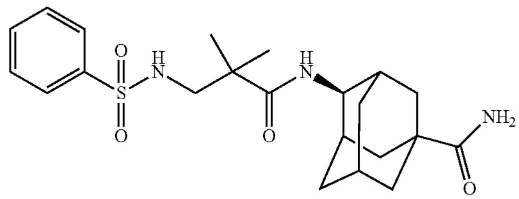 | $^1$H NMR (400 MHz, CDCl$_3$) d 7.84 (m, 2H), 7.57 (m, 3H), 6.16 (brs, 1H), 5.98 (d, J = 7.6 Hz, 1H), 5.69 (brs, 1H), 5.59 (m, 1H), 3.93 (d, J = 4.8 Hz, 1H), 2.94 (d, J = 6.8 Hz, 1H), 2.04-1.80 (m, 9H), 1.73-1.61 (m, 4H), 1.24 (s, 6H) |
| 70 | E-4-[3-(3-chloro-2-methyl-benzenesulfonylamino)-2,2-dimethylpropanamido]adamantan-1-carboxylic acid amide | 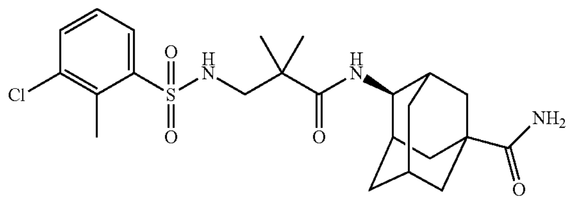 | $^1$H NMR (400 MHz, CDCl$_3$) d 7.84 (dd, J = 6.8, 0.8 Hz, 1H), 7.56 (d, J = 4.8 Hz, 1H), 7.25 (m, 1H), 5.86 (m, 4H), 3.95 (d, J = 7.6 Hz, 1H), 2.91 (d, J = 6.4 Hz, 2H), 2.75 (s, 3H),1.59-2.05 (m, 11H), 1.23 (s, 6H) |

Preparational Example 26

Preparation of 2-(t-butoxycarbonylamino)-2-methylpropanoic acid

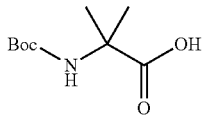

200 mg (1.94 mmol) of 2-amino-2-methylpropanoic acid was dissolved in 8.0 ml of 1.0 N NaOH solution and 8.0 ml of 1,4-dioxane solution, to which 846 mg (3.88 mmol) of Boc$_2$O was added. The mixture was stirred at room temperature for 16 hours, and then 1,4-dioxane was eliminated by evaporation under reduced pressure. The residue was acidized with 1 N HCl to be pH 3, and followed by extraction with 320 ml of ethyl acetate. The extract was dried over anhydrous magnesium sulfate, followed by evaporation under reduced pressure to give 315 mg of 2-(t-butoxycarbonylamino)-2-methylpropanoic acid (yield: 80%).

$^1$H NMR (400 MHz, CDCl$_3$) δ 5.07 (brs, 1H), 1.54 (s, 6H), 1.45 (s, 9H)

Preparational Example 27

Preparation of 4-(2-((t-butoxycarbonyl)amino)-2-methylpropanamido)adamantan-1-carboxylic acid methyl ester

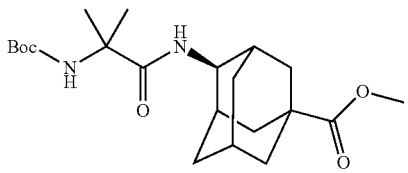

380 mg (1.87 mmol) of the 2-(t-butoxycarbonylamino)-2-methylpropanoic acid prepared in Preparational Example 26 and 505 mg (2.06 mmol) of the 4-amino-adamantan-1-carboxylic acid methyl ester prepared in Preparational Example 7 were dissolved in 10.0 ml of methylene chloride, to which 430 mg (2.24 mmol) of EDCI and 303 mg (2.24 mmol) of HOBt were added. 0.8 ml (5.61 mmol) of TEA was also added thereto. The reaction mixture was stirred at room temperature for 16 hours, followed by evaporation under reduced pressure to eliminate methylene chloride. The residue was dissolved in 10 ml of water, followed by extraction with 320 ml of ethyl acetate. The extract was dried over anhydrous magnesium sulfate, and evaporated under reduced pressure, followed by column chromatography to give 580 mg of 4-(2-((t-butoxycarbonyl)amino)-2-methylpropanamido)adamantan-1-carboxylic acid methyl ester (yield: 92%).

$^1$H NMR (400 MHz, CDCl$_3$) δ 5.30 (s, 1H), 4.84 (brs, 1H), 3.98 (brs, 1H), 3.66 (s, 3H), 2.02-1.44 (m, 28H)

Preparational Example 28

Preparation of 4-(2-amino-2-methylpropanamido)adamantan-1-carboxylic acid methyl ester hydrochloride

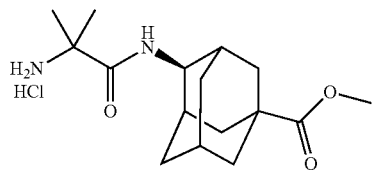

580 mg (1.72 mmol) of the 4-(2-((t-butoxycarbonyl)amino)-2-methylpropanamido)adamantan-1-carboxylic acid methyl ester prepared in Preparational Example 27 was dissolved in 6 ml of ethyl acetate, to which 4.31 ml of 4 M HCl 1,4-dioxane was added. The mixture was stirred at room temperature for 16 hours. Upon completion of the reaction, the reaction solvent was eliminated by evaporation under reduced pressure to give 495 mg of 4-(2-amino-2-methylpropanamido)adamantan-1-carboxylic acid methyl ester hydrochloride (yield: 87%).

$^1$H NMR (400 MHz, CDCl$_3$) δ 8.80 (brs, 2H), 6.48 (brs, 1H), 4.01 (brs, 1H), 3.66 (s, 3H), 2.09-1.60 (m, 19H)

Preparational Example 29

Preparation of 4-[2-(2-fluoro-benzenesulfonylamino)-2-methylpropanamido]-adamantan-1-carboxylic acid methyl ester

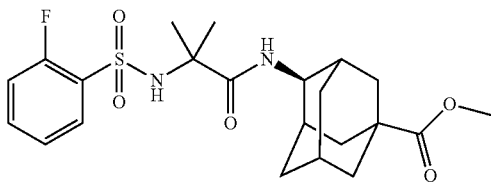

100 mg (0.3 mmol) of the 4-(2-amino-2-methylpropanamido)adamantan-1-carboxylic acid methyl ester hydrochloride prepared in Preparational Example 28 was dissolved in 1 ml of methylene chloride, to which 0.13 ml of TEA was added, followed by stirring at room temperature for 5 minutes. 70 mg (0.36 mmol) of 3-chlorosulfonylchloride was added to the reactant, followed by stirring at room temperature for 16 hours. The reaction solvent was eliminated by evaporation under reduced pressure. The residue was dissolved in 20 ml of water, followed by extraction with 350 ml of ethyl acetate. The extract was dried over anhydrous magnesium sulfate, and evaporated under reduced pressure, followed by column chromatography to give 107 g of 4-[2-(2-fluoro-benzenesulfonylamino)-2-methylpropanamido]-adamantan-1-carboxylic acid methyl ester (yield: 78%).

$^1$H NMR (400 MHz, CDCl$_3$) δ 7.89 (td, J$_1$=1.6 Hz, J$_2$=6.0 Hz, 1H), 7.60 (m, 1H), 7.28 (m, 2H), 7.00 (d, J=9.2 Hz, 1H), 3.97 (m, 1H), 3.66 (s, 3H), 2.03 (m, 7H), 1.88 (m, 4H), 1.62 (d, J=13.2 Hz, 2H), 1.39 (s, 6H)

Preparational Example 30

Preparation of 4-[2-(2-fluoro-benzenesulfonylamino)-2-methylpropanamido]-adamantan-1-carboxylic acid

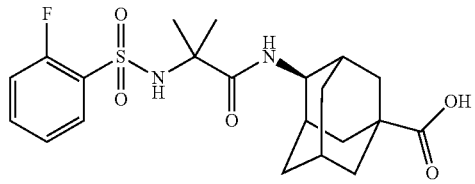

105 mg (0.23 mmol) of the 4-[2-(2-fluoro-benzenesulfonylamino)-2-methylpropanamido]-adamantan-1-carboxylic acid methyl ester prepared in Preparational Example 29 was dissolved in 1.0 ml of THF/ethanol mixed solution (1:1), to which 1.0 ml of 2 N NaOH solution was added, followed by stirring at room temperature overnight. The reactant was acidized with 1 N HCl, followed by extraction with ethyl acetate. The extract was dried over anhydrous magnesium sulfate, followed by evaporation under reduced pressure to give 100 mg of 4-[2-(2-fluoro-benzenesulfonylamino)-2-methylpropanamido]-adamantan-1-carboxylic acid (yield: 99%).

$^1$H NMR (400 MHz, CDCl$_3$) δ 7.89 (td, J$_1$=2.0 Hz, J$_2$=6.0 Hz, 1H), 7.60 (m, 1H), 7.28 (m, 2H), 7.03 (d, J=8.0 Hz, 1H), 3.98 (d, J=8.0 Hz, 1H), 2.05 (m, 7H), 1.95 (s, 2H), 1.88 (d, J=12.8 Hz, 2H), 1.45 (d, J=12.0 Hz, 2H), 1.39 (s, 6H)

Example 71

Preparation of E-4-[2-(2-fluoro-benzenesulfonylamino)-2-methylpropanamido]-adamantan-1-carboxylic acid amide

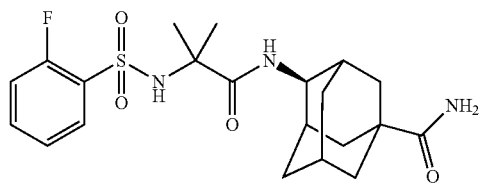

100 mg (0.23 mmol) of the 4-[2-(2-fluoro-benzenesulfonylamino)-2-methylpropanamido]-adamantan-1-carboxylic acid prepared in Preparational Example 30 was dissolved in 7.0 ml of methylene chloride, to which 34 mg (0.25 mmol) of HOBt and 48 mg (0.25 mmol) of EDCI were added. The mixture was stirred at room temperature for 10 minutes and then 7.0 ml of 35% ammonia water was added thereto. The mixture was stirred at room temperature for 20 hours. Upon completion of the reaction, extraction was performed with methylene chloride. After washing with brine, the extract was dried over anhydrous magnesium sulfate, followed by column chromatography to give 15 mg of 4-[2-(2-fluoro-benzenesulfonylamino)-2-methylpropanamido]-adamantan-1-carboxylic acid amide (yield: 15%).

$^1$H NMR (400 MHz, CDCl$_3$) δ 7.89 (td, J$_1$=1.6 Hz, J$_2$=6.0 Hz, 1H), 7.61 (m, 1H), 7.36 (d, J=4.8 Hz, 1H), 7.30 (m, 1H), 7.24 (m, 1H), 7.03 (d, J=7.6 Hz, 1H), 5.57 (brs, 1H), 3.97 (d, J=7.6 Hz, 1H), 2.09 (s, 3H), 2.00 (m, 4H), 1.89 (m, 4H), 1.63 (d, J=12.4 Hz, 2H), 1.39 (s, 6H)

The compounds of Example 72-Example 90 were prepared by the preparation method described in Example 71.

TABLE 4

| Example | Compound Name | Structure | NMR data |
|---|---|---|---|
| 72 | E-4-[2-(2-fluoro-N-methyl-benzenesulfonylamino)-2-methylpropanamido]adamantan-1-carboxylic acid amide | 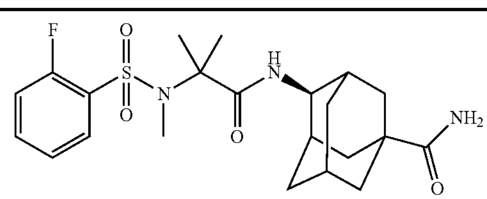 | $^1$H NMR (400 MHz, CDCl$_3$) d 7.93 (m, 1H), 7.61 (m, 1H), 7.31 (td, J$_1$ = 0.8 Hz, J$_2$ = 7.6 Hz, 1H), 7.27 (m, 2H), 7.06 (d, J = 8.0 Hz, 1H), 5.62 (brs, 2H), 4.00 (d, J = 8.4 Hz, 1H), 3.05 (d, J = 1.6 Hz, 3H), 2.18-1.50 (m, 13H), 1.46 (s, 6H) |

TABLE 4-continued

| Example | Compound Name | Structure | NMR data |
|---|---|---|---|
| 73 | E-4-[2-(3-chloro-benzenesulfonylamino)-2-methylpropanamido]adamantan-1-carboxylic acid amide | 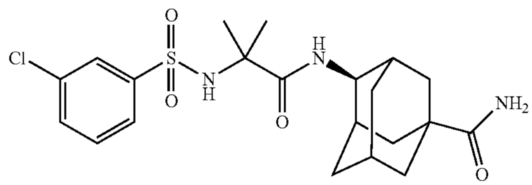 | $^1$H NMR (400 MHz, (CDCl$_3$) d 7.87 (t, J = 1.6 Hz, 1H), 7.76 (m, 1H), 7.55 (m, 1H), 6.74 (d, J = 7.2 Hz, 1H), 5.56 (brs, 1H), 5.19 (brs, 1H), 3.95 (d, J = 7.2 Hz, 1H), 2.07 (s, 3H), 2.00 (s, 4H), 1.92 (s, 2H), 1.82 (d, J = 15.2 Hz, 2H), 1.63 (d, J = 14.0 Hz, 2H), 1.44 (s, 6H) |
| 74 | E-N-(5-cyanoadamantan-2-yl)-2-(2-fluoro-benzenesulfonylamino)-2-methylpropanamide | 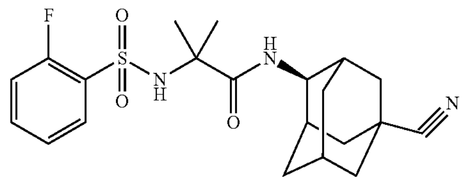 | $^1$H NMR (400 MHz, CDCl$_3$) d 7.88 (td, J$_1$ = 1.6 Hz, J$_2$ = 4.0 Hz, 1H), 7.62 (m, 1H), 7.32 (m, 2H), 7.10 (d, J = 7.6 Hz, 1H), 5.28 (s, 1H), 3.99 (d, J = 7.6 Hz, 1H), 2.16 (s, 4H), 2.09 (m, 5H), 1.91 (d, J = 13.6 Hz, 2H), 1.64 (d, J = 13.6 Hz, 2H), 1.34 (s, 6H) |
| 75 | E-2-(2-fluoro-benzenesulfonylamino)-N-[5-(N'-carbamimidoyl)adamantan-2-yl]-2-methylpropanamide | 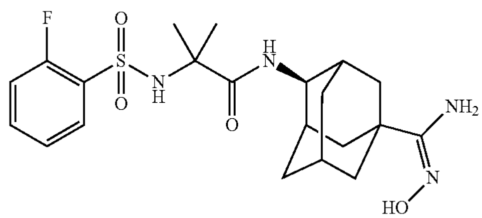 | $^1$H NMR (400 MHz, CDCl$_3$) d 7.89 (td, J$_1$ = 1.6 Hz, J$_2$ = 6.0 Hz, 1H), 7.61 (m, 1H), 7.30 (td, J$_1$ = 0.8 Hz, J$_2$ = 6.8 Hz, 1H), 7.25 (m, 1H), 7.03 (d, J = 8.0 Hz, 1H), 5.39 (s, 1H), 4.55 (s, 2H), 3.97 (m, 1H), 2.10-1.84 (m, 11H), 1.61 (d, J = 13.2 Hz, 2H), 1.39 (s, 6H) |
| 76 | E-2-(2-fluoro-benzenesulfonylamino)-N-[5-(hydroxymethyl)adamantan-2-yl]-2-methylpropanamide | 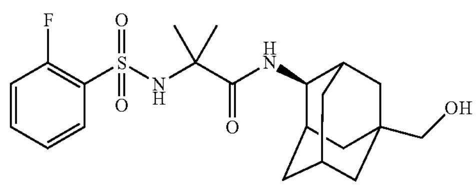 | $^1$H NMR (400 MHz, CDCl$_3$) d 7.89 (t, J = 7.2 Hz, 1H), 7.61 (m, 1H), 7.26 (m, 2H), 7.05 (d, J = 8.0 Hz, 1H), 5.74 (s, 1H), 3.92 (m, 1H), 3.24 (s, 2H), 2.02 (s, 3H), 1.86 (d, J = 13.2 Hz, 2H), 1.61 (m, 8H), 1.39 (s, 6H) |
| 77 | E-2-(2-fluoro-benzenesulfonylamino)-N-(5-formyladamantan-2-yl)-2-methylpropanamide | 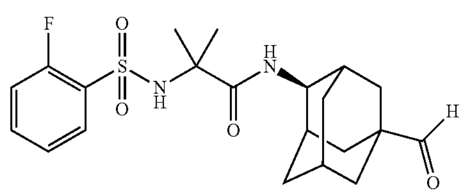 | $^1$H NMR (400 MHz, CDCl$_3$) d 9.37 (s, 1H), 7.90 (td, J$_1$ = 2.0 Hz, J$_2$ = 5.6 Hz, 1H), 7.61 (m, 1H), 7.30 (m, 2H), 7.11 (d, J = 7.6 Hz, 1H), 5.55 (s, 1H), 3.97 (m, 1H), 2.13-1.61 (m, 13H), 1.39 (s, 6H) |
| 78 | E-[4-(2-(2-fluoro-benzenesulfonylamino)-2-methylpropanamido)adamantan-1-yl]methyl-4-methylbenzenesulfonate | 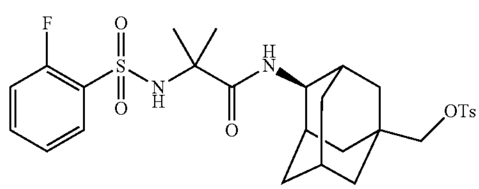 | $^1$H NMR (400 MHz, CDCl$_3$) d 7.88 (td, J$_1$ = 1.6 Hz, J$_2$ = 6.0 Hz, 1H), 7.77 (d, J = 8.4 Hz, 2H), 7.59 (m, 1H), 7.33 (d, J = 8.0 Hz, 2H), 7.30 (m, 2H), 6.97 (d, J = 8.0 Hz, 1H), 5.34 (s, 1H), 3.86 (d, J = 7.6 Hz, 1H), 3.60 (s, 2H), 2.46 (s, 3H), 1.99 (s, 3H), 1.89 (d, 12.0 Hz, 2H), 1.55 (m, 8H), 1.37 (s, 6H) |
| 79 | E-2-[4-(2-(2-fluorobenzenesulfonylamino)-2-methylpropanamido)adamantan-1-yl]acetic acid | 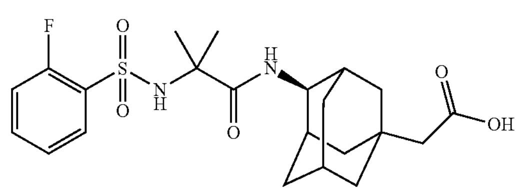 | $^1$H NMR (400 MHz, MeOD) d 7.75 (m, 1H), 7.65 (d, J = 4.4 Hz, 1H), 7.46 (m, 1H), 7.00 (m, 2H), 3.86 (d, J = 4.8 Hz, 1H), 2.11-1.16 (m, 13H), 1.34 (s, 6H) |

TABLE 4-continued

| Example | Compound Name | Structure | NMR data |
|---|---|---|---|
| 80 | E-N-[5-(2-amino-2-oxoethyl)adamantan-2-yl]-2-(2-fluorobenzenesulfonylamino)-2-methylpropanamide | 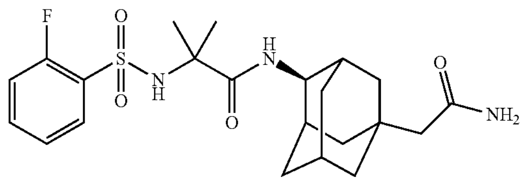 | $^1$H NMR (400 MHz, DMSO) d 8.43 (s, 1H), 7.81 (m, 1H), 7.71 (m, 1H), 7.41 (m, 2H), 7.18 (m, 2H), 6.69 (s, 1H), 3.61 (d, J = 7.6 Hz, 1H), 3.32 (s, 2H), 1.89-1.34 (m, 13H), 1.24 (s, 6H) |
| 81 | E-4-[2-methyl-2-(benzenesulfonylamino)propanamido]adamantan-1-carboxylic acid amide | 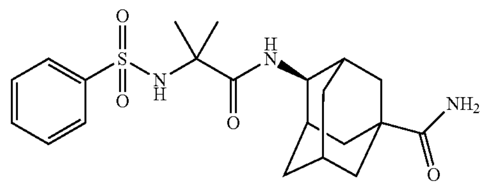 | $^1$H NMR (400 MHz, CDCl$_3$) d 7.89 (m, 2H), 7.56 (m, 1H), 7.51 (m, 2H), 7.01 (d, J = 7.6 Hz, 1H), 5.71 (s, 1H), 5.64 (brs, 1H), 5.54 (brs, 1H), 3.96 (m, 1H), 2.08 (s, 3H), 1.99 (s, 4H), 1.90 (m, 4H), 1.61 (d, J = 14.4 Hz, 2H), 1.40 (s, 6H) |
| 82 | E-4-[2-(2-fluoro-3-chloro-benzenesulfonylamino)-2-methylpropanamido]adamantan-1-carboxylic acid amide | 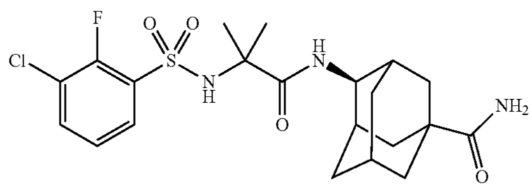 | $^1$H NMR (400 MHz, CDCl$_3$) d 7.80-7.77 (m, 1H), 7.67-7.63 (m, 1H), 7.25-7.23 (m, 1H), 6.94 (d, J = 8.0 Hz, 1H), 5.72 (s, 1H), 5.62 (s, 1H), 5.46 (s, 1H), 3.99-3.93 (m, 1H), 2.09-1.87 (m, 11H), 1.66 (d, J = 13.2 Hz, 3H), 1.42 (s, 6H) |
| 83 | E-4-[2-(3,5-difluoro-benzenesulfonylamino)-2-methylpropanamido]adamantan-1-carboxylic acid amide | 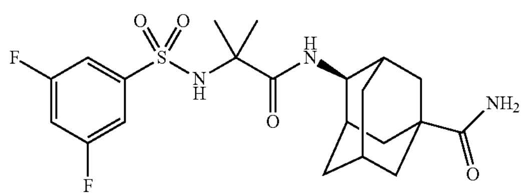 | $^1$H NMR (400 MHz, CDCl$_3$) d 7.45-7.40 (m, 2H), 7.45-7.40 (m, 2H), 7.06-7.00 (m, 1H), 6.65 (d, J = 8.0 Hz, 1H), 5.66 (s, 1H), 5.59 (s, 1H), 5.32 (s, 1H), 3.98 (J = 8.0 Hz, 1H), 2.08 (s, 3H), 2.00 (s, 4H), 1.92 (d, J = 2.0 Hz, 2H), 1.84 (d, J = 13.2 Hz, 2H), 1.66 (d, J = 13.2 Hz, 2H), 1.47 (s, 6H) |
| 84 | E-4-[2-(2,6-difluoro-benzenesulfonylamino)-2-methylpropanamido]adamantan-1-carboxylic acid amide | 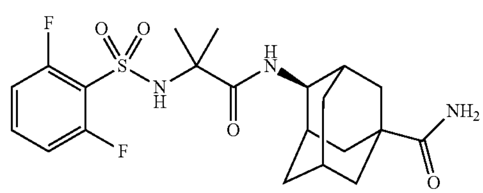 | $^1$H NMR (400 MHz, CDCl$_3$) d 7.58-7.51 (m, 1H), 7.06 (t, 2H), 6.95 (d, J = 8.0 Hz, 1H), 5.88 (s, 1H), 5.62 (s, 1H), 5.42 (s, 1H), 3.98 (d, J = 8.0 Hz, 1H), 2.09 (s, 3H), 1.09-1.86 (m, 8H), 1.65 (d, J = 11.6 Hz, 3H), 1.53 (s, 3H) |
| 85 | E-2-(2-fluoro-benzenesulfonylamino)-N-(5-(hydrazinecarbonyl)adamantan-2-yl)-2-methylpropanamide | 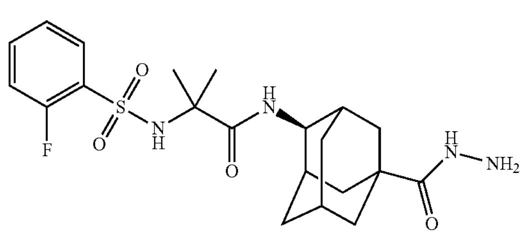 | $^1$H NMR (400 MHz, DMSO) d 8.77 (s, 1H), 7.54 (dd, J = 6.4, 1.4 Hz, 1H), 7.44-7.36 (m, 2H), 7.16 (d, J = 7.6 Hz, 1H), 6.93 (s, 1H), 6.69 (t, J = 7.4 Hz, 1H), 4.34 (s, 2H), 4.15 (s, 1H), 3.68-3.66 (m, 1H), 1.93-1.77 (m, 11H), 1.49 (d, J = 12 Hz, 2H), 1.21 (s, 6H) |
| 86 | E-N-(5-(3-amino-3-oxopropyl)adamantan-2-yl)-2-(2-fluoro-benzenesulfonylamino)-2-methylpropanamide | 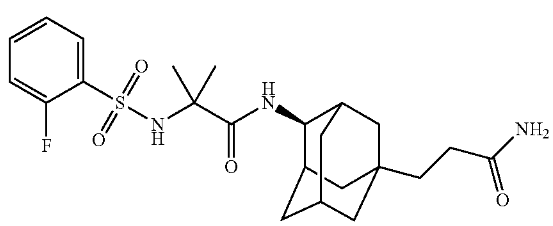 | $^1$H NMR (400 MHz, CDCl$_3$) d 7.84-7.91 (m, 1H), 7.57-7.62 (m, 1H), 7.25-7.31 (m, 1H), 7.21-7.33 (m, 1H), 7.01 (d, J = 7.6 Hz, 1H), 5.92 (s, 1H), 5.63 (brs, 1H), 5.61 (brs, 1H), 3.90 (t, J = 4.0 Hz, 1H), 2.17-2.21 (m, 2H), 1.99 (s, 3H), 1.85 (d, J = 13.2 Hz, 2H), 1.46-1.58 (m, 10H), 1.39 (s, 6H) |

TABLE 4-continued

| Example | Compound Name | Structure | NMR data |
|---|---|---|---|
| 87 | E-2-(2-fluoro-benzenesulfonylamino)-N-(5-(hydrazinecarbonyl)adamantan-2-yl)-2-methylpropanamide | 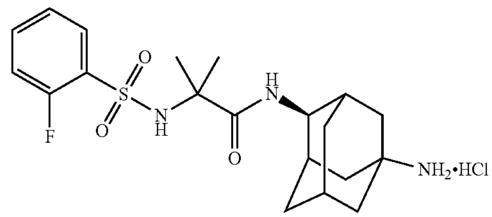 | $^1$H NMR (400 MHz, DMSO) d 8.42 (s, 1H), 8.12 (s, 1H), 7.79-7.83 (m, 1H), 7.69-7.74 (m, 1H), 7.43-7.48 (m, 1H), 7.36-7.43 (m, 1H), 7.20 (d, J = 7.2 Hz, 1H), 3.64 (d, J = 6.8 Hz, 1H), 1.82-2.09 (m, 11H), 1.44 (d, J = 12.8 Hz, 2H), 1.24 (s, 6H) |
| 88 | E-4-[2-(4-chloro-benzenesulfonylamino)-2-methylpropanamido]adamantan-1-carboxylic acid amide | 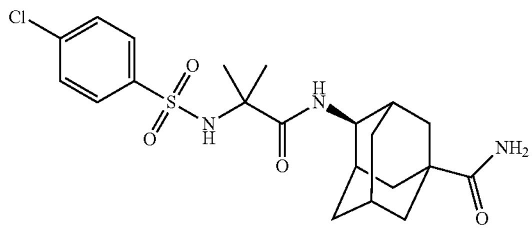 | $^1$H NMR (400 MHz, DMSO) d 8.26 (s, 1H), 7.82-7.79 (m, 2H), 767-7.65 (m, 2H), 7.07 (d, J = 7.6 Hz, 1H), 7.02 (s, 1H), 6.75 (s, 1H), 3.57-3.55 (m, 1H), 1.90-1.75 (m, 11H), 1.46 (d, J = 12 Hz, 2H), 1.25 (s, 6H) |
| 89 | E-4-[2-(2,5-dichloro-benzenesulfonylamino)-2-methylpropanamido]adamantan-1-carboxylic acid amide | 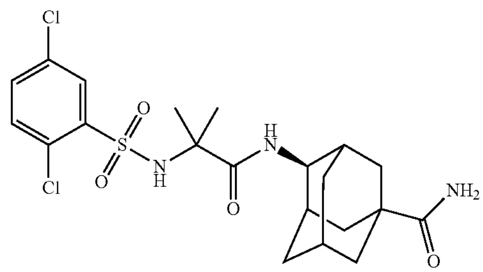 | $^1$H NMR (400 MHz, DMSO) d 8.50 (s, 1H), 7.95 (d, J = 2 Hz, 1H), 7.77-7.72 (m, 2H), 7.18-7.14 (m, 1H), 7.01 (s, 1H), 6.34 (s, 1H), 3.75-3.73 (m, 1H), 1.93-1.77 (m, 11H), 1.49 (d, J = 9.6 Hz, 2H), 1.25 (s, 6H) |
| 90 | 2-(3-chloro-benzenesulfonylamino)-N-cycloheptyl-2-methyl-N-propylpropanamide | 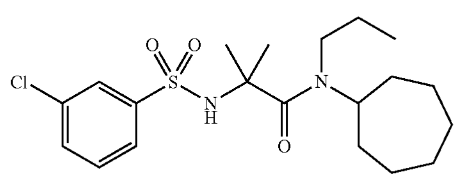 [SMILES: CCCN(C(=O)C(C)(C)NS(=O)(=O)c1cccc(Cl)c1)C1CCCCCC1] | $^1$H NMR (400 MHz, CDCl$_3$) d 7.89 (s, 1H), 7.81 (d, J = 8.0 Hz, 1H), 7.50-7.48 (m, 1H), 7.43 (t, 1H), 6.73 (s, 1H), 3.05-3.00 (m, 1H), 2.79 (t, 2H), 2.08-2.01 (m, 2H), 1.78-1.60 (m, 6H), 1.59-1.42 (m, 5H), 0.94 (t, 3H) |

Preparational Example 31

Preparation of 4-(3-nitrobenzamido)-adamantan-1-carboxylic acid methyl ester

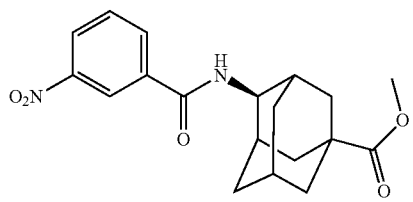

33 mg (0.2 mmol) of 3-nitrobenzoic acid and 50 mg (0.2 mmol) of 4-amino-adamantane-1-carboxylic acid methyl ester were dissolved in 5.0 ml of methylene chloride, to which 60 mg (0.3 mmol) of EDC and 40 mg (0.3 mmol) of HOBt were added. 0.3 ml of TEA was also added thereto. The reaction mixture was stirred at room temperature for 12 hours, followed by evaporation under reduced pressure to eliminate methylene chloride. The residue was dissolved in 10 ml of water, followed by extraction with 320 ml of ethyl acetate. The extract was dried over anhydrous magnesium sulfate, and evaporated under reduced pressure, followed by column chromatography to give 70 mg of 4-(3-nitro-benzamido)-adamantan-1-carboxylic acid methyl ester (yield: 97%).

$^1$H NMR (400 MHz, CDCl$_3$) δ 8.56 (s, 1H), 8.37-8.35 (m, 1H), 8.16-8.14 (m, 1H) 7.66 (t, J=8.0 Hz, 1H), 6.46 (d, J=4.0 Hz, 1H), 4.27-4.26 (m, 1H), 3.96 (s, 3H), 2.21 (s, 2H), 2.12-2.03 (m, 5H), 1.96 (s, 2H), 1.89-1.85 (m, 2H), 1.68-1.66 (m, 2H).

Preparational Example 32

Preparation of 4-(3-amino-benzamido)-adamantan-1-carboxylic acid methyl ester

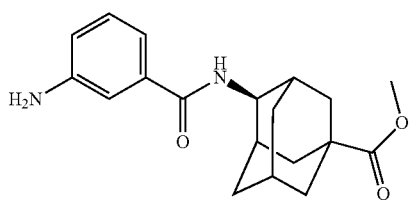

30 mg (0.08 mmol) of the 4-(3-nitro-benzamido)-adamantan-1-carboxylic acid methyl ester prepared in Preparational Example 31 was dissolved in 10 ml of methanol, to which 3 mg of Pd/C was added. The mixture was stirred at room temperature for 12 hours in the presence of hydrogen, which was then filtered. Methanol was eliminated by evaporation under reduced pressure. The obtained compound proceeded to the next reaction without purification.

$^1$H NMR (400 MHz, CDCl$_3$) δ 7.40 (t, J=4.0 Hz, 1H), 7.15 (s, 1H), 7.09-7.07 (m, 2H), 6.84-6.81 (m, 1H), 6.36-6.35 (m, 1H), 4.24 (s, 1H), 3.70 (s, 1H), 2.18-1.85 (m, 9H), 1.88-1.85 (m, 2H) 1.69-1.61 (m, 2H).

Preparational Example 33

Preparation of 4-[3-(2-fluoro-benzenesulfonylamino)-benzamido]-adamantan-1-carboxylic acid methyl ester

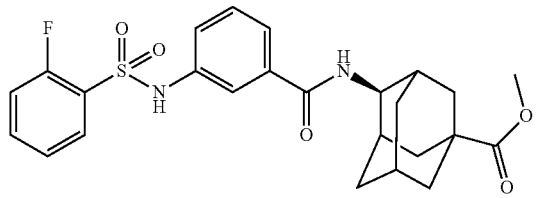

30 mg (0.09 mmol) of the 4-(3-amino-benzamido)-adamantan-1-carboxylic acid methyl ester prepared in Preparational Example 32 was dissolved in 5.0 ml of methylene chloride, to which 14 mg (0.18 mmol) of pyridine was added. 20 mg (0.11 mmol) of 2-fluoro-benzenesulfonylchloride was also added thereto. The mixture was stirred at room temperature for 12 hours, followed by evaporation under reduced pressure to eliminate methylene chloride. The residue was dissolved in 10 ml of water, followed by extraction with 320 ml of ethyl acetate. The extract was dried over anhydrous magnesium sulfate, and evaporated under reduced pressure, followed by column chromatography to give 30 mg of 4-[3-(2-fluoro-benzenesulfonylamino)-benzamido]-adamantan-1-carboxylic acid methyl ester (yield: 70%).

$^1$H NMR (400 MHz, CDCl$_3$) δ 7.85 (s, 1H), 7.60-7.46 (m, 3H), 7.22-7.09 (m, 2H) 7.01 (s, 1H), 6.33-6.28 (m, 2H), 4.19 (s, 1H), 3.68 (s, 3H), 2.14-1.93 (m 9H), 1.78-1.65 (m, 4H).

Preparational Example 34

Preparation of 4-[3-(2-fluoro-benzenesulfonylamino)-benzamido]-adamantan-1-carboxylic acid

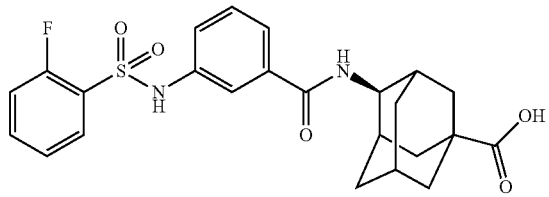

30 mg (0.06 mmol) of the 4-[3-(2-fluoro-benzenesulfonylamino)-benzamido]-adamantan-1-carboxylic acid methyl ester prepared in Preparational Example 33 was dissolved in 1.0 ml of methanol and 1.0 ml of water, to which 24 mg (0.6 mmol) of sodium hydroxide was added. The mixture was stirred at room temperature for 12 hours, followed by evaporation under reduced pressure to eliminate methanol. The residue was acidized with 1 N HCl, followed by extraction with 320 ml of chloroform. The extract was dried over anhydrous magnesium sulfate, followed by evaporation under reduced pressure. The obtained compound proceeded to the next reaction without purification.

$^1$H NMR (400 MHz, CDCl$_3$) δ 7.85-7.80 (m, 1H), 7.60 (s, 1H), 7.50-7.45 (m, 1H) 7.35-7.21 (m, 4H), 7.11 (s, 1H), 6.30 (d, J=4.0 Hz, 1H), 4.20 (s, 1H), 2.20-2.00 (m 9H), 1.89-1.82 (m, 2H), 1.72-1.69 (m, 2H).

Example 91

Preparation of E-4-[3-(2-fluoro-benzenesulfonylamino)-benzamido]-adamantan-1-carboxylic acid amide

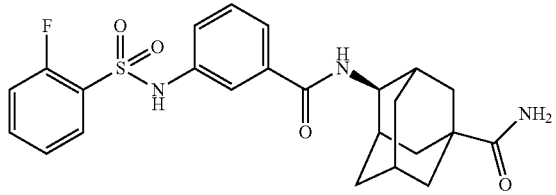

15 mg (0.03 mmol) of the 4-[3-(2-fluoro-benzenesulfonylamino)-benzamido]-adamantan-1-carboxylic acid prepared in Preparational Example 34 was dissolved in 5.0 ml of methylene chloride, to which 9 mg (0.045 mmol) of EDC and 6 mg (0.045 mmol) of HOBt were added. Then, ammonia water was also added thereto. The mixture was stirred at room temperature for 12 hours, followed by evaporation under reduced pressure to eliminate methylene chloride. The residue was dissolved in 10 ml of water, followed by extraction with 320 ml of methylene chloride. The extract was dried over anhydrous magnesium sulfate, and evaporated under reduced pressure, followed by column chromatography to give 6 mg of 4-[3-(2-fluoro-benzenesulfonylamino)-benzamido]-adamantan-1-carboxylic acid amide (yield: 43%).

$^1$H NMR (400 MHz, CDCl$_3$) δ 8.53 (s, 1H), 7.89-7.80 (m, 2H), 7.50 (s, 1H) 7.46-7.32 (m, 2H), 7.28-7.12 (m, 3H), 6.42 (s, 1H), 5.75 (s, 1H), 5.30 (s, 1H), 4.12 (s, 1H), 2.17-1.94 (m, 9H), 1.84-1.81 (m, 2H), 1.69-1.66 (m, 2H).

The compounds of Example 92-Example 139 were prepared by the preparation method described in Example 91.

TABLE 5

| Example | Compound Name | Structure | NMR data |
|---|---|---|---|
| 92 | E-4-[2-(2-fluoro-benzenesulfonyamino)-benzamido]-adamantan-1-carboxylic acid amide | 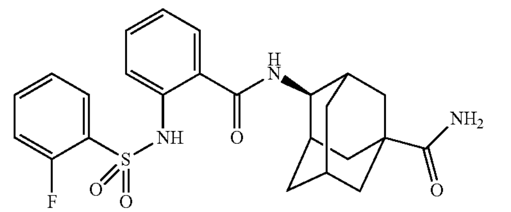 | ¹H NMR (400 MHz, CDCl₃) d 11.75 (brs, 1H), 7.95, (brs, 1H), 7.63-7.61 (m, 1H), 7.42 (s, 1H), 7.38-7.23 (m, 2H), 7.17-7.05 (m, 3H) 6.37 (s, 1H), 5.39 (s, 1H), 5.31 (s, 1H), 4.20 (s, 1H), 2.30-1.81 (m, 9H), 1.67-1.63 (m, 4H) |
| 93 | E-4-[4-(2-fluoro-benzenesulfonylamino)-benzamido]-adamantan-1-carboxylic acid amide | 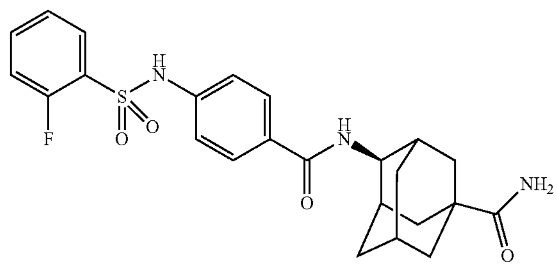 | ¹H NMR (400 MHz, MeOD) d 7.92 (s, 1H), 7.90-7.80 (m, 3H), 7.63-7.16 (m, 6H), 6.61 (s, 1H), 4.12 (s, 1H), 2.29-1.83 (m, 1H), 1.65-1.50 (m, 2H) |
| 94 | E-4-[3-(4-fluoro-benzenesulfonylamino)-benzamido]-adamantan-1-carboxylic acid amide | 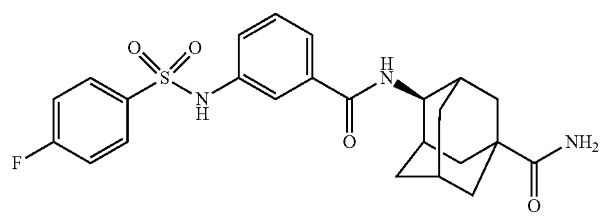 | ¹H NMR (400 MHz, (CDCl₃) d 8.70 (s, 1H), 7.84-7.76 (m, 3H), 7.55-7.50 (m, 1H), 7.41-7.32 (m, 2H) 7.11-7.05 9m, 2H0, 6.40 (d, 8.0 Hz, 1H), 5.44 (brs, 1H), 5.30 (brs, 1H), 4.40 (s, 1H), 2.18-2.09 (m, 5H), 2.01-1.95 (m, 4H), 1.85-1.82 (m, 2H), 1.70-1.67 (m, 2H) |
| 95 | E-4-[3-(3-chloro-benzenesulfonylamino)-benzamido]-adamantan-1-carboxylic acid amide | 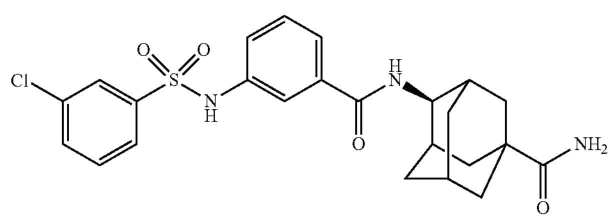 | ¹H NMR (400 MHz, CDCl₃) d 8.30 (brs, 1H), 7.80 (s, 1H), 7.50-7.30 (m, 5H), 6.45 (d, J = 8.0 Hz, 1H), 5.68 (hrs, 1H), 5.30 (brs, 1H), 4.39 (s, 1H), 2.19-2.10 (m, 5H), 2.02-1.95 (m, 4H), 1.85-1.82 (m, 2H), 1.71-1.68 (m, 2H) |
| 96 | E-4-[3-(3-chloro-2-methyl-benzenesulfonylamino)-benzamido]-adamantan-1-carboxylic acid amide | 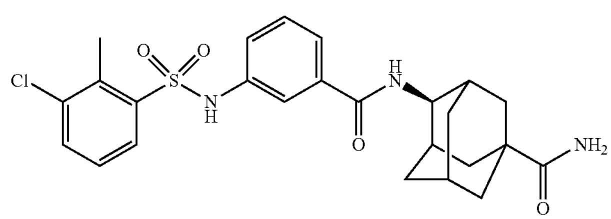 | ¹H NMR (400 MHz, CDCl₃) d 8.80 (s, 1H), 7.97 (d, J = 8.0 Hz, 1H), 7.84 (s, 1H), 7.54 (d, J = 4.0 Hz, 1H), 7.84 (s, 1H), 7.54 (d, J = 4.0 Hz, 1H), 7.44-7.19 (m, 3H), 6.46 (d, J = 8.0 Hz, 1H), 5.70 (brs, 1H), 5.30 (s, 3H), 4.42 (d, J = 8.0 Hz, 1H), 2.72 9s, 3H), 2.16-2.09 (m, 5H), 1.99-1.94 (m, 4H), 1.83-1.80 (m, 2H), 1.70-1.66 (m, 2H) |
| 97 | E-4-{3-[(3-chloro-benzenesulfonyl)-methylamino]-benzamido}-adamantan-1-carboxylic acid amide | 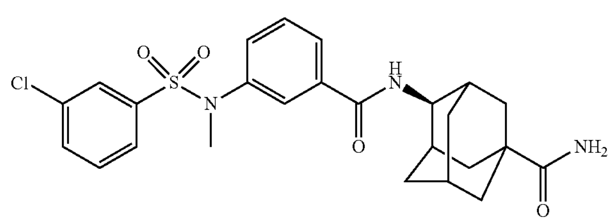 | ¹H NMR (400 MHz, CDCl₃) d 7.69 (d, J = 4.0 Hz, 1H), 7.60-7.51 (m, 3H), 7.44-7.28 (m, 3H), 6.32 (d, J = 8.0 Hz, 1H), 5.60 (brs, 1H), 5.26 (brs, 1H), 4.22 (d, J = 8.0 Hz, 1H), 3.22 (s, 3H), 2.20 (s, 2H), 2.10-1.95 (m, 7H), 1.87-1.83 (m, 2H), 1.71-1.67 (m, 2H) |

TABLE 5-continued

| Example | Compound Name | Structure | NMR data |
|---|---|---|---|
| 98 | E-4-[3-N-(2-hydroxyethyl)-2-(triflunromethyl-benzenesulfonylamino)benzamido]-adamantan-1-carboxylic acid amide | 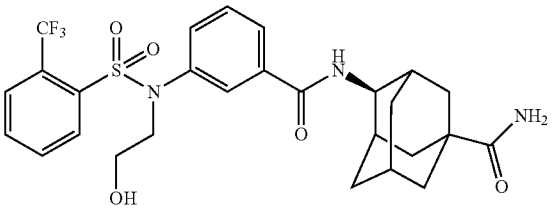 | ¹H NMR (400 MHz, CDCl₃) d 7.89 (d, J = 4.0 Hz, 1H), 7.83, (d, J = 4.0 Hz, 1H), 7.69-7.55 (m, 4H), 7.43-7.36 (m, 3H), 6.31 (d, J = 8.0 Hz, 1H), 5.62 (brs, 1H), 5.40 (brs, 1H), 4.18 (s, 1H), 3.92 (t, J = 8.0 Hz, 2H), 3.68 (s, 2H), 2.19 (s, 1H), 2.10-1.94 (m, 7H), 1.85-1.82 (m, 2H), 1.70-1.66 (m, 2H) |
| 99 | E-4-{3-[(2-trifluoromethyl-benzenesulfonyl)-methylamino]-benzamido}-adamantan-1-carboxylic acid amide | 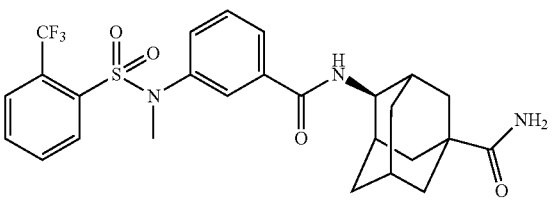 | ¹H NMR (400 MHz, CDCl₃) d 7.90 (d, J = 8.0 Hz, 1H), 7.79 (d, J = 4.0 Hz, 1H), 7.67-7.42 (m, 4H), 7.40-7.33 (m, 2H), 6.31 (d, J = 8.0 Hz, 1H), 5.59 (brs, 1H), 5.23 (brs, 1H), 4.21 (d, J = 8.0 Hz, 1H), 3.34 (s, 3H), 2.19-2.18 (m, 2H), 2.09-2.00 (m, 5H), 1.95-1.83 (m, 2H), 1.70-1.67 (m, 2H) |
| 100 | E-sodium[3-((5-carbamoyladamantan-2-yl)carbamoyl)phenyl](2-(trifluoromethyl)benzenesulfonylamide | 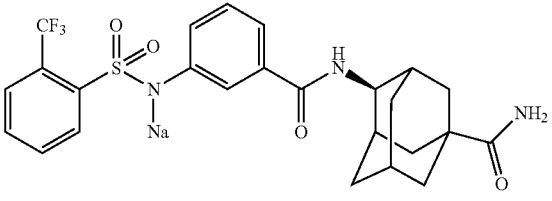 | ¹H NMR (400 MHz, DMSO) d 8.02 (H, J = 8.0 Hz, 1H), 7.75 (d, J = 4.0 Hz, 1H), 7.59-7.51 (m, 2H), 7.46 (d, J = 8.0 Hz, 1H), 7.12 (s, 1H), 7.06 (s, 1H), 7.00-6.72 (m, 3H), 6.70 (s, 1H), 4.20 (s, 1H), 1.98-1.74 (m, 1H) 1.42-1.39 (m, 2) |
| 101 | E-N-(5-carbamoyladamantan-2-yl)-5-[(N-methyl-2-(trifluoromethyl)benzenesulfonylamino]nicotinamide | 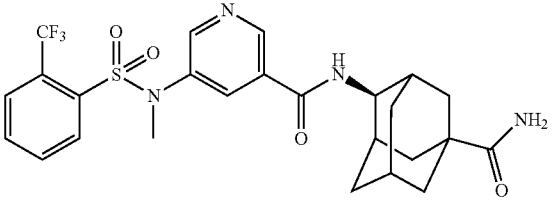 | ¹H NMR (400 MHz, CDCl₃) d 8.85 (s, 1H), 8.52, (s, 1H), 8.01-7.92 (m, 3H), 7.81-7.71 (m, 2H), 4.17 (s, 1H), 2.22 (s, 3H), 2.10-1.93 (m, 1H), 1.68-1.60 (s, 2H) |
| 102 | E-4-[3-(thiophen-2-sulfonylamino)-benzamido]-adamantan-1-carboxylic acid amide | 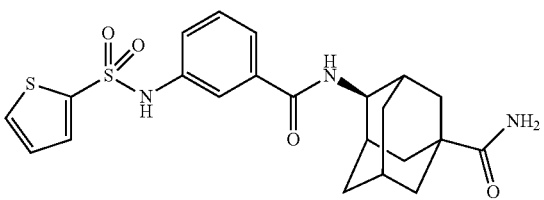 | ¹H NMR (400 MHz, DMSO) d 10.59 (brs, 1H), 7.93-7.84 (m, 2H), 7.53-7.29 (m, 5H), 7.10 (s, 1H), 7.02 (s, 1H), 6.74 (s, 1H), 3.93 (s, 1H), 2.09-2.02 (m, 4H), 1.91-1.77 (m, 7H), 1.44-1.41 (m, 2H) |
| 103 | E-4-[3-(furan-2-sulfonylamino)-benzamido]-adamantan-1-carboxylic acid amide | 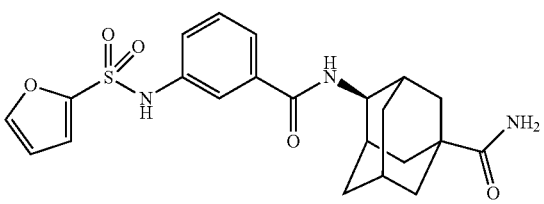 | ¹H NMR (400 MHz, DMSO) d 8.22 (s, 1H), 7.78 (s, 1H), 7.52-7.50 (m, 2H), 7.49-7.44 (m, 2H), 7.04-7.03 (m, 1H), 6.46-6.42 (m, 2H), 5.70 (s, 1H), 5.30 (s, 1H), 4.37-4.36 (m, 1H), 2.19-2.13 (m, 5H), 2.09-1.95 (m, 4H), 1.86-1.82 (m, 2H), 1.71-1.67 (m, 2H) |
| 104 | E-4-[3-(pyridin-3-sulfonylamino)-benzamido]-adamantan-1-carboxylic acid amide | 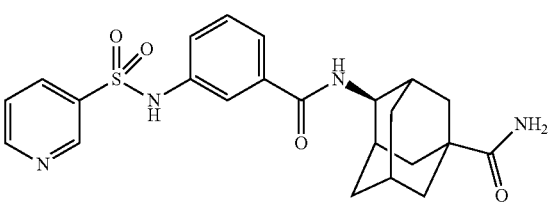 | ¹H NMR (400 MHz, DMSO) d 8.89-8.87 (m, 1H), 8.76 (d, J = 4.8 Hz, 1H), 8.13 (d, J = 8.0 Hz, 1H), 7.98 (s, 1H), 7.62-7.58 (m, 1H), 7.48-7.47 (m, 2H), 7.32 (t, J = 8.0 Hz, 1H), 7.26-7.24 (m, 1H), 7.06 (s, 1H), 6.75 (s, 1H), 3.91 (s, 1H), 2.08-1.97 (m, 4H), 1.90-1.67 (m, 7H), 1.43-1.40 (m, 2H) |

TABLE 5-continued

| Example | Compound Name | Structure | NMR data |
|---|---|---|---|
| 105 | E-4-(3-(benzenesulfonylamino-benzamido)-adamantan-1-carboxylic acid amide | 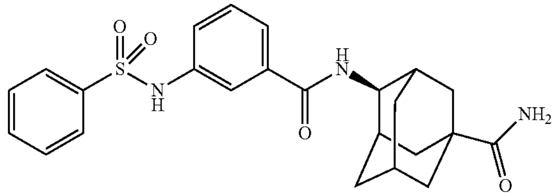 | ¹H NMR (400 MHz, DMSO) d 10.47 (brs, 1H), 7.97-7.92 (m, 1H), 7.77 (d, J = 8.0 Hz, 1H), 7.61-7.46 (m, 5H), 7.31-7.23 (m, 2H), 7.02 (s, 1H), 6.58 (s, 1H), 3.92 (s, 1H), 1.91-1.89 (m, 4H), 1.88-1.70 (m, 7H), 1.43-1.40 (m, 2H) |
| 106 | E-4-[3-[(2-chloro-benzenesulfonylamino]benzamido]-adamantan-1-carboxylic acid amide | 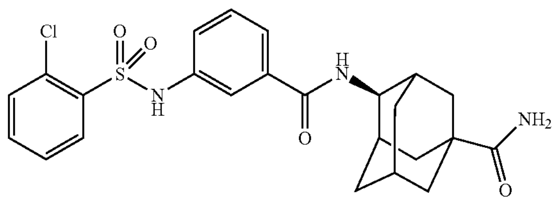 | ¹H NMR (400 MHz, DMSO) d 10.90 (brs, 1H), 8.04-7.90 (m, 2H), 7.60-7.40 (m, 5H), 7.30-7.20 (m, 2H), 7.05 (s, 1H), 6.70 (s, 1H), 4.00 (s, 1H), 2.00-1.95 (m, 4H), 1.90-1.80 (m, 5H), 1.75-1.70 (m, 2H), 1.45-1.40 (m, 2H) |
| 107 | E-4-[3-[(2,4-dimethyl-thiazol-5-sulfonylamino)-benzamido]-adamantan-1-carboxylic acid amide | 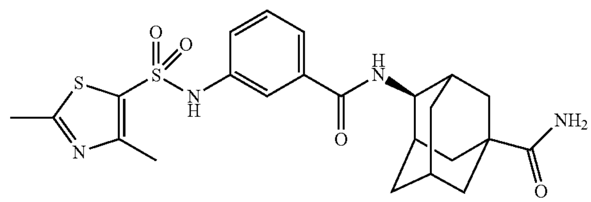 | ¹H NMR (400 MHz, DMSO) d 10.70 (brs, 1H), 7.93 (d, J = 6.4 Hz, 1H), 7.48-7.45 (m, 2H), 7.31 (t, J = 8.0 Hz, 1H), 7.30-7.24 (m, 2H), 7.06 (s, 1H), 6.74 (s, 1H), 2.57 (s, 3H), 2.40 (s, 1H), 2.08-2.00 (m, 4H), 1.90-1.75 (m, 7H), 1.48-1.40 (m, 2H) |
| 108 | E-4-[3-(3,5-dimethyl-1H-pyrazole-4-sulfonylamino)-benzamido]-adamantan-1-carboxylic acid amide | 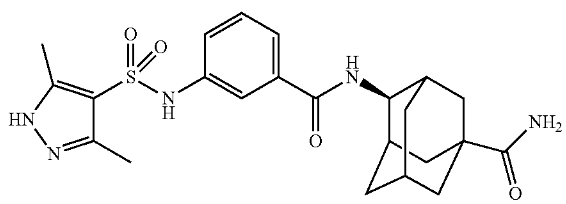 | ¹H NMR (400 MHz, DMSO) d 12.98 (brs, 1H), 10.33 (brs, 1H), 7.93 (d, J = 6.4 Hz, 1H), 7.48-7.45 (m, 2H), 7.31 (t, J = 8.0 Hz, 1H), 7.17-7.15 (m, 1H), 7.06 (s, 1H), 6.74 (s, 1H), 4.26-4.24 (m, 1H), 2.24 (s, 6H), 2.08-2.00 (m, 4H), 1.88-1.75 (m, 7H), 1.43-1.41 (m, 2H) |
| 109 | E-N-(5-hydroxy-adamantan-2-yl)-3-benzenesulfonylamino-benzamide | 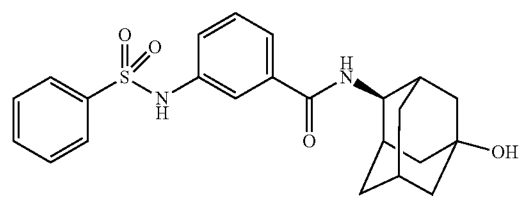 | ¹H NMR (400 MHz, CDCl₃) d 8.02 (s, 1H), 7.88 (d, J = 8.0 Hz, 1H), 7.79 (d, J = 8.0 Hz, 1H), 7.46 (t, J = 8.0 Hz, 1H), 7.20-7.16 (m, 2H), 7.07-7.03 (m, 3H), 6.66 (s, 1H), 4.07 (s, 1H), 2.17-2.14 (m, 3H), 1.88-1.85 (m, 2H), 1.77-1.70 (m, 6H), 1.53-1.50 (m, 2H) |
| 110 | E-N-cycloheptyl-3-phenylsulfamoyl-benzamide | 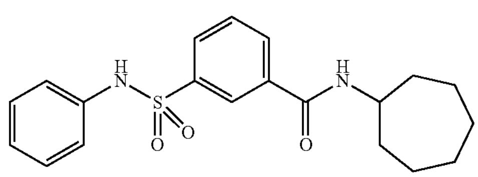 [SMILES: O=C(NC1CCCCCC1)c1cccc(S(=O)(=O)Nc2ccccc2)c1] | ¹H NMR (400 MHz, CDCl₃) d 8.12 (s, 1H), 7.99 (d, J = 8.0 Hz, 1H), 7.83 (d, J = 8.0 Hz, 1H), 7.52 (t J = 8.0 Hz, 1H), 7.20-7.11 (m, 3H), 6.97 (s, 1H), 6.03 (s, 1H), 4.15-4.12 (m, 1H), 2.07-1.98 (m, 2H), 1.67-1.40 (m, 10H) |
| 111 | E-N-(5-hydroxyadamantan-2-yl)-3-(2-(trifluoromethyl)benzenesulfonylamino)benzamide | 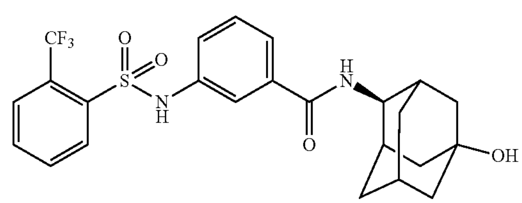 | ¹H NMR (400 MHz, CDCl₃) d 8.07 (d, J = 8.0 Hz, 1H), 7.92 (d, J = 8.0 Hz, 1H), 7.70-7.52 (m, 2H), 7.51-7.49 (m, 2H), 7.36-7.31 (m, 2H), 6.87 (brs, 1H), 6.22 (d, J = 6.4 Hz, 1H), 4.20-4.18 (m, 1H), 2.24-2.20 (m, m, 3H), 1.97-1.94 (m, 2H), 1.84-1.74 (m, 6H), 1.61-1.60 (m, 2H) |

TABLE 5-continued

| Example | Compound Name | Structure | NMR data |
|---|---|---|---|
| 112 | E-4-(3-(N-phenylsulfamoyl-benzamino)-adamantan-1-carboxylic acid amide | 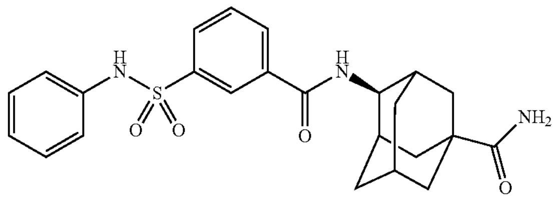 | $^1$H NMR (400 MHz, DMSO) d 10.40 (brs, 1H), 8.24 (d, J = 6.4 Hz, 1H), 8.16 (s, 1H), 8.03 (d, J = 6.4 Hz, 1H), 7.86 (d, J = 8.8 Hz, 1H), 7.61 (t, J = 8.0 Hz, 1H), 7.38-7.20 (m, 2H), 7.09-7.01 (m, 4H), 6.75 (s, 1H), 3.97-3.96 (m, 4H), 2.09-2.05 (m, 4H), 1.91-1.76 (m, 17H), 1.45-1.42 (m, 2H) |
| 113 | E-sodium[3-((5-carbamoyladamantan-2-yl)carbamoyl)phenyl]-2-fluoro-3-chloro-benzenesulfonylamide | 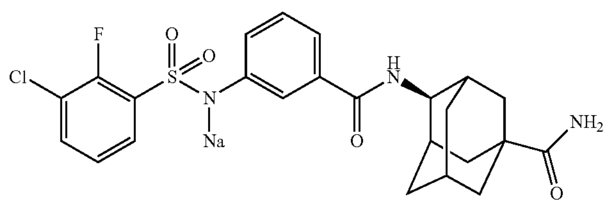 | $^1$H NMR (400 MHz, DMSO) d 7.69-7.65 (m, 1H), 7.54-7.51 (m, 2H), 7.17-7.13 (m, 2H), 7.03 (brs, 1H), 6.97-6.92 (m, 3H), 6.73 (brs, 1H), 3.90 (brs, 1H) 2.09-2.01 (m, 4H), 1.99-1.73 (m, 7H), 1.43-1.40 (m, 2H) |
| 114 | E-4-[3-(3-chloro-4-(trifluoromethyl)benzenesulfonylamino)benzamido]adamantan-1-carboxylic acid amide | 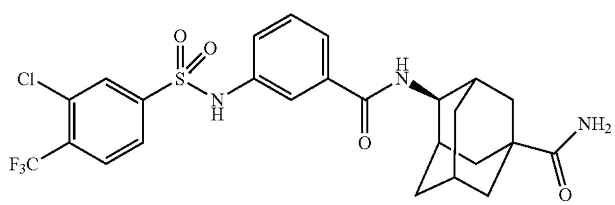 | $^1$H NMR (400 MHz, DMSO) d 11.07 (s, 1H), 8.25 (d, J = 4.2 Hz, 1H), 8.15 (s, 1H), 7.93 (t, J = 4 Hz, 2H), 7.50-7.48 (m, 1H), 7.32 (t, J = 4 Hz, 1H), 7.24 (d, J = 6 Hz, 1H), 7.02 (s, 1H), 6.75 (s, 1H), 3.91 (d, J = 3 Hz, 1H), 2.01-1.89 (m, 4H), 1.85-1.80 (m, 5H), 1.76 (s, 2H), 1.41 (d, J = 6.2 Hz, 2H) |
| 115 | E-4-[3-[(2-(trifluoromethyl)benzenesulfonylamino]-benzamido]-adamantan-1-carboxylic acid amide | 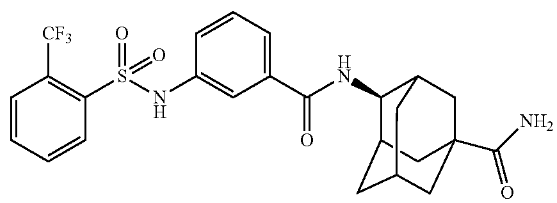 | $^1$H NMR (400 MHz, DMSO) d 10.86 (s, 1H), 8.09 (d, J = 7.2 Hz, 1H), 8.00 (d, J = 7.2 Hz, 1H), 7.92 (d, J = 6.4 Hz, 1H), 7.88-7.83 (d, 2H), 7.48 (d, J = 11.6 Hz, 2H), 7.32 (t, J = 7.6 Hz, 1H), 7.22 (d, J = 8 Hz, 1H), 7.01 (s, 1H), 6.74 (s, 1H), 3.92 (d, J = 5.6 Hz, 1H), 2.01 (s, 4H), 1.91-1.76 (m, 7H), 1.42 (d, J = 12 Hz, 2H) |
| 116 | E-4-[3-(2-chloro-4-bromo-benzenesulfonylamino)-benzamido]-adamantan-1-carboxylic acid amide | 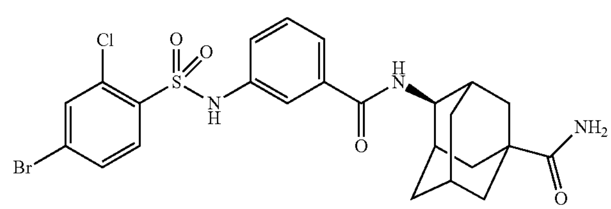 | $^1$H NMR (400 MHz, DMSO) d 10.91 (s, 1H), 7.94 (d, J = 15.6 Hz, 3H), 7.74 (d, J = 8.6 Hz, 1H), 7.45 (s, 2H), 7.25 (t, J = 8 Hz, 1H), 7.19 (d, J = 7.6 Hz, 1H), 7.02 (s, 1H), 6.75 (s, 1H), 4.12 (d, J = 5.2 Hz, 1H), 1.20 (d, J = 5.4 Hz, 4H), 1.91 (s, 2H), 1.84 (d, J = 6.4 Hz, 3H), 1.76 (s, 2H), 1.42 (d, J = 12 Hz, 2H) |
| 117 | E-4-[3-(2,4,6-trichloro-benzenesulfonylamino)-benzamido]-adamantan-1-carboxylic acid amide | 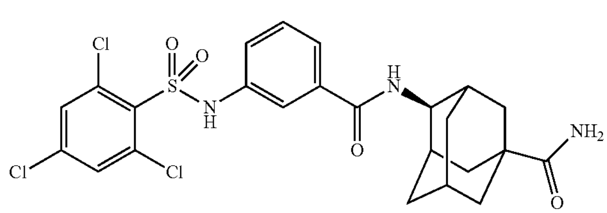 | $^1$H NMR (400 MHz, DMSO) d 11.09 (s, 1H), 7.99-7.90 (m, 2H), 7.46 (s, 2H), 7.33 (t, J = 8 Hz, 1H), 7.20 (d, J = 8.4 Hz, 2H), 7.02 (s, 1H), 6.75 (s, 1H), 3.91 (d, J = 5.6 Hz, 1H), 2.00 (d, J = 7.6 Hz, 5H), 1.87 (d, J = 14.4 Hz, 3H), 1.76 (s, 2H), 1.42 (d, J = 12 Hz, 2H) |
| 118 | E-4-[3-(3-chloro-5-fluoro-benzenesulfonylamino)-benzamido]-adamantan-1-carboxylic acid amide | 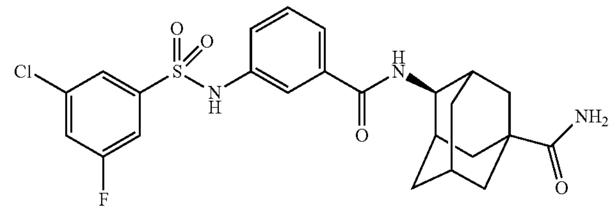 | $^1$H NMR (400 MHz, DMSO) d 10.60-10.53 (m, 1H), 7.981-7.949 (m, 2H), 7.94 (m, 1H), 7.63 (t, J = 4.4 Hz, 1H), 7.54 (m, 2H), 7.26 (d, J = 2 Hz, 1H), 7.03 (s, 1H), 6.76 (s, 1H), 3.93 (t, J = 2 Hz, 1H), 2.00 (d, J = 3.4 Hz, 4H), 1.91-1.76 (m, 7H), 1.42 (d, J = 6.4 Hz, 2H) |

TABLE 5-continued

| Example | Compound Name | Structure | NMR data |
|---|---|---|---|
| 119 | E-4-[3-(3,5-dichloro-benzenesulfonylamino)-benzamido]-adamantan-1-carboxylic acid amide | 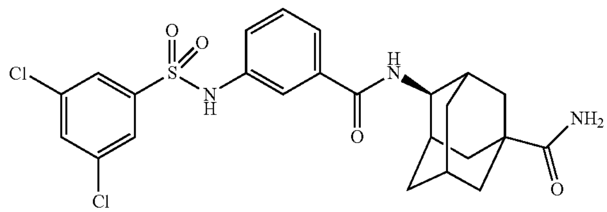 | $^1$H NMR (400 MHz, DMSO) d 7.89 (s, 2H), 7.70 (s, 2H), 7.41 (s, 2H), 7.31 (s, 1H), 7.21 (d, J = 7.2 Hz, 1H), 7.03 (s, 1H), 6.74 (s, 1H), 4.14 (d, J = 6.4 Hz, 1H), 2.06 (d, J = 27.6 Hz, 7H), 1.91 (s, 3H), 1.43 (d, J = 11.6 Hz, 3H) |
| 120 | E-4-[3-(3-fluoro-benzenesulfonylamino)-benzamido]-adamantan-1-carboxylic acid amide | 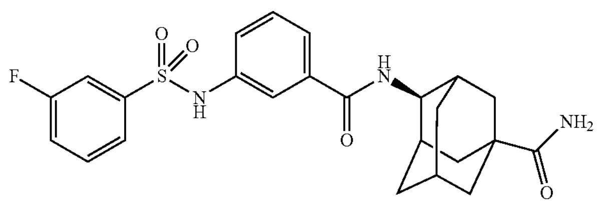 | $^1$H NMR (400 MHz, DMSO) d 10.74 (s, 1H), 7.99 (d, J = 6.4 Hz, 1H), 7.66 (d, J = 7.6 Hz, 2H), 7.59 (d, J = 8.4 Hz, 1H), 7.53 (d, J = 7.6 Hz, 3H), 7.37-7.27 (m, 2H), 7.06 (s, 1H), 6.78 (s, 1H), 3.96 (s, 1H), 2.04 (s, 4H), 1.98-1.78 (m, 8H), 1.47 (d, J = 12.4 Hz, 2H) |
| 121 | E-4-[3-(2,4-difluoro-benzenesulfonylamino)-benzamido]-adamantan-1-carboxylic acid amide | 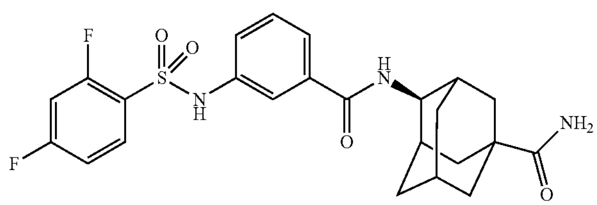 | $^1$H NMR (400 MHz, CDCl$_3$) d 8.00 (s, 1H), 7.91-7.86 (m, 1H), 7.73 (t, 1H), 7.43-7.41 (m, 2H), 7.33 (t, 1H), 7.00-6.88 (m, 2H), 6.40 (d, J = 7.6 Hz, 1H), 5.67 (s, 1H), 5.35 (s, 1H), 4.34 (d, J = 7.6 Hz, 1H), 2.14 (t, 6H), 2.03 (t, 6H), 1.85 (d, J = 14.4 Hz, 2H), 1.70 (d, J = 12.4 Hz, 2H) |
| 122 | E-4-[3-(2,5-difluoro-benzenesulfonylamino)-benzamido]-adamantan-1-carboxylic acid amide | 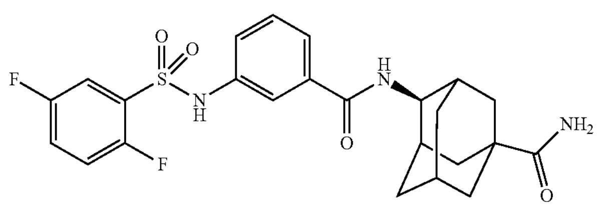 | $^1$H NMR (400 MHz, DMSO) d 10.96 (s, 1H), 8.01 (d, J = 6.4 Hz, 1H), 7.68-7.61 (m, 2H), 7.58-7.54 (m, 3H), 7.39-7.29 (m, 2H), 7.05 (s, 1H), 6.78 (s, 1H), 3.95 (s, 1H), 2.04 (s, 1H), 1.92-1.79 (m, 8H), 1.47 (d, J = 12.0 Hz, 2H) |
| 123 | E-4-[3-(2,6-difluoro-benzenesulfonylamino)-benzamido]-adamantan-1-carboxylic acid amide | 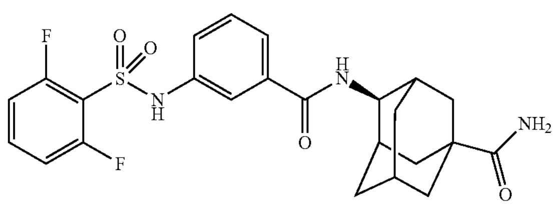 | $^1$H NMR (400 MHz, DMSO) d 11.12 (s, 1H), 7.97 (s, 1H), 7.71 (s, 1H), 7.54 (d, J = 22.8 Hz, 2H), 7.35-7.29 (m, 4H), 7.06 (s, 1H), 6.78 (s, 1H), 3.96 (s, 1H), 2.04 (s, 4H), 1.94-1.79 (m, 7H), 1.47 (d, J = 12.0 Hz, 2H) |
| 124 | E-N-cycloheptyl-N-propyl-3-(2-(trifluoromethyl)benzenesulfonylamino)benzamide | 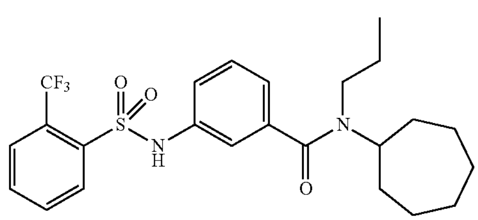 [SMILES: CCCN(C(=O)c1cccc(NS(=O)(=O)c2ccccc2C(F)(F)F)c1)C1CCCCCC1] | $^1$H NMR (400 MHz, CDCl$_3$) d 8.03 (d, J = 8.0 Hz, 1H), 7.87 (d, J = 8.0 Hz, 1H), 7.64 (t, 1H), 7.55 (t, 1H), 7.28-7.22 (m, 2H), 7.17-7.13 (m, 1H), 7.05 (t, 2H), 3.47 (s, 1H), 3.24 (t, 1H), 2.98 (s, 1H), 1.86-1.60 (m, 10H), 1.40 (s, 4H), 1.28 (d, J = 7.6 Hz, 2H), 1.14 (s, 2H), 1.02-0.69 (m, 3H), 0.59 (s, 1H) |
| 125 | E-4-[2-fluoro-3-(2-(trifluoromethyl)benzenesulfonylamino)benzamido]adamantan-1-carboxylic acidamide | 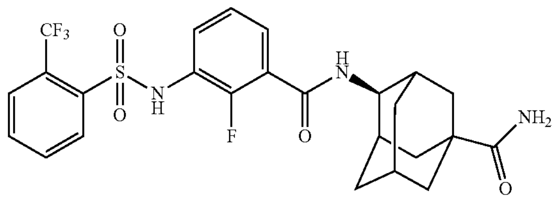 | $^1$H NMR (400 MHz, CDCl$_3$) d 8.03 (t, J = 8.0 Hz, 1H), 7.91 (d, J = 7.6 Hz, 1H), 7.77 (td, J$_1$ = 1.6 Hz, J$_2$ = 6.4 Hz, 1H), 7.73 (m, 1H), 7.62 (t, J = 7.6 Hz, 1H), 6.97 (s, 1H), 6.63 (t, J = 7.2 Hz, 1H), 5.57 (brs, 1H), 5.21 (brs, 1H), 4.20 (d, J = 4.8 Hz, 1H), 2.22-1.64 (m, 13H) |

TABLE 5-continued

| Example | Compound Name | Structure | NMR data |
|---|---|---|---|
| 126 | E-4-[2-chloro-5-(3-chlorobenzenesulfonylamino)benzamido]adamantan-1-carboxylic acidamide | 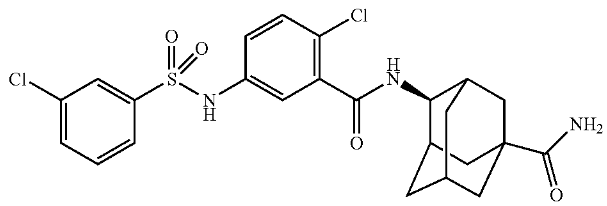 | $^1$H NMR (400 MHz, CDCl$_3$) d 9.04 (s, 1H), 7.79 (t, 1H), 7.69-7.66 (m, 2H), 7.52-7.47 (m, 2H), 7.39-7.33 (m, 2H), 7.08 (d, J = 7.6 Hz, 1H), 5.75 (s, 1H), 5.37 (s, 1H), 4.43 (d, J = 8.0 Hz, 1H), 2.36-2.15 (m, 4H), 2.09 (s, 1H), 1.98 (t, 4H), 1.87-1.79 (m, 3H), 1.69 (d, J = 12.4 Hz, 2H) |
| 127 | E-4-[3-(3-chlorobenzenesulfonyl-amino)-4-fluorobenzamido]adamantan-1-carboxylic acidamide | 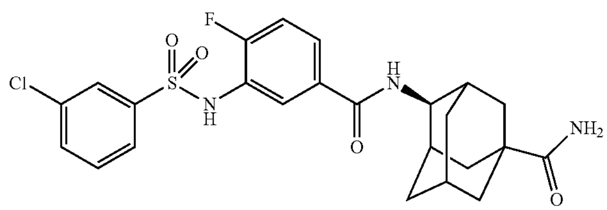 | $^1$H NMR (400 MHz, DMSO) d 10.50 (s, 1H), 8.14 (s, 1H), 7.93-7.56 (m, 6H), 7.22 (t, 1H), 7.02 (s, 1H), 6.74 (s, 1H), 3.94 (d, J = 5.2 Hz, 1H), 2.02 (s, 4H), 1.92-1.69 (m, 8H), 1.44 (d, J = 12.4 Hz, 2H) |
| 128 | E-4-[4-chloro-3-(3,5-dichlorobenzenesulfonyl-amino)benzamido]adamantan-1-carboxylic acidamide | 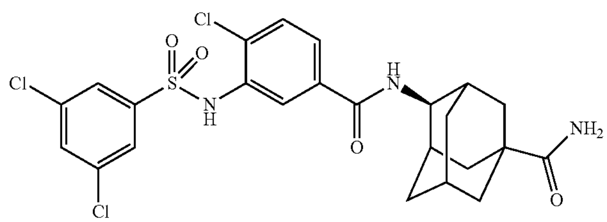 | $^1$H NMR (400 MHz, CDCl$_3$) d 7.38-7.26 (m, 1H), 7.23 (d, J = 2 Hz, 1H), 7.00-6.97 (m, 1H), 6.31 (d, J = 7.2 Hz, 1H), 5.64 (s, 1H), 5.01 (s, 1H), 2.33-1.42 (m, 11H) |
| 129 | E-4-[2-chloro-5-(3,5-dichlorobenzenesulfonyl-amino)benzamido]adamantan-1-carboxylic acidamide | 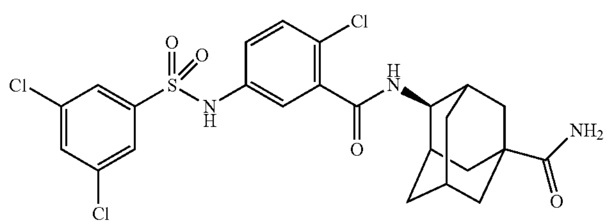 | $^1$H NMR (400 MHz, CDCl$_3$) d 7.67-7.63 (m, 3H), 7.55-7.47 (m, 2H), 7.38 (d, J = 8.8 Hz, 1H), 7.15 (d, J = 8.0 Hz, 1H), 5.80 (s, 1H), 5.62 (s, 1H) 4.43 (d, J = 8.0 Hz, 1H), 2.21-1.60 (m, 14H) |
| 130 | E-4-[3-(3,5-dichlorobenzenesulfonyl-amino)-4-fluorobenzamido]adamantan-1-carboxylic acidamide | 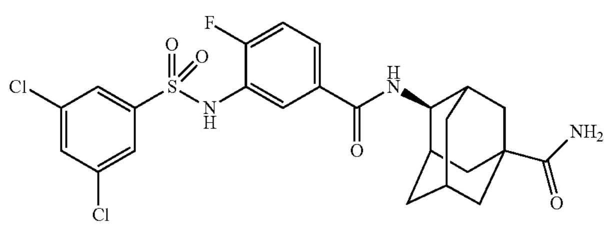 | $^1$H NMR (400 MHz, CDCl$_3$) d 7.26-7.21 (m, 1H), 7.03-6.99 (m, 2H), 6.27 (d, J = 7.2 Hz, 1H), 5.60 (s, 1H), 5.33 (s, 1H), 4.22 (d, J = 7.2 Hz, 1H), 3.87 (s, 2H), 3.75-3.61 (m, 1H), 2.37-1.56 (m, 15H) |
| 131 | E-4-[5-(3,5-dichlorobenzenesulfonyl-amino)-2-fluorobenzamido]adamantan-1-carboxylic acidamide | 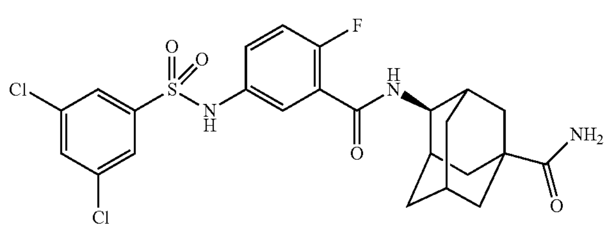 | $^1$H NMR (400 MHz, CDCl$_3$) d 8.90 (s, 1H), 7.95-7.92 (m, 1H), 7.71-7.67 (m, 1H), 7.63 (d, J = 2.0 Hz, 2H), 7.46 (t, 1H), 7.18-7.13 (m, 1H), 5.68 (s, 1H), 5.30 (s, 1H), 4.55 (d, J = 8.0 Hz, 1H), 2.32 (t, 4H), 2.19 (d, J = 6.0 Hz, 1H), 2.01-1.95 (t, 4H), 1.86 (d, J = 13.2 Hz, 2H), 1.71 (d, J = 13.6 Hz, 1H) |
| 132 | E-4-[2-fluoro-3-(3-chlorobenzenesulfonylamino)benzamido]adamantan-1-carboxylic acidamide | 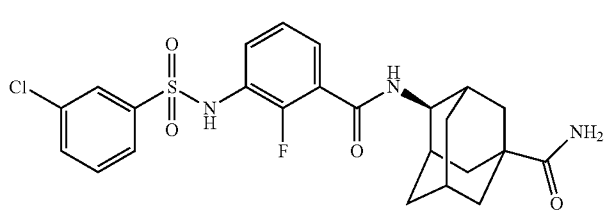 | $^1$H NMR (400 MHz, CDCl$_3$) d 7.84 (m, 2H), 7.68 (m, 2H), 7.56 (m, 1H), 7.43 (d, J = 8.0 Hz, 1H), 7.26 (m, 1H), 6.68 (m, 1H), 5.66 (brs, 1H), 5.50 (brs, 1H), 4.23 (d, J = 4.8 Hz, 1H), 2.19 (s, 2H), 2.07 (m, 5H), 1.94 (m, 2H), 1.76 (d, J = 13.6 Hz, 1H), 1.66 (d, J = 13.2 Hz, 1H) |

TABLE 5-continued

| Example | Compound Name | Structure | NMR data |
|---|---|---|---|
| 133 | E-4-[2-chloro-5-(3-chloro-4-methoxybenzenesulfonyl-amino)benzamido]adamantan-1-carboxylic acidamide | 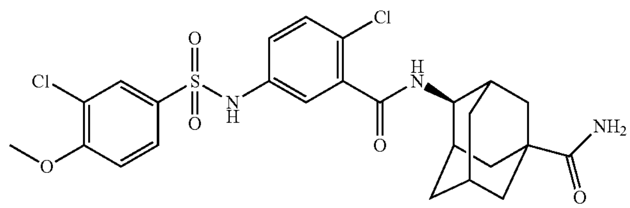 | $^1$H NMR (400 MHz, CDCl$_3$) d 7.80 (d, J = 2.4 Hz, 1H), 7.68 (dd, J = 8.8, 2.4 Hz, 1H), 7.63 (d, J = 2.8, 1H), 7.46 (dd, J = 6.4, 1.6 Hz, 1H), 7.30 (d, J = 8.4 Hz, 1H), 7.01 (d, J = 8.0 Hz, 1H), 6.90 (d, J = 8.8 Hz, 1H), 5.92 (brs, 1H), 5.73 (brs, 1H), 4.37 (d, J = 7.6 Hz, 1H), 3.91 (s, 3H), 2.17 (m, 4H), 2.07 (s, 1H), 1.97 (d, J = 12.4 Hz, 1H), 1.93 (s, 2H), 1.84 (d, J = 13.2 Hz, 2H), 1.65 (d, J = 13.2 Hz, 2H) |
| 134 | E-4-[4-chloro-3-(3-chloro-4-methoxybenzenesulfonyl-amino)benzamido]adamantan-1-carboxylic acidamide | 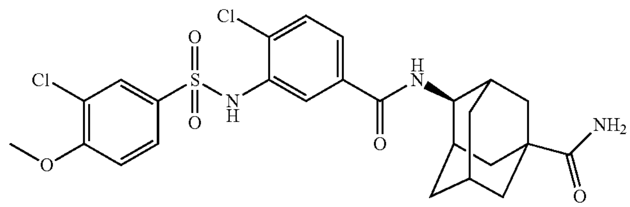 | $^1$H NMR (400 MHz, CDCl$_3$) d 7.94 (d, J = 2.0 Hz, 1H), 7.80 (m, 1H), 7.66 (td, J = 2.4, 4.1 Hz, 1H), 7.53 (dd, J = 6.4, 2.0 Hz, 1H), 7.37 (d, J = 8.0 Hz, 1H), 6.92 (d, J = 8.8 Hz, 1H), 6.32 (d, J = 7.2 Hz, 1H), 5.56 (d, J = 33.2 Hz, 2H), 4.22 (m, 1H), 3.94 (s, 3H), 2.22-1.69 (m, 13H) |
| 135 | E-4-[5-(3-chloro-4-methoxybenzenesulfonyl-amino)-2-fluorobenzamido]adamantan-1-carboxylic acidamide | 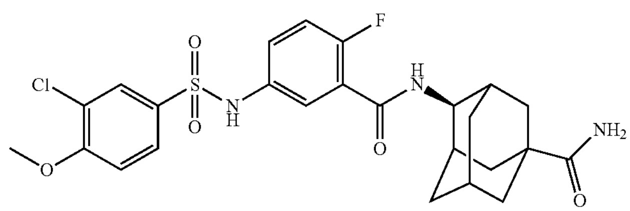 | $^1$H NMR (400 MHz, CDCl$_3$) d 8.47 (brs, 1H), 7.90 (dd, J = 4.0, 2.8 Hz, 1H), 7.71 (d, J = 2.4 Hz, 1H), 7.65 (m, 2H), 7.32 (m, 1H), 7.11 (m, 1H), 6.88 (d, J = 8.8 Hz, 1H), 5.71 (brs, 1H), 5.30 (brs, 1H), 4.52 (d, J = 7.6 Hz, 1H), 3.91 (s, 3H), 2.17 (m, 4H), 2.05 (s, 1H), 1.97 (m, 4H), 1.82 (d, J = 13.2 Hz, 2H), 1.66 (d, J = 13.2 Hz, 2H) |
| 136 | E-4-(3-(4-chloro-benzenesulfonylamino-benzamido)-adamantan-1-carboxylic acid amide | 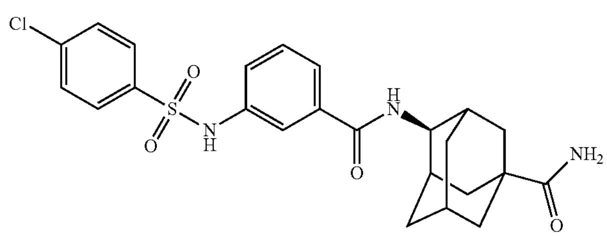 | $^1$H NMR (400 MHz, DMSO) d 10.54 (s, 1H), 7.94 (d, J = 6.4 Hz, 1H), 7.78-7.75 (m, 2H), 7.66-7.63 (m, 2H), 7.52-7.49 (m, 2H), 7.32 (t, J = 7.8 Hz, 1H), 7.24 (dd, J = 8, 1.2 Hz, 1H), 7.01 (s, 1H), 6.73 (s, 1H), 3.94-3.93 (m, 1H), 2.05-1.76 (m, 11H), 1.42 (d, J = 12.8 Hz, 2H) |
| 137 | E-4-(3-(2,4,5-trifluoro-benzenesulfonylamino-benzamido)-adamantan-1-carboxylic acid amide | 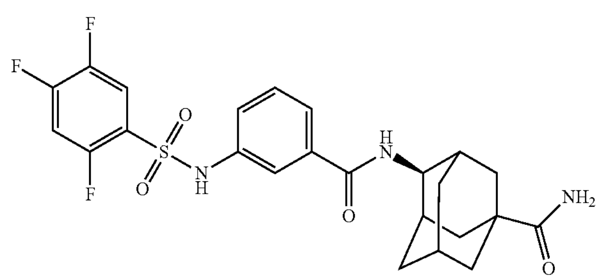 | $^1$H NMR (400 MHz, DMSO) d 10.96 (s, 1H), 7.84-7.98 (m, 3H), 7.48-7.53 (m, 2H), 7.35 (t, J = 8.0 Hz, 1H), 7.26 (dd, J = 8.4, 1.2 Hz, 1H), 7.02 (brs, 1H), 6.75 (brs, 1H), 3.78 (d, J = 6.0 Hz, 1H), 1.84-2.02 (m, 9H), 1.76 (s, 2H), 1.42 (d, J = 12.8 Hz, 2H) |
| 138 | E-4-(3-(cyclopropanesulfon-amido)benzamido)adamantan-1-carboxylic acid amide | 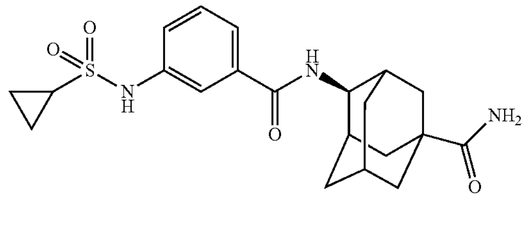 | $^1$H NMR (400 MHz, CDCl$_3$) d 7.93 (s, 1H), 7.86 (brs, 1H), 7.62 (d, J = 7.6 Hz, 1H), 7.40-7.48 (m, 2H), 6.51 (d, J = 8.0 Hz, 1H), 5.77 (brs, 1H), 5.51 (brs, 1H), 4.35 (d, J = 8.0 Hz, 1H), 2.47-2.54 (m, 1H), 2.09-2.19 (m, 4H), 2.00-2.03 (m, 2H), 1.95 (s, 2H), 1.86 (d, J = 13.2 Hz, 2H), 1.69 (d, J = 12.8 Hz, 2H), 1.16-1.20 (m, 2H), 0.93-0.99 (m, 2H) |

TABLE 5-continued

| Example | Compound Name | Structure | NMR data |
|---|---|---|---|
| 139 | E-4-(3-(1-methylethylsulfonamido)benzamido)adamantan-1-carboxylic acid amide | 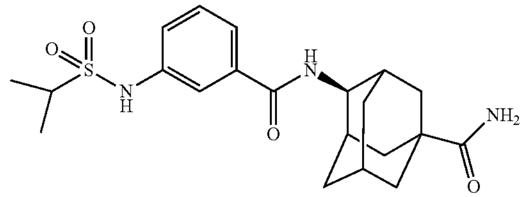 | $^1$H NMR (400 MHz, CDCl$_3$) d 8.54 (s, 1H), 7.98 (s, 1H), 7.66-7.69 (m, 1H), 7.37-7.41 (m, 1H), 6.56 (d, J = 8.0 Hz, 1H), 5.91 (brs, 1H), 5.73 (brs, 1H), 4.39 (d, J = 7.6 Hz, 1H), 3.26-3.32 (m, 1H), 2.19 (d, J = 12.0 Hz, 4H), 1.92-2.04 (m, 5H), 1.86 (d, J = 13.2 Hz, 2H), 1.69 (d, J = 12.8 Hz, 2H), 1.38 (d, J = 6.8 Hz, 6H) |

Preparational Example 35

Preparation of 4-[(1-[3,4-dihydro-1H-isoquinolin-2-carbonyl)-amino]-methyl-cyclopropanecarbonyl)-amino]-adamantan-1-carboxylic acid methyl ester

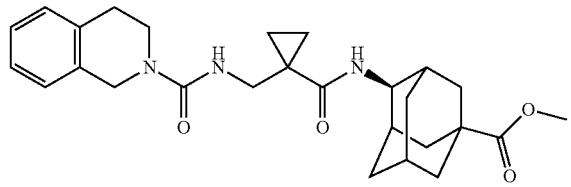

30 mg (0.1 mmol) of 4-[(1-aminomethyl-cyclopropanecarbonyl-amino]-adamantane-1-carboxylic acid methyl ester was dissolved in 1.0 ml of chloroform, to which 16 mg (0.1 mmol) of carbodiimide and TEA were added. Then, 14 mg (0.1 mmol) of 1,2,3,4-tetrahydroisoquinoline was also added thereto. The mixture was stirred for 12 hours with reflux, followed by evaporation under reduced pressure to eliminate chloroform. The residue was dissolved in 10 ml of water, followed by extraction with 320 ml of ethyl acetate. The extract was dried over anhydrous magnesium sulfate, and evaporated under reduced pressure, followed by column chromatography to give 30 mg of 4-[(1-[3,4-dihydro-1H-isoquinolin-2-carbonyl)-amino]-methyl-cyclopropanecarbonyl)-amino]-adamantan-1-carboxylic acid methyl ester (yield: 65%).

$^1$H NMR (400 MHz, CDCl$_3$) δ 7.63 (d, J=7.2 Hz, 1H), 7.29-7.10 (m, 4H), 4.94-4.91 (m, 1H), 4.55 (s, 2H), 4.00-3.82 (m, 1H), 3.65 (s, 3H), 3.62-3.53 (m, 4H), 2.87 (t, J=6.4 Hz, 2H), 2.19-1.74 (m, 11H), 1.48-1.42 (m, 2H), 0.90-0.87 (m, 2H), 0.71-0.68 (m, 2H).

Preparational Example 36

Preparation of 4-[(1-[3,4-dihydro-1H-isoquinolin-2-carbonyl)-amino]-methyl-cyclopropanecarbonyl)-amino]-adamantan-1-carboxylic acid

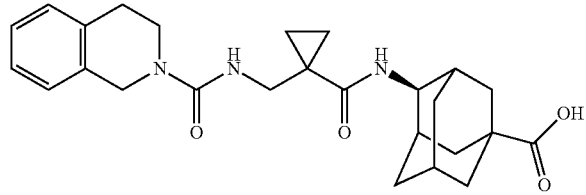

25 mg (0.05 mmol) of the 4-[(1-[3,4-dihydro-1H-isoquinolin-2-carbonyl)-amino]-methyl-cyclopropanecarbonyl)-amino]-adamantan-1-carboxylic acid methyl ester prepared in Preparational Example 35 was dissolved in 1.0 ml of methanol and 1.0 ml of water, to which 20 mg (0.5 mmol) of sodium hydroxide was added. The mixture was stirred at room temperature for 12 hours, followed by evaporation under reduced pressure to eliminate methanol. The residue was acidized with 1 N HCl, followed by extraction with 320 ml of chloroform. The extract was dried over anhydrous magnesium sulfate, followed by evaporation under reduced pressure. The obtained compound proceeded to the next reaction without purification.

Example 140

Preparation of E-[3,4-dihydro-1H-isoquinolin-2-carboxylic acid-1-[(5-carbamoyl-adamantan-2-ylcarbamoyl)cyclopropyl methyl]-amide

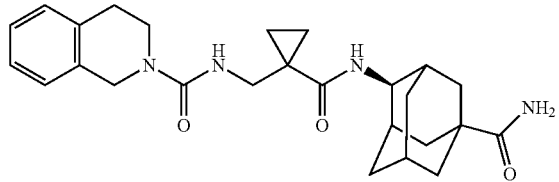

15 mg (0.03 mmol) of the 4-[(1-[3,4-dihydro-1H-isoquinolin-2-carbonyl)-amino]-methyl-cyclopropanecarbonyl)-amino]-adamantan-1-carboxylic acid prepared in Preparational Example 36 was dissolved in 5.0 ml of methylene chloride, to which 11 mg (0.06 mmol) of EDC and 8 mg (0.06 mmol) of HOBt were added, and then ammonia water was also added thereto. The mixture was stirred at room temperature for 12 hours, followed by evaporation under reduced pressure to eliminate methylene chloride. The residue was dissolved in 10 ml of water, followed by extraction with 320 ml of methylene chloride. The extract was dried over anhydrous magnesium sulfate, and evaporated under reduced pressure, followed by column chromatography to give 7 mg of [3,4-dihydro-1H-isoquinolin-2-carboxylic acid-1-[(5-carbamoyl-adamantan-2-ylcarbamoyl)cyclopropylmethyl]-amide (yield: 50%).

$^1$H NMR (400 MHz, CDCl$_3$) δ 7.73 (d, J=7.2 Hz, 1H), 7.22-7.11 (m, 4H), 5.63 (brs, 1H), 5.41 (brs, 1H), 4.97 (t, J=7.2 Hz, 1H), 4.55 (s, 1H), 4.13-4.11 (m, 1H), 3.64 (t, J=6.4 Hz, 1H), 3.55 (d, J=5.2 Hz, 2H), 2.87 (t, J=6.4 Hz, 1H), 2.05-1.86 (m, 1H), 1.48-1.45 (m, 2H). 1.31-1.20 (m, 2H), 0.71-0.68 (m, 2H).

The compounds of Example 141-Example 149 were prepared by the preparation method described in Example 140.

TABLE 6

| Example | Compound Name | Structure | NMR data |
|---|---|---|---|
| 141 | E-3,4-dihydro-2H-quinolin-1-carboxylic acid[1-(5-carbamoyl-adamantan-2-ylcarbamoyl)-cyclopropyl-methyl]-amide | 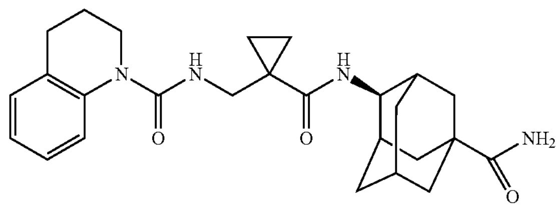 | ¹H NMR (400 MHz, CDCl₃) d 7.74 (d, J = 7.2 Hz, 1H), 7.27-7.16 (m, 3H), 7.11-7.07 (m, 1H), 5.64 (brs, 1H), 5.53-5.50 (m, 2H), 4.06-4.04 (m, 1H), 3.76 (t, J = 6.4 Hz, 2H), 3.55 (t, J = 6.4 Hz, 2H), 2.75 (t, J = 6.4 Hz, 2H), 2.11-1.89 (m, 11H), 1.56-1.53 (m, 2H), 1.28-1.21 (m, 2H), 0.61-0.59 (m, 2H) |
| 142 | E-piperidin-1-carboxylic acid[1-(5-carbamoyl-adamantan-2-ylcarbamoyl)-cyclopropyl-methyl]-amide | 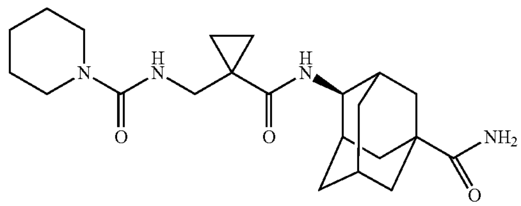 | ¹H NMR (400 MHz, CDCl₃) d 7.87 (d, J = 7.2 Hz, 1H) 5.66 (brs, 1H), 5.46 (brs, 1H), 4.86 (t, J = 6.4 Hz, 1H), 4.02-4.01 (m, 1H), 3.56-3.48 (m, 2H), 3.35-3.26 (m, 4H), 2.08-1.76 (m, 11H), 1.59-1.50 (m, 8H), 1.30-1.24 (m, 2H), 0.65-0.63 (m, 2H) |
| 143 | E-4-{[1-5-carbamoyl-adamantan-2-ylcarbamoyl)-cyclopropyl-methyl]-carbamoyl}-3,4-dihydro-2H-quinolin-1carboxylic acid-butylester | 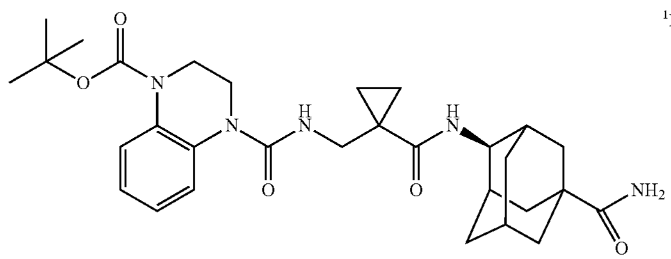 | ¹H NMR (400 MHz, CDCl₃) d 7.98 (d, J = 8.0 Hz, 1H), 7.59 (d, J = 8.0 Hz, 1H), 7.20-7.14 (m, 2H), 7.10-7.03 (m, 1H), 5.59 (brs, 1H), 5.51 (t, J = 6.4 Hz, 1H), 5.28 (brs, 1H), 4.07-4.05 (m, 1H), 3.86-3.78 (m, 4H), 3.54 (d, J = 3.2 Hz, 1H), 2.19-1.90 (m, 11H), 1.60-1.57 (m, 2H), 1.54 (s, 9H), 1.27-1.25 9m, 2H), 0.63-0.60 (m, 2H) |
| 144 | E-4-pyrimidin-2-yl-piperazin-1-carboxylic acid[1-(5-carbamoyl-adamantan-2-ylcarbamoyl)-cyclopropyl-methyl]-amide | 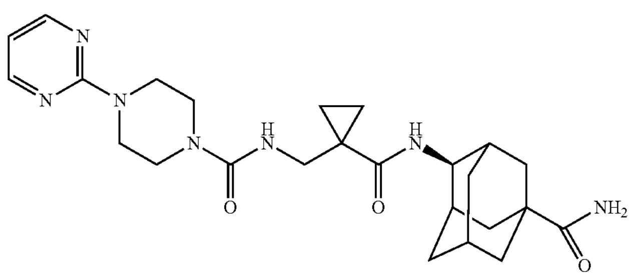 | ¹H NMR (400 MHz, CDCl₃) d 8.30 (d, J = 8.8 Hz, 2H), 6.65 (d, J = 4.8 Hz, 1H), 5.62 (brs, 1H), 5.37 (brs, 1H), 4.93 (t, J = 6.4 Hz, 1H), 4.02-4.01 (m, 1H), 3.90-3.84 (m, 4H), 3.57 (d, J = 8.8 Hz, 1H), 3.50-3.48 (m, 4H), 2.02-1.87 (m, 1H), 1.59-1.51 (m, 2H), 1.31-1.22 (m, 2H), 0.69-0.67 (m, 2H) |
| 145 | E-4-{(1[(3-phenyl-ureido)methyl]-cyclopropane-carbonyl)amino}-adamantan-1carboxylic acid amide | 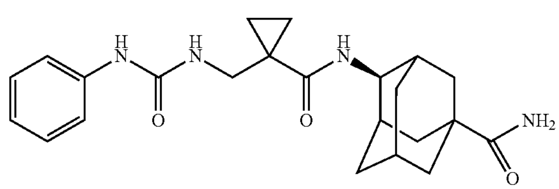 | ¹H NMR (400 MHz, CDCl₃) d 7.63-7.62 (m, 1H), 7.37-7.26 (m, 3H), 7.06-7.03 (m, 1H), 5.75-5.70 (brs, 2H), 5.42 (brs, 1H), 4.00 (brs, 1H), 3.50 (s, 2H), 2.07-1.85 (m, 11H), 1.53-1.48 (m, 2H), 1.26-1.22 (m, 2H), 0.66 (brs, 2H) |

TABLE 6-continued

| Example | Compound Name | Structure | NMR data |
|---|---|---|---|
| 146 | E-3,4-dihydro-2H-quinoxalin-1-carboxylic acid[1-(5-carbamoyl-adamantan-2-ylcarbamoyl)-cyclopropyl-methyl]-amide | 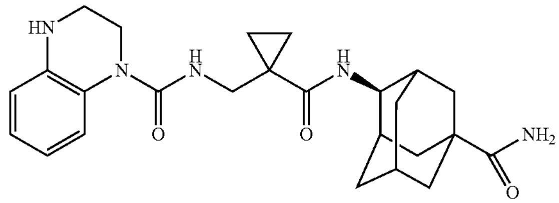 | $^1$H NMR (400 MHz, MeOD) d 7.80 (brs, 1H), 7.41-7.24 (m, 3H), 4.04-3.89 (m, 3H), 3.74-3.60 (m, 2H), 3.33 (s, 1H), 2.18-1.84 (m, 9H), 1.58-1.55 (m, 2H), 1.20 (brs, 2H), 0.91 (brs, 2H) |
| 147 | E-3,4-dihydro-1H-isoquinolin-2-carboxylic acid[4-(5-carbamoyl-adamantan-2-ylcarbamoyl)-thiazol-2-yl]-amide | 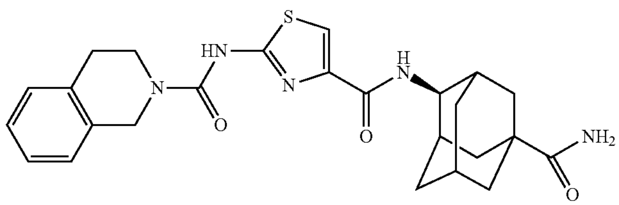 | $^1$H NMR (400 MHz, CDCl$_3$) d 7.80-7.60 (m, 2H), 7.40-7.20 (m, 6H), 5.70 (brs, 1H), 5.60 (brs, 1H), 4.70 (s, 2H), 4.20-4.10 (m, 1H), 3.80 (t, J = 6.4 Hz, 2H), 3.00 (t, J = 6.4 Hz, 2H), 2.10-1.80 (m, 9H), 1.65-1.55 (m, 2H) |
| 148 | E-3,4-dihydro-2H-quinolin-1-carboxylic acid[4-(5-carbamoyl-adamantan-2-ylcarbamoyl)-thiazol-2-yl]-amide | 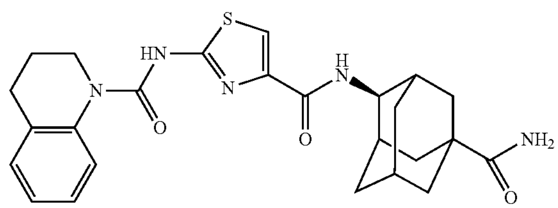 | $^1$H NMR (400 MHz, CDCl$_3$) d 7.49-7.44 (m, 1H), 7.19-7.17 (m, 2H), 7.13-7.05 (m, 4H), 5.74 (s, 1H), 5.67 (brs, 1H), 5.45 (brs, 1H), 3.97-3.95 (m, 1H), 3.77 (t, J = 6.4 Hz, 2H), 2.78 (t, J = 6.4 Hz, 2H), 2.05-1.80 9m, 13H), 1.62-1.58 (m, 2H), 1.54-1.51 9m, 2H), 1.01-0.97 (m, 2H) |
| 149 | E-2-(2-fluoro-benzamido)-thiazol-4-carboxylic acid(5-carbamoyl-adamantan-2-yl)amide | 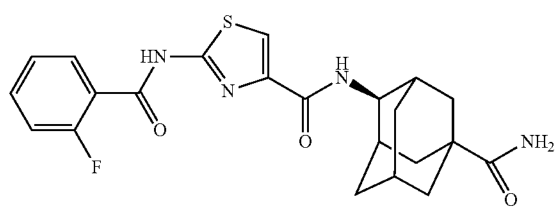 | $^1$H NMR (400 MHz, CDCl$_3$) d 8.08-8.04 (m, 1H), 7.52-7.42 (m, 1H), 7.34-7.29 (m, 2H), 7.20 (t, J = 4.0 Hz, 1H), 7.10 (t, J = 4.4 Hz, 1H), 5.67 (brs, 1H), 5.42 (brs, 1H), 4.16-4.14 (m, 1H), 2.12-1.92 (m, 9H), 1.80-1.60 (m, 4H) |

Experimental Example 1

Examination of 11β-HSD1 Inhibiting Effect

To investigate 11β-HSD1 inhibiting activity of the compounds prepared in the examples of the present invention, the following experiment was performed.

The inhibiting activity of 11β-HSD1 derived from microsomal fractions was measured using the HTRF assay (62CO2PEB, Cisbio). Different concentrations of compounds were added to 96-well plates, followed by the addition of TE buffer (20 mM Tris buffer and 5 mM EDTA, pH 6.0) containing 200 μM NADPH (N1630, Sigma) and 160 nM cortisone (C2755, Sigma), The reactions were initiated by the addition of human microsomal fractions (M0317, Sigma), and were allowed to incubate for 2 h at 37° C. Europium (Eu$^{3+}$) cryptate and XL665-conjugated cortisol were then added to each well and incubated for an additional 2 h at room temperature. The Cortisol concentration was calculated u sing a calibration curve. The IC$_{50}$ values were calculated from dose response curves using GraphPad Prism software. IC$_{50}$ of the example compound to 11β-HSD1 was obtained. The results are shown in Table 7.

TABLE 7

| Example | human IC$_{50}$ (nM) | Example | human IC$_{50}$ (nM) |
|---|---|---|---|
| 1 | 14.2 | 2 | 26.6 |
| 3 | 6.2 | 4 | — |
| 5 | 2.7 | 6 | — |
| 7 | 2.6 | 8 | 0.3 |
| 9 | 608.0 | 10 | 2.5 |
| 11 | 10.4 | 12 | 9.5 |
| 13 | 2.8 | 14 | 13.3 |

TABLE 7-continued

| Example | human IC$_{50}$ (nM) | Example | human IC$_{50}$ (nM) |
|---|---|---|---|
| 15 | 28.0 | 16 | 5.0 |
| 17 | 132.0 | 18 | 23.9 |
| 19 | 17.8 | 20 | 102.0 |
| 21 | 30.8 | 22 | 0.02 |
| 23 | — | 24 | 156.0 |
| 25 | 9.6 | 26 | 1.2 |
| 27 | — | 28 | 1.2 |
| 29 | — | 30 | — |
| 31 | 1.2 | 32 | 1.4 |
| 33 | 1.5 | 34 | 29.9 |
| 35 | — | 36 | 73.0 |
| 37 | 17.1 | — | — |
| 38 | 6.7 | 39 | 24.7 |
| 40 | 1.7 | 41 | 10.0 |
| 42 | 6.4 | 43 | 29.7 |
| 44 | 79.1 | 45 | 32.5 |
| 46 | 34.7 | 47 | 495.0 |
| 48 | 62.8 | 49 | — |
| 50 | 0.4 | 51 | — |
| 52 | — | 53 | — |
| 54 | — | 55 | — |
| 55 | 8.3 | 57 | 9.3 |
| 58 | 17.3 | 59 | 11.2 |
| 60 | 12.6 | 61 | 2.8 |
| 62 | 0.12 | 63 | 672.0 |
| 64 | 111.0 | 65 | — |
| 66 | — | 67 | 7.1 |
| 68 | 8.9 | 69 | 28.6 |
| 70 | 6.2 | 71 | 0.6 |
| 72 | 1.2 | 73 | 0.83 |
| 74 | 2.6 | 75 | 54.6 |
| 76 | 2.4 | 77 | — |
| 78 | — | 79 | — |
| 80 | 14.8 | 81 | 2.1 |
| 82 | — | 83 | 9.9 |
| 84 | 0.36 | 85 | — |
| 86 | — | 87 | — |
| 88 | 33.8 | 89 | — |
| 90 | — | — | — |
| 91 | — | 92 | 148.0 |
| 93 | — | 94 | 75.7 |
| 95 | 13.1 | 36 | 15.4 |
| 97 | 15.6 | 38 | 58.6 |
| 99 | 1.9 | 100 | 15.3 |
| 101 | — | 102 | 1.1 |
| 103 | 23.8 | 104 | — |
| 105 | 42.7 | 106 | 4.8 |
| 107 | 60.3 | 108 | 51.2 |
| 109 | — | 110 | — |
| 111 | — | 112 | — |
| 113 | 2.7 | 114 | 30.7 |
| 115 | 19.1 | 116 | 14.5 |
| 117 | 5.0 | 118 | 20.4 |
| 119 | 0.9 | 120 | 27.2 |
| 121 | 7.8 | 122 | 15.1 |
| 123 | 12.8 | 124 | — |
| 125 | 11.6 | 126 | 67.5 |
| 127 | 78.3 | 128 | — |
| 129 | 41.8 | 130 | — |
| 131 | — | 132 | 148.0 |
| 133 | 14.8 | 134 | — |
| 135 | — | 136 | — |
| 137 | — | 138 | 62.1 |
| 139 | — | 140 | 97.8 |
| 141 | 52.5 | 142 | — |
| 143 | — | 144 | — |
| 145 | — | 146 | 128.0 |
| 147 | — | 148 | — |
| 149 | — | — | — |

As shown in Table 7, IC$_{50}$ of the example compounds to 11β-HSD1 was 0.02-672.0 nM, indicating the compounds had a significant 11β-HSD1 inhibiting activity. In particular, IC$_{50}$ of those compounds prepared in Examples 8, 22, 50, 62, 71, 73, 84, and 119 were all less than 1.0 nM, indicating they had an excellent 11β-HSD1 inhibiting activity.

Therefore, the compound represented by formula 1 of the present invention can be effectively used for the prevention or treatment of diseases caused by abnormal activation of 11β-HSD1 such as non-insulin dependent type II diabetes, insulin resistance, obesity, lipid disorder, metabolic syndrome, and other diseases mediated by the excessive activity of glucocorticoid.

Experimental Example 2

In Vivo Study of the Lowering Effect on Plasma Glucose in KKAy Mouse Model

The inhibitory effect on plasma glucose of the compounds prepared in Examples of the present invention and showed an excellent 11β-HSD1 activity was investigated in vivo, <2-1> In Vivo Study Ay gene was introduced into KK mice to induce severe obesity and hyperglycemia. The male KKAy mice (9-week old, DaehanBioLink, Korea) having severe obesity and hyperglycemia prepared thereby were administered orally with the compounds prepared in Examples 3, 22, 71, 84, 113, and 119 at the concentrations of 50 mg/kg and 100 mg/kg. After 4 hour-fasting, the levels of plasma glucose and insulin were measured. The test continued for 3 weeks.

<2-2> Plasma Glucose Lowering Effect

KKAy mice were administered orally with the compounds prepared in Examples 3, 22, 71, and 113 at the concentration of 100 mg/kg for 3 weeks. Thereafter, the level of plasma glucose after fasting was measured. As a result, the plasma glucose lowering effect was approximately 9% in the group treated with the compound of Example 3. In the group treated with the compound of Example 22, the level of plasma glucose was decreased approximately 32%. In the groups treated with the compounds of Examples 71 and 113, the plasma glucose lowering effect was respectively 27% and 28%.

In the group treated with the compound of Example 84 at the concentration of 50 mg/kg, the plasma glucose lowering effect was 19%. In the group treated with the compound of Example 119 at the concentration of 50 mg/kg, the plasma glucose lowering effect was 47%. The results are shown in Table 8.

TABLE 8

| | Plasma glucose lowering effect | | | | | |
|---|---|---|---|---|---|---|
| | Example 3 | Example 22 | Example 71 | Example 84 | Example 113 | Example 119 |
| 100 mg/kg | 9% | 32% | 27% | | 28% | |
| 50 mg/kg | | | | 19% | | 47% |

<2-3> Plasma Insulin Lowering Effect

KKAy mice were administered orally with the compounds prepared in Examples 22, 71, and 113 at the concentration of 100 mg/kg for 3 weeks. Thereafter, the level of plasma insulin after fasting was measured. As a result, the plasma insulin lowering effect was approximately 53% in the group treated with the compound of Example 22. In the groups treated with the compounds of Examples 71 and 113, the plasma insulin lowering effect was respectively 40% and 60%.

In the group treated with the compound of Example 84 at the concentration of 50 mg/kg, the plasma insulin lowering effect was 43%. In the group treated with the compound of Example 119 at the concentration of 50 mg/kg, the plasma insulin lowering effect was 52%. The results are shown in Table 9.

TABLE 9

| | Plasma insulin lowering effect | | | | |
|---|---|---|---|---|---|
| | Example 22 | Example 71 | Example 84 | Example 113 | Example 119 |
| 100 mg/kg | 53% | 40% | | 60% | |
| 50 mg/kg | | | 43% | | 52% |

As shown in Table 8 and Table 9, when the compounds prepared in Examples 3, 22, 71, 84, 113, and 119 were treated to KKAy mice at the concentration of either 100 mg/kg or 50 mg/kg, the levels of plasma glucose and plasma insulin were significantly reduced. These results suggest that the compounds have an excellent anti-diabetic effect.

Therefore, the compound represented by formula 1 of the present invention can be effectively used for the prevention or treatment of diseases caused by the abnormal activation of 11β-HSD1 such as non-insulin dependent type II diabetes, insulin resistance, obesity, lipid disorder, metabolic syndrome, and other diseases mediated by the excessive activity of glucocorticoid.

The compound represented by formula 1 of the present invention can be formulated in various forms according to the purpose of use. The followings are the examples of formulations comprising the compound of formula 1 of the present invention as an active ingredient, but these cannot limit the present invention thereto.

Manufacturing Example 1

Preparation of Powders

| The compound of formula 1 | 2 g |
|---|---|
| Lactose | 1 g |

Powders were prepared by mixing all the above components, which were filled in airtight packs according to the conventional method for preparing powders.

Manufacturing Example 2

Preparation of Tablets

| The compound of formula 1 | 100 mg |
|---|---|
| Corn starch | 100 mg |
| Lactose | 100 mg |
| Magnesium stearate | 2 mg |

Tablets were prepared by mixing all the above components by the conventional method for preparing tablets.

Manufacturing Example 3

Preparation of Capsules

| The compound of formula 1 | 100 mg |
|---|---|
| Corn starch | 100 mg |
| Lactose | 100 mg |
| Magnesium stearate | 2 mg |

Capsules were prepared by mixing all the above components, which were filled in gelatin capsules according to the conventional method for preparing capsules.

Manufacturing Example 4

Preparation of Injectable Solutions

| The compound of formula 1 | 100 mg |
|---|---|
| Mannitol | 180 mg |
| $Na_2HPO_4 \cdot 2H_2O$ | 26 mg |
| Distilled water | 2974 mg |

Injectable solutions were prepared by mixing all the above components by the conventional method for preparing injectable solutions.

INDUSTRIAL APPLICABILITY

Since the compound of the present invention selectively inhibits the activity of 11β-HSD1 (11β-Hydroxysteroid dehydrogenase type 1), the compound of the invention can be effectively used as a therapeutic agent for the treatment of diseases caused by the over-activation of 11β-HSD1 such as non-insulin dependent type II diabetes, insulin resistance, obesity, lipid disorder, metabolic syndrome, and other diseases or condition mediated by the excessive activity of glucocorticoid.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended Claims.

What is claimed is:

1. A compound or pharmaceutically acceptable salt thereof, wherein the compound is selected from the group consisting of the following compounds:
   - (3) E-4-[1-((2-fluoro-benzenesulfonylamino)methyl)cyclopropanecarboxamido]-adamantan-1-carboxylic acid amide;
   - (22) E-4-[1-((2-fluoro-N-methyl-benzenesulfonylamino)methyl)cyclopropanecarboxamido]-adamantan-1-carboxylic acid amide;
   - (71) E-4-[2-(2-fluoro-benzenesulfonylamino)-2-methylpropanamido]-adamantan-1-carboxylic acid amide;
   - (84) E-4-[2-(2,6-difluoro-benzenesulfonylamino)-2-methylpropanamido]adamantan-1-carboxylic acid amide;
   - (113) E-sodium[3-((5-carbamoyladamantan-2-yl)carbamoyl)phenyl]-2-fluoro-3-chloro-benzenesulfonylamide; and
   - (119) E-4-[3-(3,5-dichloro-benzenesulfonylamino)-benzamido]-adamantan-1-carboxylic acid amide.

2. A preparation method of the compound of claim 1 containing the step of reacting the compound represented by formula 2 with the compound represented by formula 3 in the presence of an organic solvent to prepare the compound of formula 1:

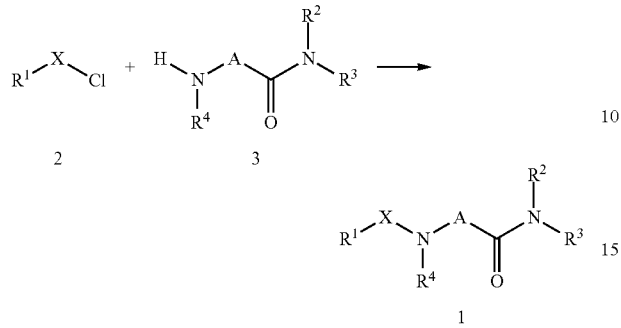

wherein,
X is sulfonyl,
$R^1$ is $R^2$ is —H,
$R^3$ is $R^4$ is —H, —$CH_3$ or —Na, and
A is 3. A pharmaceutical composition for the treatment of a disease, comprising the compound or the pharmaceutically acceptable salt thereof according to claim 1 as an active ingredient, wherein the disease is non-insulin dependent type II diabetes, insulin resistance, obesity, lipid disorder or metabolic syndrome.

* * * * *